(12) United States Patent
Zhadkevich

(10) Patent No.: US 10,258,348 B2
(45) Date of Patent: Apr. 16, 2019

(54) DEVICES AND TECHNIQUES FOR VASCULAR COMPRESSION

(71) Applicant: Michael Zhadkevich, Inmann, SC (US)

(72) Inventor: Michael Zhadkevich, Inmann, SC (US)

(*) Notice: Subject to any disclaimer, the term of this patent is extended or adjusted under 35 U.S.C. 154(b) by 492 days.

(21) Appl. No.: 15/008,276

(22) Filed: Jan. 27, 2016

(65) Prior Publication Data

US 2016/0213381 A1    Jul. 28, 2016

Related U.S. Application Data

(60) Provisional application No. 62/142,431, filed on Apr. 2, 2015, provisional application No. 62/108,059, filed on Jan. 27, 2015.

(51) Int. Cl.
| | |
|---|---|
| *A61B 17/132* | (2006.01) |
| *A61B 17/135* | (2006.01) |
| *A61B 5/02* | (2006.01) |
| *A61B 5/024* | (2006.01) |
| *A61B 5/00* | (2006.01) |
| *A61B 17/00* | (2006.01) |

(52) U.S. Cl.
CPC ...... *A61B 17/1325* (2013.01); *A61B 5/02014* (2013.01); *A61B 5/02422* (2013.01); *A61B 17/1355* (2013.01); *A61B 5/6822* (2013.01); *A61B 2017/00022* (2013.01); *A61B 2017/00106* (2013.01); *A61B 2017/00119* (2013.01); *A61B 2017/00132* (2013.01); *A61B 2505/05* (2013.01)

(58) Field of Classification Search
CPC .............. A61B 17/1325; A61B 17/132; A61B 17/1322; A61B 2017/00022; A61B 5/6822

See application file for complete search history.

(56) References Cited

U.S. PATENT DOCUMENTS

| | | |
|---|---|---|
| 2,271,927 A | 2/1942 | Saighman |
| 2,571,461 A | 10/1951 | Livingston |
| 2,676,586 A | 4/1954 | Coakwell, Jr. |
| 3,587,584 A | 6/1971 | Bourbon |
| 4,676,232 A | 6/1987 | Olsson et al. |
| 4,686,085 A | 8/1987 | Osterholm |
| 4,745,924 A | 5/1988 | Ruff |

(Continued)

FOREIGN PATENT DOCUMENTS

| | | |
|---|---|---|
| CN | 201 356 600 Y | 12/2009 |
| EP | 0100827 A1 | 5/1984 |

(Continued)

OTHER PUBLICATIONS

European Patent Office; Communication Regarding Extended European Search Report pursuant to Rule 62 EPC; European Application No. 17190479.0-1122; European Patent Office; pp. 1-7; publisher European Patent Office; Published Munich Germany; copyright and dated Jan. 16, 2018, (7 pages).

(Continued)

*Primary Examiner* — Diane D Yabut
(74) *Attorney, Agent, or Firm* — J. Bennett Mullinax, LLC

(57) ABSTRACT

The present disclosure provides for specific shapes and combinations of the compression members amenable to the safest, yet most effective compression of the carotid and vertebral arteries aimed at prevention of embolic stroke. An associated method of achieving an optimal compression of said arteries for the purpose of stroke prevention is provided.

20 Claims, 45 Drawing Sheets

(56) References Cited

U.S. PATENT DOCUMENTS

| | | | |
|---|---|---|---|
| 5,271,409 A | 12/1993 | Millay | |
| 5,312,350 A | 5/1994 | Jacobs | |
| 5,348,015 A | 9/1994 | Moehring | |
| 5,372,575 A | 12/1994 | Sebastian | |
| 5,376,067 A | 12/1994 | Daneshvar | |
| 5,441,051 A | 8/1995 | Hileman | |
| 5,514,079 A | 5/1996 | Dillon | |
| 5,685,321 A * | 11/1997 | Klingenstein | A61F 5/445 |
| | | | 128/845 |
| 5,741,295 A | 4/1998 | McEwen | |
| 5,792,173 A | 8/1998 | Breen | |
| 6,063,036 A | 5/2000 | Li | |
| 6,336,901 B1 | 1/2002 | Itonaga et al. | |
| 6,547,736 B1 | 4/2003 | Moehring | |
| 7,074,177 B2 | 7/2006 | Pickett | |
| 7,314,478 B2 | 1/2008 | Hui | |
| 7,727,254 B2 | 6/2010 | Pah | |
| 7,972,356 B2 | 7/2011 | Boyle et al. | |
| D643,538 S | 8/2011 | Vivenzio | |
| 7,988,104 B1 | 8/2011 | Cook et al. | |
| 7,998,104 B2 | 8/2011 | Chang | |
| 8,025,674 B2 | 9/2011 | Barbut et al. | |
| 8,062,324 B2 | 11/2011 | Shimon et al. | |
| 2001/0025643 A1 | 10/2001 | Foley | |
| 2004/0098035 A1 | 5/2004 | Wada | |
| 2005/0075531 A1 | 4/2005 | Loeb et al. | |
| 2006/0100530 A1 | 5/2006 | Kliot | |
| 2006/0241485 A1 | 10/2006 | Hacker et al. | |
| 2007/0173888 A1 | 7/2007 | Rousso | |
| 2008/0154140 A1 | 6/2008 | Chang et al. | |
| 2008/0262535 A1 | 10/2008 | Gavriely et al. | |
| 2009/0209925 A1 | 8/2009 | Marinello | |
| 2009/0287101 A1 | 11/2009 | Ferran | |
| 2010/0082060 A1 | 4/2010 | Avitable | |
| 2010/0094332 A1 | 4/2010 | Willshaw | |
| 2010/0324429 A1 | 12/2010 | Leschinsky | |
| 2010/0324589 A1 | 12/2010 | Carpenter et al. | |
| 2011/0028934 A1 | 2/2011 | Buckman et al. | |
| 2013/0023909 A1 | 1/2013 | Duhay | |
| 2013/0304111 A1 | 11/2013 | Zhadkevich | |
| 2014/0135816 A1 | 5/2014 | Hyde et al. | |
| 2014/0236221 A1 | 8/2014 | Zhadkevich | |
| 2015/0018869 A1 | 1/2015 | Benz et al. | |
| 2015/0080942 A1 | 3/2015 | Garrison | |
| 2015/0313607 A1 | 11/2015 | Zhadkevich | |
| 2016/0030001 A1 | 2/2016 | Stein | |

FOREIGN PATENT DOCUMENTS

| | | |
|---|---|---|
| EP | 0203310 A2 | 12/1986 |
| EP | 0 462 088 A2 | 12/1991 |
| EP | 0934728 A1 | 8/1999 |
| EP | 2662034 A1 | 11/2013 |
| EP | 2 796 099 A1 | 10/2014 |
| FR | 899349 A | 2/1931 |
| FR | 719730 A | 2/1932 |
| WO | WO 98/46144 A1 | 10/1998 |
| WO | WO 99/38028 A1 | 7/1999 |
| WO | WO 2007/074350 A1 | 7/2007 |
| WO | WO 2008/009932 A1 | 1/2008 |
| WO | WO 2008/150966 A1 | 12/2008 |
| WO | WO 2010/141752 A1 | 12/2010 |
| WO | WO 2011/088543 A1 | 7/2011 |
| WO | WO 2014/027347 A1 | 2/2014 |
| WO | WO 2014/037960 A1 | 3/2014 |
| WO | WO 2014/070993 A1 | 5/2014 |

OTHER PUBLICATIONS

European Patent Office; Communication Regarding Extended European Search Report pursuant to Rule 62 EPC; European Application No. 17199143.3-1122; European Patent Office; pp. 1-10; publisher European Patent Office; Published Munich Germany; copyright and dated Feb. 14, 2018; (10 pages).

Gabor Erdoes, MD, titled "Letter by Erdoes et al Regarding Article, Cerebral Embolization During Transcatheter Aortic Valve Implantation: A Transcranial Doppler Study," item title "Journal of the American Heart Association"; copyright 2013; p. 590; No. 127; American Heart Association, Inc.; Dallas Texas, USA; (2 pages).

Marie-Christine Guilbert, titled "Arterial trauma during central venous catheter insertion: Case series, review and proposed algorithm," item title "Journal of Vascular Surgery", copyright 2008, pp. 918-925, vol. 48, No. 4, Canadian Society for Vascular Surgery; Montreal, Quebec, Canada; (8 pages).

Philipp Kahlert, "Cerebral Embolization During Transcatheter Aortic Valve Implantation: A Transcranial Doppler Study," Item titled "Journal of the American Heart Association", copyright Aug. 16, 2012; pp. 1245-1255; No. 126; American Heart Association, Inc.; Dallas, Texas, USA; (16 pages).

H. Loffler; Stratum corneum adhesive tape stripping: influence of anatomical site, application pressure, duration and removal; British Journal of Dermatology; 2004; pp. 748-752; vol. 151; publisher United States Patent and Trademark Office; Published United Kingdom; copyright 2004 British Association of Dermatologists; (8 pages).

European Patent Office; Communication Pursuant to Article 94(3) EPC; European Patent Application No. 16 152 913.6-1664; European Patent Office; pp. 1-5; Publisher European Patent Office; Munich, Germany; copyright dated May 3, 2017; (5 pages).

European Patent Office; European Search Report; European Patent Application No. 16152913.6-1654; European Patent Office; pp. 1-9; publisher European Patent Office; Published Munich, Germany; copyright dated Jun. 16, 2016; (9 pages).

European Patent Office, Communication pursuant to Article 94(3) EPC; European Patent Office, published May 3, 2017. pp. 1-5, European Patent Application No. 16152913.6-1664, Publisher European Patent Office, Munich, Germany, 5 pages.

* cited by examiner

DEVICES AND TECHNIQUES FOR VASCULAR COMPRESSION

RELATED APPLICATIONS

This application claims the benefit of U.S. Provisional Application No. 62/108,059, filed on Jan. 27, 2015, entitled "Shape and Configuration of the Carotid and Vertebral Compression Members for Safe and Effective Vascular Compression and Prevention of Stroke and Method of Use," which is incorporated by reference herein in its entirety. This application also claims the benefit of U.S. Provisional Application No. 62/142,431, filed on Apr. 2, 2015, entitled "Shape and Configuration of the Carotid and Vertebral Compression Members for Safe and Effective Vascular Compression and Prevention of Embolic Stroke and Method of Use," which is incorporated by reference herein in its entirety.

TECHNICAL FIELD

The subject technology relates to prevention of embolic and ischemic injury (such as ischemia and stroke) as a consequence of emboligenic events and interventions.

BACKGROUND

Arterial embolism, leading to embolic ischemia or stroke, is one of the most dreadful complications of cardiac, aortic and vascular procedures, diagnosed in 1-22% of patients undergoing cardiovascular surgery. Even more frequently, in up to 86% of cases, patients undergoing heart, valve, coronary artery bypass, aortic surgery, cardiac catheterization, or even simple endovascular interventions experience subclinical embolic events as recorded by transcranial Doppler or magnetic resonance imaging (MRI). These embolic events can lead to cognitive impairment, disability, extremity ischemia, multiple organ failure, dementia, and death having a significant impact on patients' recovery. With more than 1.2 million cardiovascular procedures performed in the United States alone, this issue has a significant socio-economic impact.

The main sources of emboli in this setting reside in the heart, heart valves, thoracic aorta, and great vessels when these structures are intervened thereon (i.e. when an emboligenic procedure is performed). Even simple cardiac catheterization with an endovascular catheter can induce microtrauma of the atherosclerotic thoracic aorta leading to formation of embolic particles with subsequent embolic brain, liver, kidney and extremity injury ranging from latent ischemic foci to a massive or even fatal event. Multiple devices are known that attempt to prevent embolization of the carotid arteries during endovascular and cardiac interventions by using different types of filters, deflection devices, endoluminal balloons, shields, or other embolic traps or deflectors. These anti-embolic devices, however, have not received wide acceptance in surgery of the heart, heart valves and thoracic aorta due to their complexity and invasive character with the risk of additional trauma to the inner vessel wall resulting in a high risk to benefit ratio. Known devices require insertion of additional hardware into the arterial system or aorta, a procedure that is known by itself to be associated with all classical risks of endovascular intervention, including aortic dissection, bleeding, thrombosis, and arterial embolization. One known intra-aortic filter device that is inserted into the ascending portion of the thoracic aorta via an aortic cannula to capture potential embolic material released from the heart and aortic wall during heart surgery was found to be quite difficult to implement and was reported to be associated with major trauma to aortic wall and acute aortic dissection.

Aside from introducing hardware into the patient and causing the aforementioned problems, intravascular filters are not able to capture embolus smaller than the pore size of the available devices (currently 60-140 µm) resulting in cerebral microembolization. Furthermore, the placement of the filter by itself may produce cerebral emboli. For example, the mere passing of a guide wire into a carotid artery generates approximately 40,000 microemboli, with a significant percentage of small, less than 60 µm, particles that are not retained by standard filters. Therefore, in spite of multiple innovations in the field of anti-embolic devices, the problem of arterial emboli and stroke during cardiovascular surgery is far from being resolved. As such, there remains room for variation and improvement within the art.

SUMMARY

Embodiments of the present disclosure relate to devices and techniques for vascular compression. More particularly, the present disclosure relates to a device having compression members of a specific cross-sectional shape or combination of cross-sectional shapes for vascular compression, such as compression of arteries.

In accordance with the present disclosure, there is provided a device for diverting emboli from a cerebral circulation of a patient. The device comprises a first compression member configured to be applied to a first artery of the patient when the device is placed around a neck of the patient, the first compression member having an unactuated state and an actuated state, wherein the first compression member has an anatomically congruent cross-sectional shape such that, when in the actuated state, the first compression member applies a greater amount of force on the artery than on a trachea or a sternocleidomastoid muscle of the patient. The device also comprises a second compression member configured to be applied to a second artery of the patient when the device is placed around the neck of the patient, the second compression member having an unactuated and an actuated state, wherein the second compression member has an anatomically congruent cross-sectional shape such that, when in the actuated state, the second compression member applies a greater amount of force on the second artery than on the trachea or a sternocleidomastoid muscle of the patient.

In accordance with other aspects of the disclosure, the device further comprises a third compression member configured to be applied to a third artery of the patient when the device is placed around the neck of the patient, the third compression member having an unactuated state and an actuated state, wherein the third compression member has an anatomically congruent cross-sectional shape configured such that, when in the actuated state, the third compression member applies a greater amount of force on the third artery than on an anterior scalenus muscle, a longus colli muscle, or a sternocleidomastoid muscle of the patient. The device also comprises a fourth compression member configured to be applied to a fourth artery of the patient when the device is placed around the neck of the patient, the fourth compression member having an unactuated state and an actuated state, wherein the fourth compression member has an anatomically congruent cross-sectional shape configured such that, when in the actuated state, the fourth compression member applies a greater amount of force on the fourth artery than on an anterior scalenus muscle, a longus colli muscle, or a sternocleidomastoid muscle of the patient.

In accordance with additional aspects of the disclosure, a cross-sectional shape of the first compression member is one of an oval shape, a conic shape, a pear shape, a bilobar shape, a trilobar shape, a finger shape, or a multiple finger shape.

In accordance with further aspects of the disclosure, the second compression member comprises two compression members, a first of the two compression members having an arcuate or crescent cross-sectional shape, and a second of the two compression members having a conic, oval or pear cross-sectional shape.

In accordance with still further aspects of the disclosure, at least one of the first compression member or the second compression member comprises foam.

In accordance with other aspects of the disclosure, at least one of the first compression member or the second compression member is inflatable.

In accordance with still other aspects of the disclosure, the device has a hinge positioned between the first compression member and the second compression member, wherein the hinge is configured to be actuated to adjust one of a distance between the first compression member and the first artery and a distance between the second compression member and the second artery. The hinge may be capable of providing a different degree of angulation between a left portion and a right portion of the compression device at a level of a cervical portion of a trachea of the patient.

In accordance with additional aspects of the disclosure, the first compression member is disposed in an insertion pocket of the device, the insertion pocket being adapted for removal of the first compression member and insertion of a third compression member that is different in cross-sectional shape than the first compression member.

In accordance with other aspects of the disclosure, the first artery is a carotid artery.

In accordance with still other aspects of the disclosure, the third artery is a vertebral artery.

In accordance with further aspects of the disclosure, the first compression member includes a Doppler probe configured to detect embolic particles in the first artery. In accordance with some embodiments, a third compression member may include a Doppler probe configured to detect embolic particles in a third artery.

In accordance with other aspects of the disclosure, the first compression member includes one of a Doppler probe or a pulse oximeter configured to detect a correct amount of compression on the first artery. In accordance with some embodiments, the first compression member may detect moving particles in the first artery, which may reflect potential vascular emboli.

In accordance with still other aspects of the disclosure, the first compression member has a cross-sectional multiple finger shape and is configured to compress along a length of the first artery.

In accordance with further aspects of the disclosure, the first compression member, when actuated, is configured to exert pressure onto the trachea and the sternocleidomastoid muscle so as to stabilize the first compression member on the first artery.

In accordance with other aspects of the disclosure, the device is configured to be positioned adjacent to the trachea, and the portion of the device adjacent to the trachea is narrower in a longitudinal direction parallel to the longitudinal axis of the neck than a portion of the device including the first compression member.

In accordance with additional aspects of the disclosure, the first compression member assumes the cross-sectional shape when in its actuated state.

In accordance with further aspects of the disclosure, the hinge can be actuated to adjust an angle formed by the hinge between a side of the device comprising the first compression member and a side of the device comprising the second compression member, wherein the angle is between 35 degrees and 140 degrees when the first compression member and the second compression member are in their actuated states.

In accordance with still further aspects of the disclosure, an angle between a longitudinal axis of the first artery and a longitudinal axis of the first compression member is between 0 and 65 degrees when the first compression member is in its actuated state.

In accordance with other aspects of the disclosure, the third compression member includes a Doppler probe configured to detect embolic particles in the third artery.

In accordance with further aspects of the disclosure, the third compression member includes one of a Doppler probe or a pulse oximeter configured to detect a correct amount of compression on the third artery.

Furthermore, in accordance with the present disclosure, there is provided a kit for use in diverting emboli from a cerebral circulation of a patient. The kit comprises a compression device for placement around a neck of the patient, the compression device having insertion slots. The kit also comprises compression members, wherein at least a first of the compression members has a different cross-sectional shape than a second of the compression members, and wherein each of the first and second compression members are configured for insertion into one of the insertion slots.

In accordance with aspects of the disclosure, the kit comprises a sizing template with a size and curvature, wherein the sizing template is configured to provide measurement between arteries of the neck of the patient.

In accordance with other aspects of the disclosure, the kit comprises a plurality of different sizing templates, each of the sizing templates having a unique size or curvature.

In accordance with further aspects of the disclosure, the first compression member has a cross-sectional shape that is one of an oval shape, a conic shape, a pear shape, a bilobar shape, a trilobar shape, a finger shape, or a multiple finger shape.

In accordance with additional aspects of the disclosure, the first compression member comprises two compression members, a first of the two compression members having an arcuate or crescent cross-sectional shape, and a second of the two compression members having a conic, oval, or pear cross-sectional shape.

In accordance with other aspects of the disclosure, the kit comprises a plurality of compression devices, wherein each of the compression devices has a different size.

In accordance with further aspects of the disclosure, the compression device has two insertion slots, each of which is configured for positioning along an artery of the patient.

In accordance with additional aspects of the disclosure, the compression device has four insertion slots, each of which is configured for positioning along an artery of the patient.

In accordance with other aspects of the disclosure, at least one of the first or second compression members comprises foam.

In accordance with further aspects of the disclosure, at least one of the first or second compression members is inflatable.

Additionally, in accordance with the present disclosure, there is provided a method of diverting emboli from cerebral circulation of a patient. The method comprises determining an anatomical characteristic of a neck of the patient, and selecting a compression member having a particular cross-sectional shape from a plurality of compression members based on the characteristic. The method also comprises coupling the compression member to a compression device. The method further comprises positioning the compression member at an artery of the patient by positioning the compression device around the neck of the patient. The method still further comprises actuating the first compression member to compress the artery.

In accordance with aspects of the disclosure, the method further comprises selecting the compression device from a plurality of compression devices based on a size of the compression device and the determined anatomical characteristic of the neck of the patient.

In accordance with other aspects of the disclosure, the method further comprises measuring the distance between the artery and another artery of the patient using a sizing template to determine the characteristic of the neck of the patient.

In accordance with further aspects of the disclosure, the method still further comprises adjusting an angle of a hinge of the compression device such that an angle of the hinge is between 35 degrees and 140 degrees when the first compression member is actuated.

Still further, in accordance with the present disclosure, there is provided a method of diverting emboli from a cerebral circulation of a patient. The method comprises placing a compression device around a neck of the patient, such that a compression member attached to the compression device is positioned for application of pressure to an artery. The method also comprises actuating the compression member to apply force to the artery, wherein an amount of the force applied by the compression member to the artery is greater than an amount of force applied by the compression member to a trachea or a sternocleidomastoid muscle of the patient.

Before explaining example embodiments consistent with the present disclosure in detail, it is to be understood that the disclosure is not limited in its application to the details of constructions and to the arrangements set forth in the following description or illustrated in the drawings. The disclosure is capable of embodiments in addition to those described and is capable of being practiced and carried out in various ways. Also, it is to be understood that the phraseology and terminology employed herein, as well as in the abstract, are for the purpose of description and should not be regarded as limiting.

It is to be understood that both the foregoing general description and the following detailed description are explanatory only and are not restrictive of the claimed subject matter.

BRIEF DESCRIPTION OF THE DRAWINGS

The accompanying drawings, which are incorporated in and constitute part of this specification, and together with the description, illustrate and serve to explain the principles of various example embodiments.

DETAILED DESCRIPTION OF EXAMPLE EMBODIMENTS

Figure 1:
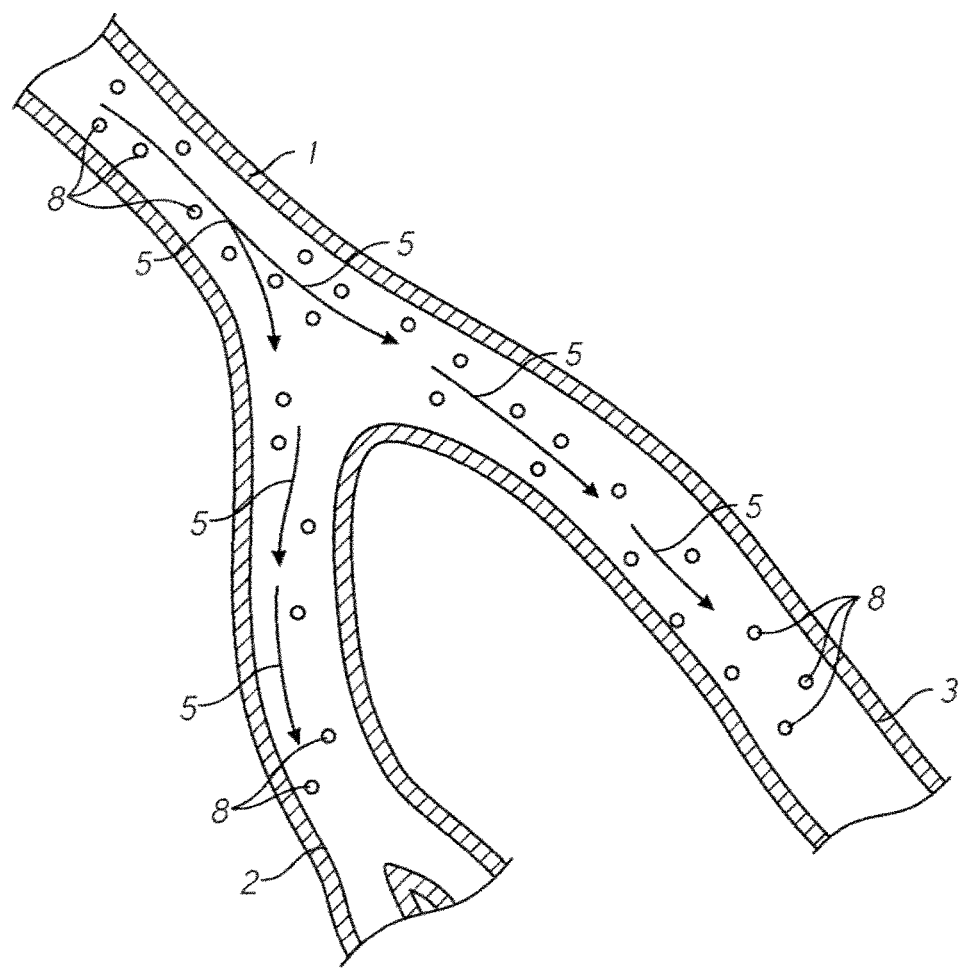
FIG. 1 is an example of a view of a blood vessel, with the blood in the vessel carrying emboli. The blood vessel branches into vessels carrying the blood to different areas and organs.
Figure 2:
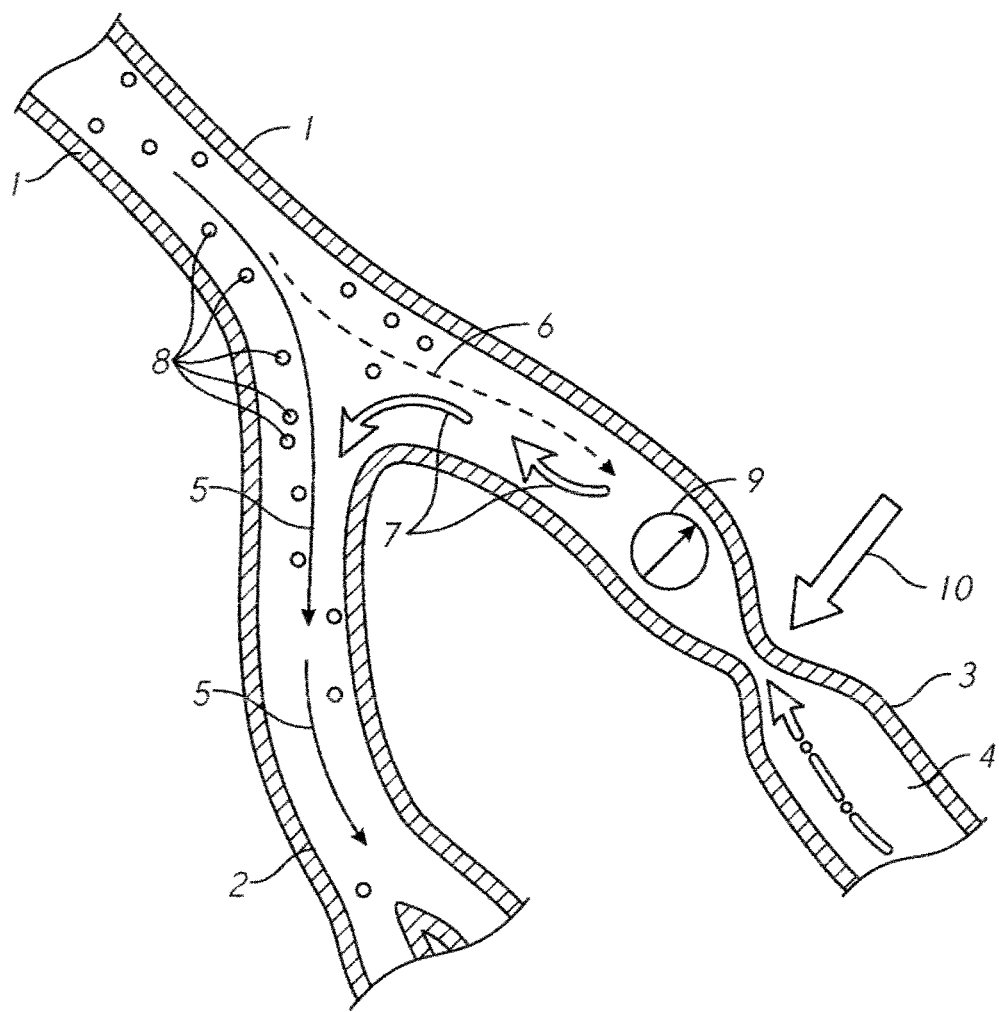
FIG. 2 is an example of a view of a blood vessel, with the blood in the vessel carrying emboli, where an external compression of a branch carrying blood to an organ (such as a brain) will divert the emboli to another vessel.
Figure 3:
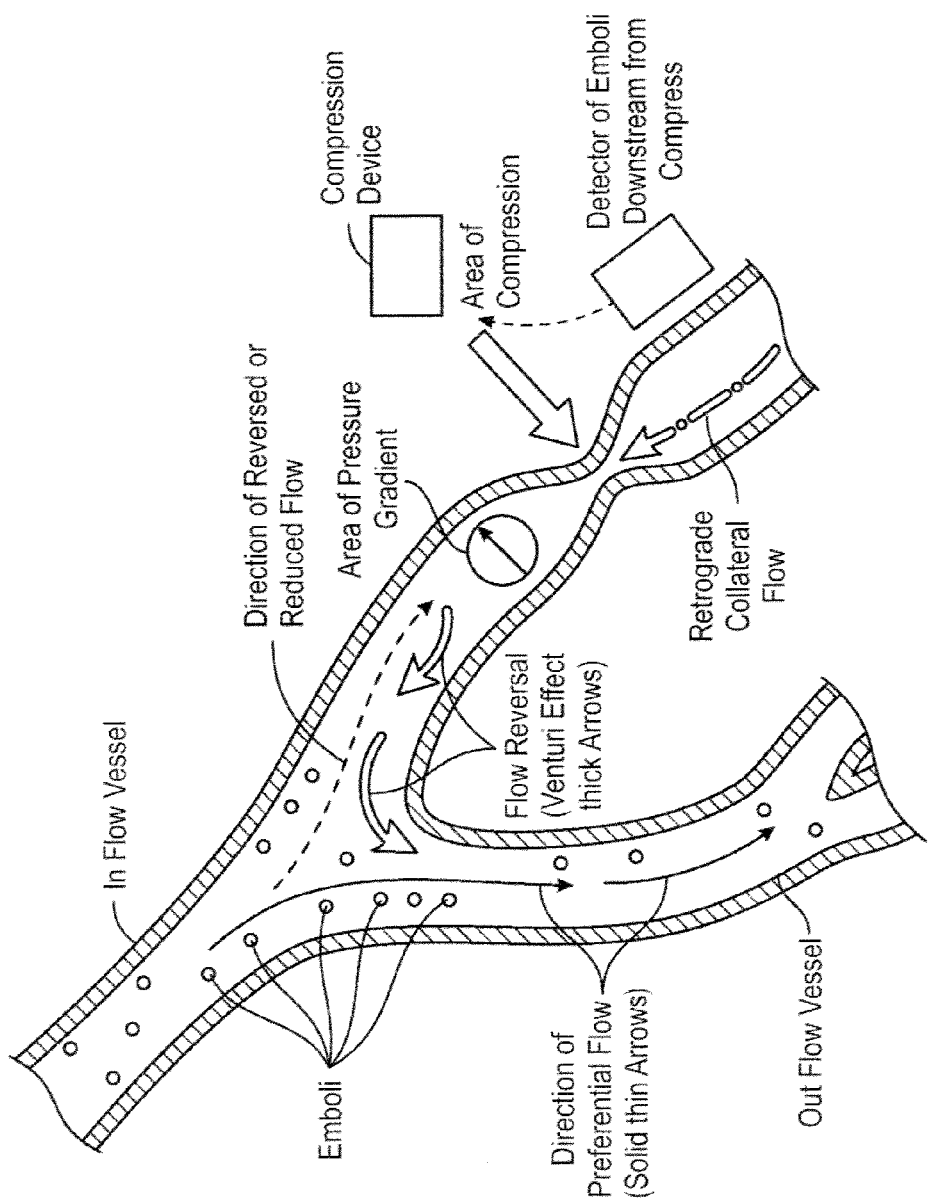
FIG. 3 is an example schematic representation of a method of protection from vascular emboli with an option of an automated external compression of an artery carrying blood to an organ.
Figure 4:
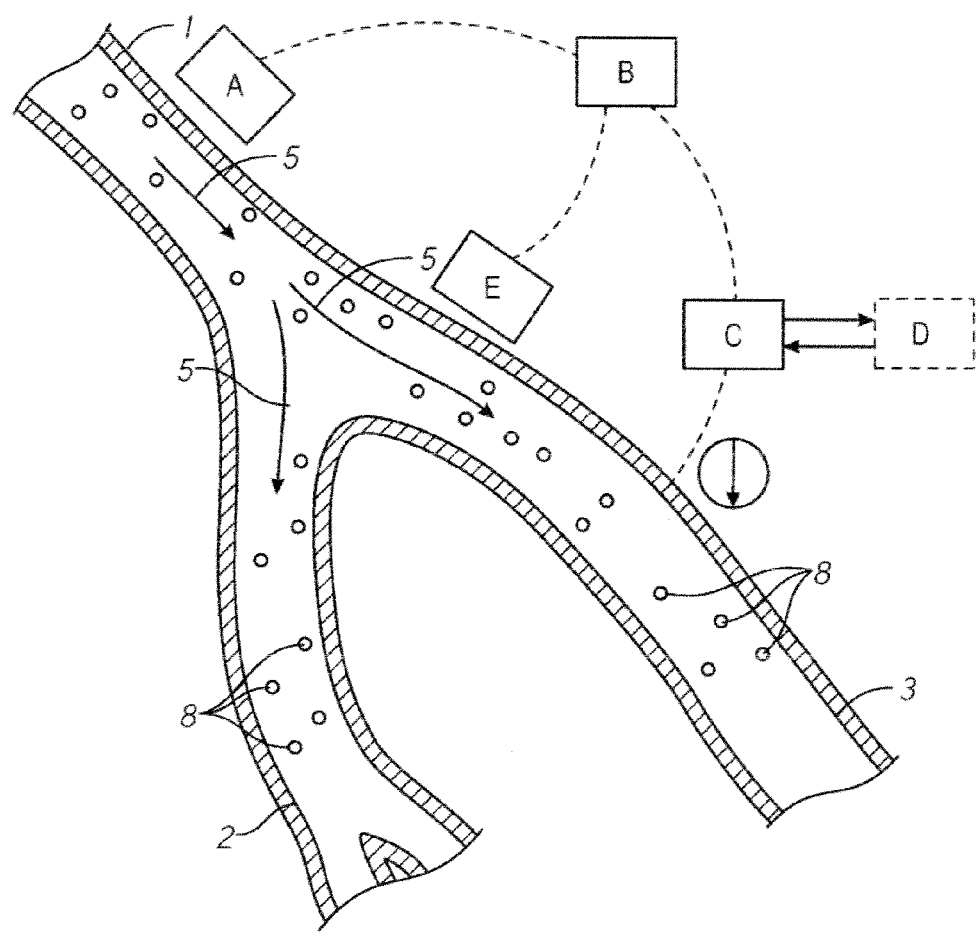
FIG. 4 represents an example mechanism of detecting embolic particles upstream from an organ to be protected with an automated feedback signaling system that is able to trigger a process of arterial or venous compression to limit entry of emboligenic particles into the organ.
Figure 5:
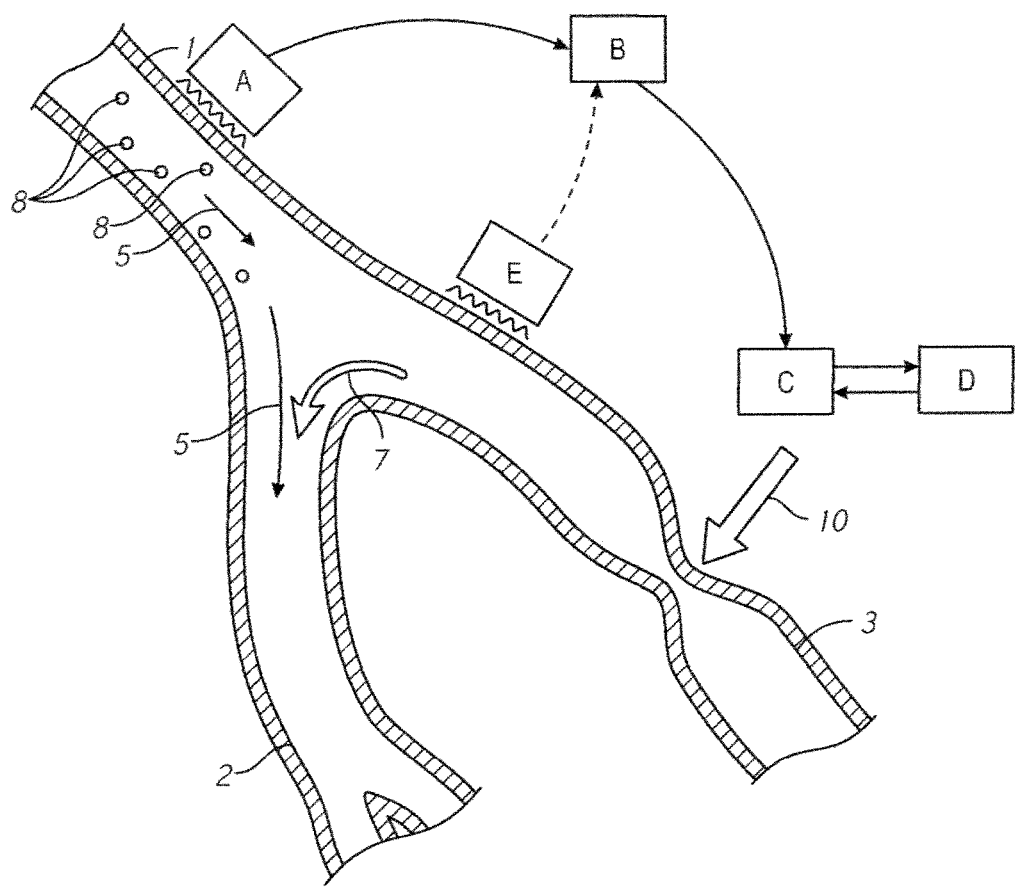
FIGS. 5 and 6 show an example of compression of an artery, triggered by detection of the embolic particles in an afferent vessel, cardiac systole, or other parameters with subsequent diversion of emboli into a less important blood vessel.
Figure 6:
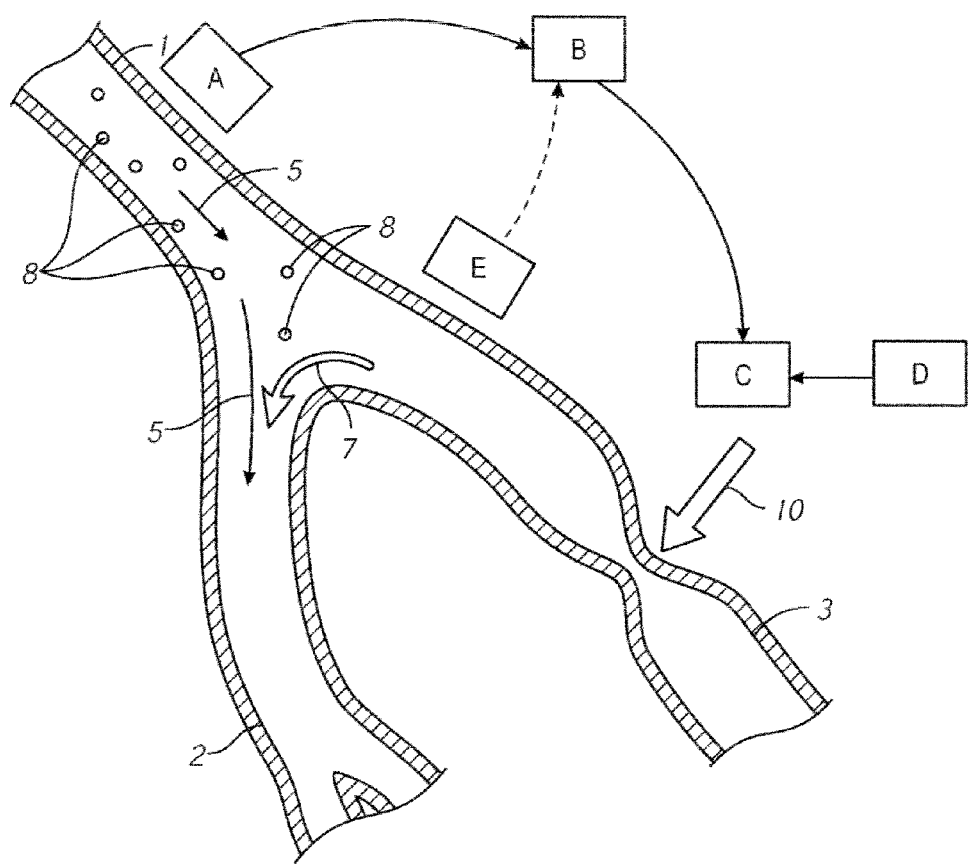
Figure 7:
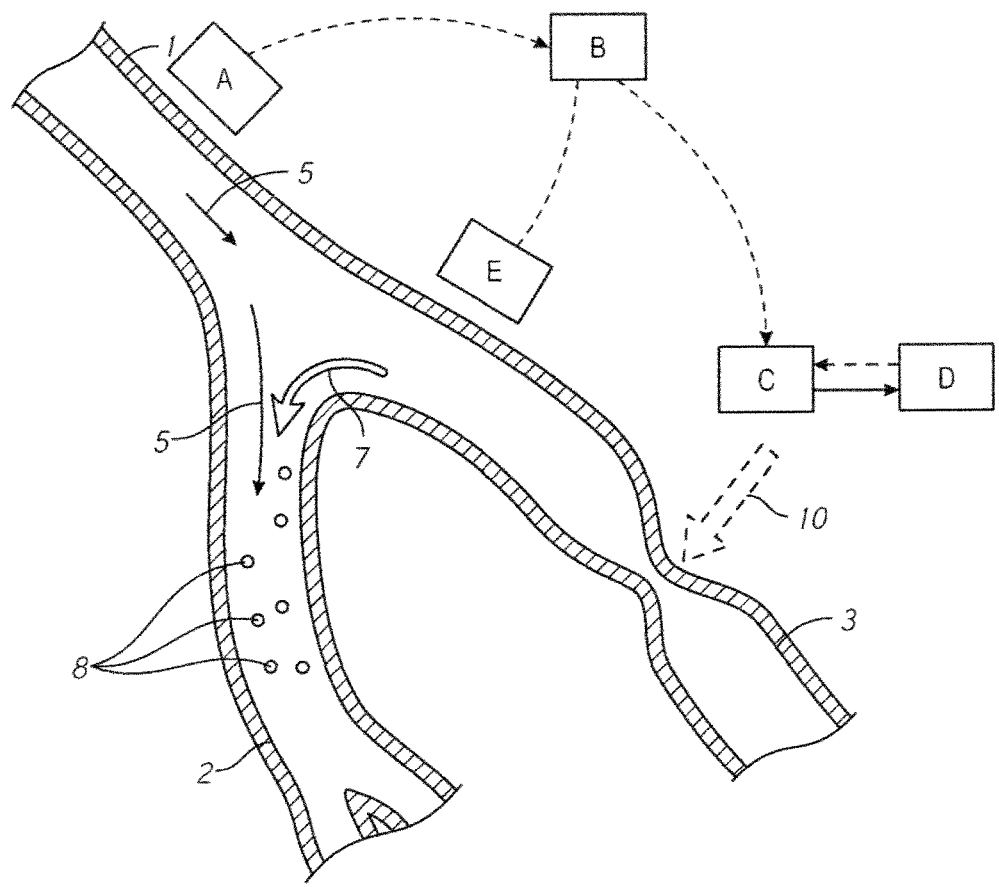
FIG. 7 shows an example of a release of arterial compression once embolic particles are diverted away from an organ to be protected on the basis of a negative feedback mechanism, triggered by disappearance of embolic particles in an afferent vascular pathway, excessive time or length of compression, or other parameters.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

The subject technology relates to prevention of emboli and ischemic injury (such as ischemia and stroke) as a consequence of an emboligenic event and/or intervention, e.g., on the heart, heart valves, coronary arteries and aorta. The subject technology provides for a device for safe and effective compression of a blood vessel, such as a carotid and/or vertebral artery, by providing one or more compression members having an anatomically congruent cross-sectional shape, size, and/or configuration. The subject technology also provides for a device for compression of a blood vessel, such as a carotid and/or vertebral artery, that has one or more compression members that are self-adjustable and allow precise positioning in an anatomical groove where a vessel, such as an artery, is located. The subject technology also provides a method of preventing arterial embolization by diverting emboli from a circulation to be protected, such as cerebral circulation, arm circulation, leg circulation or else.

Reference will now be made in detail to example embodiments of the subject technology, one or more examples of which are illustrated in the drawings. Each example is provided by way of explanation of the subject technology, and not meant as a limitation of the subject technology. For example, features illustrated or described as part of one embodiment can be used with another embodiment to yield still a third embodiment. It is intended that the present subject technology include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The subject technology provides for a device for safe and effective compression of a blood vessel, such as a carotid and/or vertebral artery, by providing one or more compression members having an anatomically congruent cross-sectional shape. The subject technology also provides for a device for compression of a blood vessel, such as a carotid and/or vertebral artery, that has one or more compression members that are self-adjustable and allow precise positioning in an anatomical groove where a vessel, such as an artery, is located. The subject technology also provides a method of preventing arterial embolization by diverting emboli from a circulation to be protected, such as cerebral circulation, arm circulation, leg circulation or else.

In some embodiments, the one or more compression members of the device can have a cross-sectional shape and/or size based on a specific location of an artery in a neck, such as in a neck triangle and/or in a groove between a trachea and/or longus colli muscle medially and a muscle, such as a sternocleidomastoid or scalenus anterior muscle laterally. By using different cross-sectional shapes and/or sizes of compression members, the members can be actuated so as to enter a groove in the neck and effectively reach a blood vessel, such as an artery, to be compressed. As a result, selective compression of a blood vessel, such as an artery, can be achieved without compromising adjacent organs in the neck, such as a trachea. Such specifically configured actuation and compression helps to assure safety when compressing a blood vessel, such as a carotid and/or vertebral artery, and prevents atherosclerotic plaque from dislodging and inducing stroke.

With reference to FIG. 1, a schematic view of a branching vessel such an aortic arch is shown in which emboli 8 are transferred from the more proximal arterial trunk 1, such an ascending aorta, into more distal branches 2 and 3, such as carotid 16, vertebral 12, or subclavian 13 arteries causing ischemic injury to the organ they supply (such as stroke in the case of embolization of cerebral arteries).

FIG. 1 shows a hypothetical blood vessel 1 branching into the blood vessels 2 and 3. The antegrade flow 5 in the vessel 1 carries blood, containing emboligenic particles 8 to different areas in the human body, including an organ more vulnerable to ischemic injury (such as a brain, and in some embodiments, a lung or extremity)—via the blood vessel 3, and less vulnerable (such as soft tissues of less important areas)—via blood vessel 2. As shown in FIG. 1, the emboli 8 entering vessel 1 will follow the path of branching into the vessels 2 and 3 and will enter both vessels 2 and 3 proportionally to the magnitude of flow through these vessels. The more flow would occur via the blood vessel 2, the more emboli will enter the organ to be protected (such as a brain) leading to serious ischemic injury (such as stroke).

To protect an organ (such as a brain) from embolization and ischemic injury (such as stroke), it is important to deflect emboli from the organ. Multiple invasive techniques have been attempted to deflect emboli from an organ at risk. For example, deflection of emboli has been attempted using intravascular traps, filters, and deflectors. These devices, besides being very complicated, involve introduction of additional hardware into a patient's circulation with unavoidable trauma to the vessel wall, disturbance of atherosclerotic plaque, and further embolization and stroke.

This can be avoided by external compression of the blood vessels supplying the organ at risk. Multiple devices for external compression of arteries of extremities of a human have been created, all of which are based on the general principle of a tourniquet or a diffuse pressure principle. However, this inevitably leads to compression of not only the artery, but also the tissues and organs surrounding the artery. As a result, these devices are not suitable for compression of the carotid and vertebral arteries due to the unique anatomy of the human neck, where the arteries are located deeply in anatomical grooves where they are difficult to reach. Moreover, these arteries are surrounded by multiple vital structures, such as the trachea, esophagus, brachial plexus, jugular vein, and cervical spine. Uniform nonspecific circular or other wide area compression of the structures of the neck can lead to serious organ injury and death, or other complications such as asphyxia, trauma to the tracheal cartilages, and/or compromise of the tracheal lumen without achieving a desired amount of carotid compression. If a high pressure is applied to overcome the resistance of the structures of the neck and compress the carotid and/or vertebral arteries in their anatomical grooves, there is a high risk of injury to the carotid and/or vertebral arteries with potential intravascular thrombosis, emboli and stroke, compression of jugular veins with brain edema, trauma to the trachea, and other drastic complications.

Examples of devices and methods for diverting emboli from circulation in a patient are described in U.S. patent application Ser. No. 11/859,235, which published as U.S. Patent Application Publication No. 2013/0304111, U.S. patent application Ser. No. 14/261,565, which published as U.S. Patent Application Publication No. 2014/0236221, and U.S. patent application Ser. No. 14/703,669, which published as U.S. Patent Application Publication No. 2015/0313607, each of the disclosures of which are hereby incorporated by reference herein in their entireties.

The device, method, and system disclosed herein provide a way of overcoming the aforementioned problems by providing anatomically sound, controlled, and brief compression of a blood vessel, such as a carotid and/or vertebral artery, while avoiding compression of the surrounding structures in the neck, such as the trachea, jugular veins, esophagus, brachial plexus, and spine. For example, a device with a set of compression members can provide for compression of carotid and/or vertebral arteries while avoiding compression of surrounding structures of the neck. A compression member, or a combination of compression members, can be have a cross-sectional shape and/or size for a particular neck anatomy. Thus, individual anatomic variations between patients can be accounted for, and a particular device and/or compression member(s) may be selected for use on a particular patient. Compression of the compression member(s) may cause the compression member(s) to self-center, spread tissue(s), and/or spare tissue(s) from compression and largely limit the area of compression to the carotid and/or vertebral artery.

Additionally, a method and system of using the device is provided, that induces temporary noninvasive external compression of the blood vessels supplying the organs at risk for embolic damage. The device can be actuated at a moment of emboligenic intervention and may be triggered and deactivated on demand and automatically on the basis of a patient's physiological parameters and/or detection of emboligenic particles.

Figure 13:
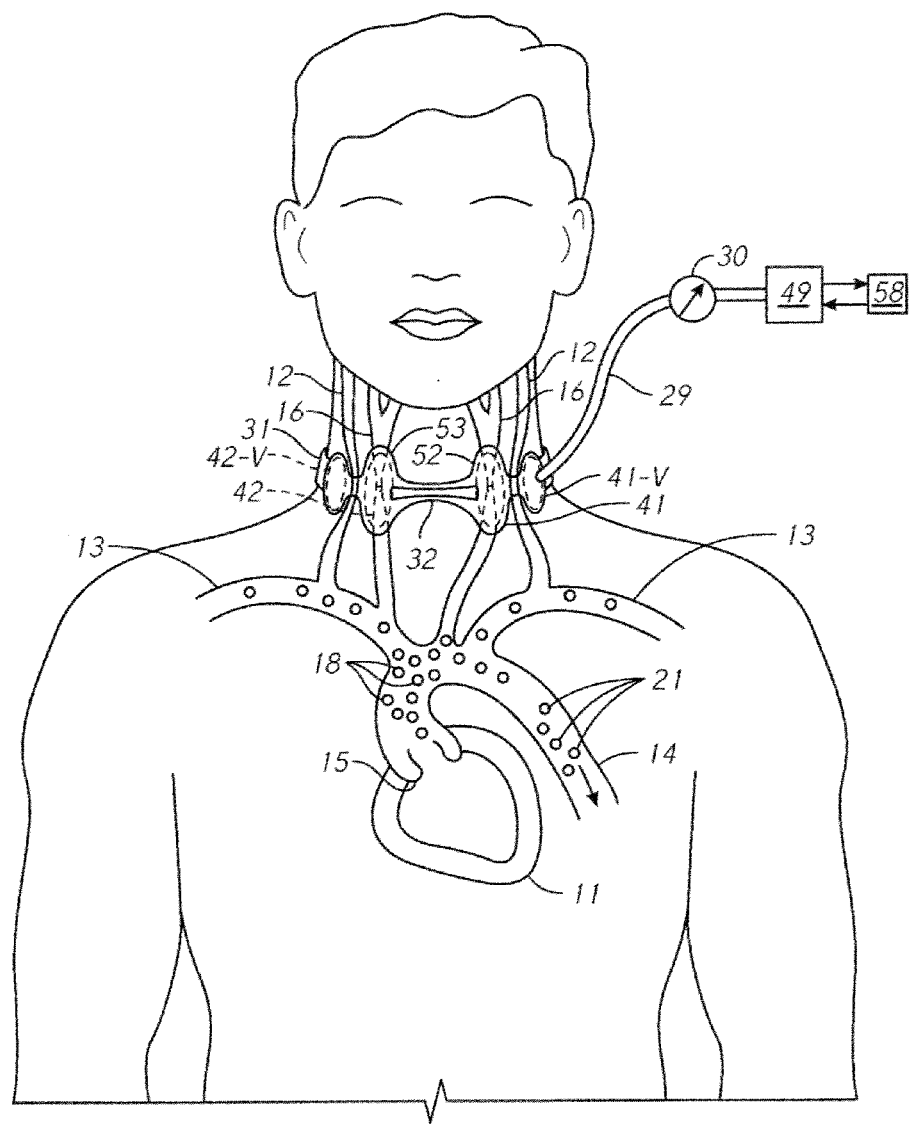
FIG. 13 is an example of a front view of a patient with external compression of carotid and/or vertebral arteries by virtue of an external compression device and mechanism, actuated by certain physiological parameters.

External compression may create a pressure gradient inside the blood vessel that precludes transgression of embolic particles into the particular vessel, and protects the organ that is supplied by the vessel. As illustrated in FIG. 13, bilateral compression of carotid and/or vertebral arteries at moments of embolic washout triggered during a cardiovascular procedure may protect the brain from incoming embolic particles by deflecting the particles into other, less vulnerable, areas of the human body.

FIGS. 2-7 show examples of a disclosed method of diverging emboli 8 from important structures such as a brain by exerting external pressure 10 on the blood vessel 3 (such as carotid or vertebral artery) to create an area of the pressure gradient 9 leading to limitation of the blood flow 5 carrying emboli 8 to the compressed blood vessel 3. Such compression will lead to flow reversal 7 diverting emboli 8 into other less important vessel 2. Acceleration of flow via the blood vessel 2 while the blood vessel 3 is compressed according to Bernoulli's principle will provide an additional force 7 deflecting the emboli 8 from the vessel 3 into the vessel 2. In order to avoid prolonged limitation of flow to the most important area of the human body (such as brain) the time of the protective compression of the blood vessel 2 should be brief. This goal is achieved by a disclosed method of vascular compression "on demand", i.e. at the brief periods of time when the emboligenic particles are released. As shown in FIGS. 3-7 the detectors of emboli "A" and/or "E" can be placed over the source of emboli (such as heart, heart valve, aorta, etc.) or the blood vessels 1 and 3, carrying said emboli to the target organ (such as brain). The appearance of emboli in said areas when detected as echogenic signal or as another physiological parameter(s), reflecting cardiac ejection and systole (such as EKG, arterial Doppler, pulse oximetry, arterial waveform etc.) will be recorded by monitor "B" and will actuate the compression mechanism "C" that would temporarily compress the blood vessel 3 leading to limitation, interruption and/or reversal of the flow to the organ to be protected. Detection can occur during and be sensitive to flight of emboli or other debris in transit within a blood vessel. The length of compression and its intensity will be recorded by monitoring system "D" with a capacity of overruling the act of compression if its length or intensity exceed the safe limit. Thus, positive and negative feedback mechanisms will be assured with a potential for an automated auto-regulatory function of such a device.

Once the emboli 8 disappear from the inflow vessel 1 and/or deflected from the blood vessel 3 into the blood vessel 2, the detectors "A" and/or "E" will signal such events to the device "B", that in turn will provide negative feedback to the device "C" thus interrupting the act of compression 10 and restoring circulation via the blood vessel 3 to the organ to be protected (such as brain). Considering the fact that the majority of embolic events leading to the organ damage and stroke in cardiovascular procedures are very short, this method and system are feasible and reliable, thus providing anti-embolic protection at the moments of surgery when the risk of embolism is maximal, while restoring circulation to such organs when the risk of embolism is minimal. The process of vascular compression alternating with vascular release can be repeated on multiple occasions throughout the course of cardiovascular procedure or a cardiac cycle.

Figure 8:
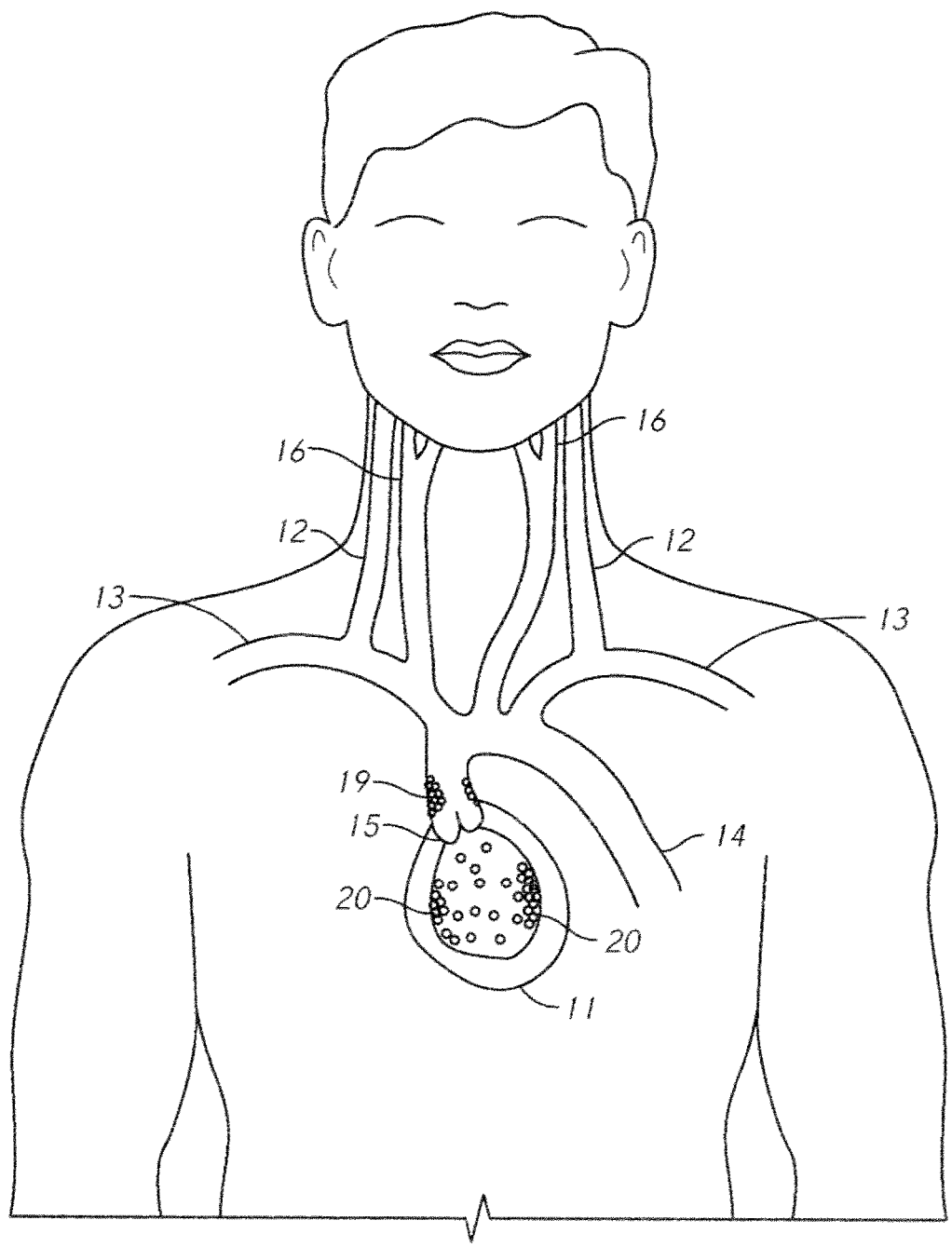
FIG. 8 is an example of a front view of a patient with embolic particles in the heart and ascending thoracic aorta with a potential for propagation into both carotid arteries and other vessels with the source of emboli being diseased aorta, aortic valve and/or the heart.

FIG. 8 illustrates a front view of a patient with embolic particles in the heart and ascending thoracic aorta with potential for propagation into both carotid arteries 16 and other blood vessels, such as vertebral arteries 12. The source of the emboli may be, for example, a diseased aorta, aortic valve 15, and/or heart 11.

Figure 9:
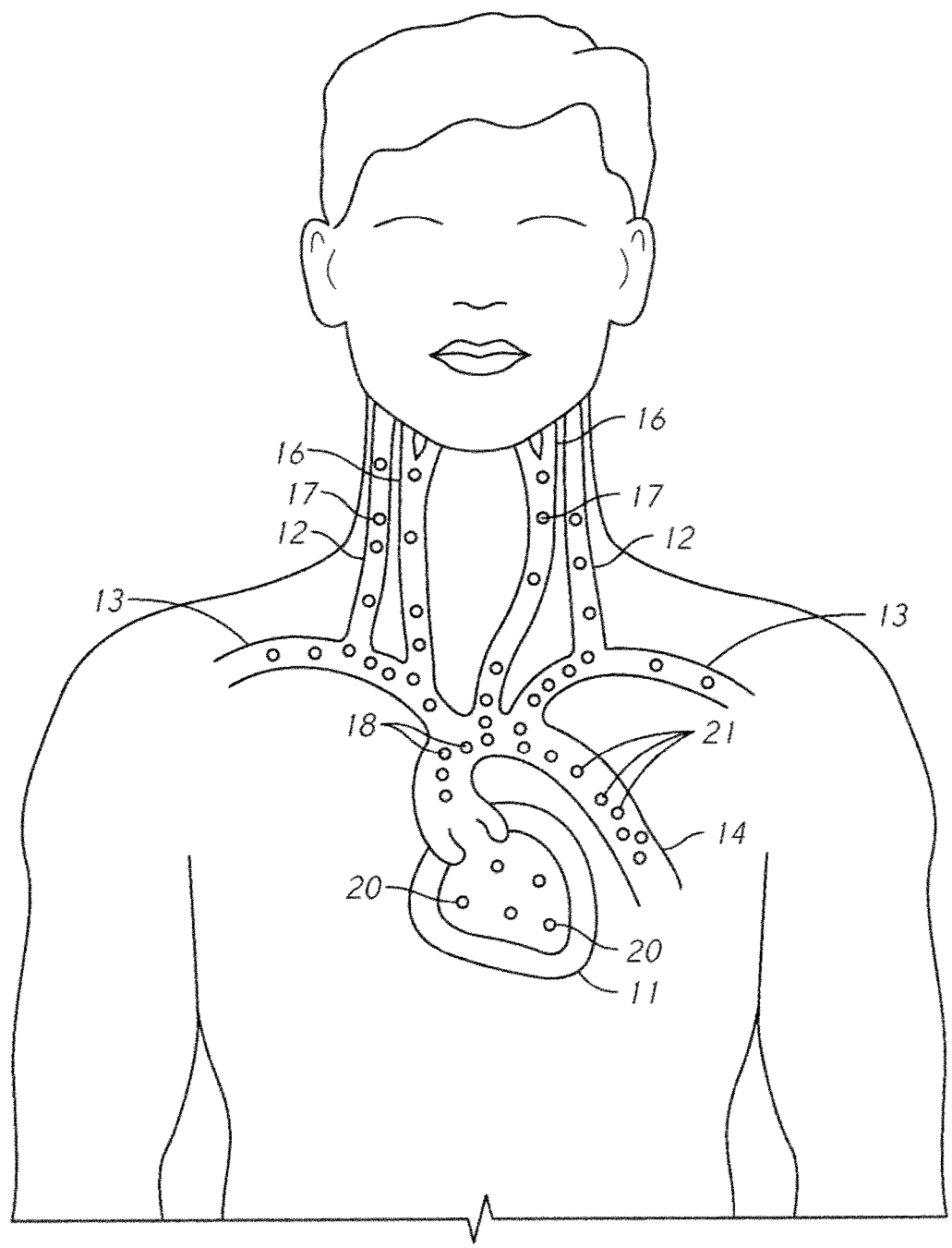
FIG. 9 is an example of a front view of a patient with release of embolic particles arising in the heart, aortic valve and/or aorta, into systemic circulation, including both carotid and vertebral arteries, and descending thoracic aorta.

The emboli 8 (FIG. 1) may be fragments of atherosclerotic plaque 19 (FIGS. 8, 9) of the ascending thoracic aorta that become dislodged during surgical or catheter manipulations on the aorta. Also shown in FIGS. 8 and 9 is calcification of the aortic valve 15 and intra-cardiac embolic particles 20 of the heart 11 that can also be the origin of emboli 17 eventually present in any artery such as the carotid artery 16 or vertebral artery 12. The intra-cardiac emboli 20 may include air, gas, thrombi and atherosclerotic materials. Although all of the various emboli in the heart 11, aorta and aortic valve 15 need not be present in all instances, they are all shown in FIGS. 8 and 9 for sake of example. Trauma to the heart 11, aortic valve 15 and aortic structures during placement and removal of items such as an aortic clamp, guidewire, catheter, balloon and/or an electrophysiological instrument can give rise to the presence of emboli 17 in the carotid arteries 16, vertebral arteries 12, and/or subclavian arteries 13. Additionally, a manipulation such as coronary artery bypass grafting, aortic and mitral valve replacement, catheter ablation, endovascular grafting of the aorta, percutaneous implantation of the aortic or mitral valves, endovascular manipulations on the aorta, aortic branches and the heart 11 may give rise to the presence of emboli 17 in the carotid arteries 16, vertebral arteries 12, and/or subclavian arteries 13. Critical moments of the aforementioned procedures (for example, during the aortic cross clamp manipulation, aortic valvuloplasty or valve implantation, coronary interventions, and/or endovascular procedures on the aorta) may cause emboli 17 to form and cause stroke and are referred to as emboligenic events.

The device, method, and system disclosed herein can also be applied for prevention of venous and/or pulmonary artery emboli. In this case the detection of the moving venous thrombus/embolus traveling from the peripheral vein toward the heart and pulmonary artery may initiate the measures for prevention of embolism by virtue of compression of the veins on its path, and signaling and initiating of other measures of prophylaxis of pulmonary embolism if necessary (such as deployment of the embolic trap or starting thrombolytic therapy). The detection of a moving thrombus/embolus can be achieved using a vascular Doppler technique, echocardiography or other methods.

A device, such as one of the example devices depicted in FIGS. 13-24, may be placed around the part of the body containing the target vessel that is noninvasive and can include a vascular compression member(s) 27 and/or 27-V applied to an area of an artery at a certain angle (ranging from 0 to 90) to an axis of the artery. The device may comprise a transverse vascular compression member 32. The members 27, 27-V and 32 can be converted from an unactuated state to an actuated state in which the members 27, 27-V and 32 create an area of compression 23 and 23-V at the target arteries such as carotid (16), vertebral (12), subclavian (13) or femoral or any other hypothetical vessel 2 to limit blood flow therethrough into the circulation to be protected such as cerebral or any other circulation. The members may have a particular shape and/or size, such as any of the shapes disclosed with reference to FIGS. 23-32, 35, and 37A. Emboli 8, 17, 18, 20 that are formed in the patient secondary to emboligenic intervention are diverted into a descending aorta 14 and other less important vascular structures.

Figure 10:
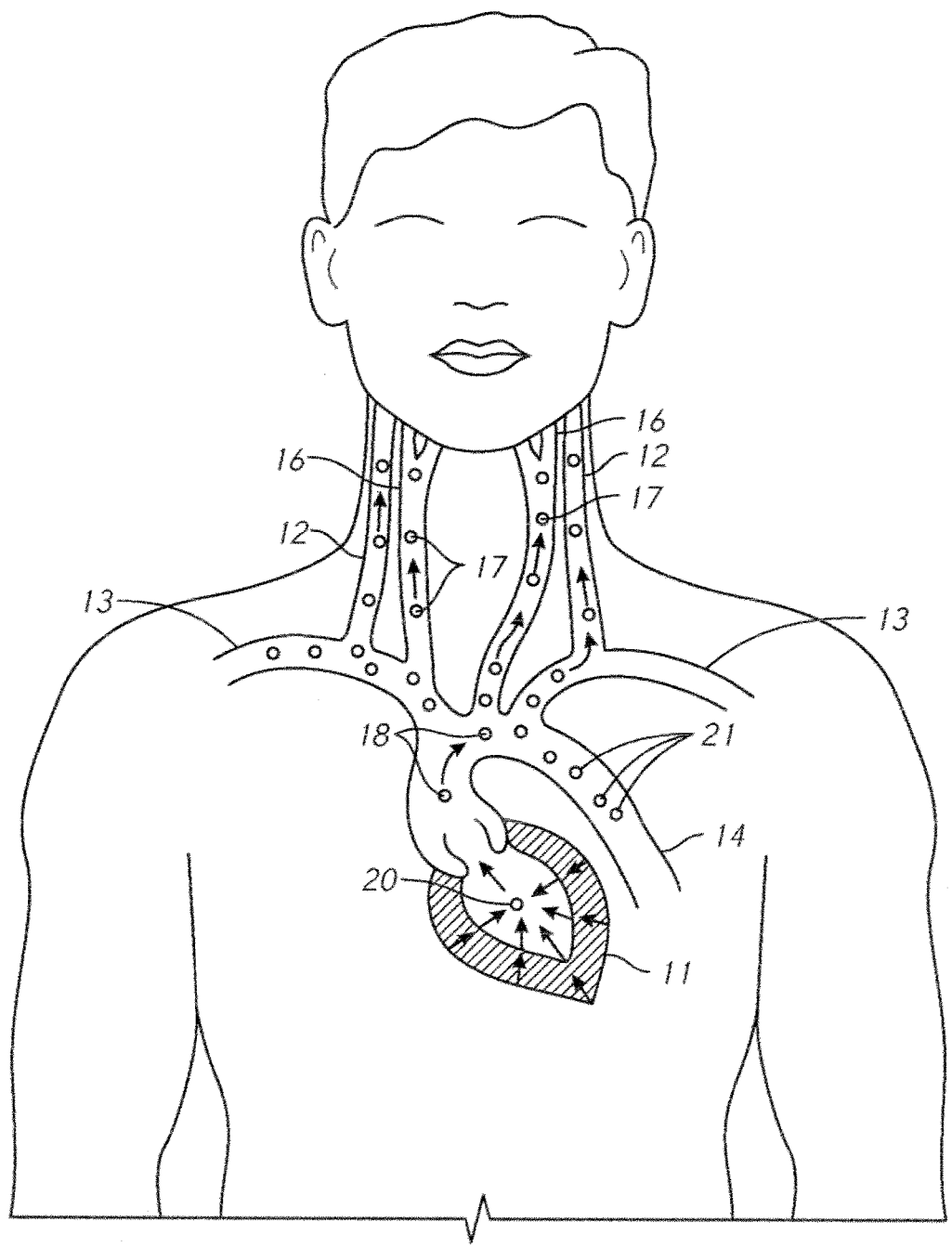
FIG. 10 shows an example of accentuation of a process of arterial embolization during cardiac contraction (systole).
Figure 11:
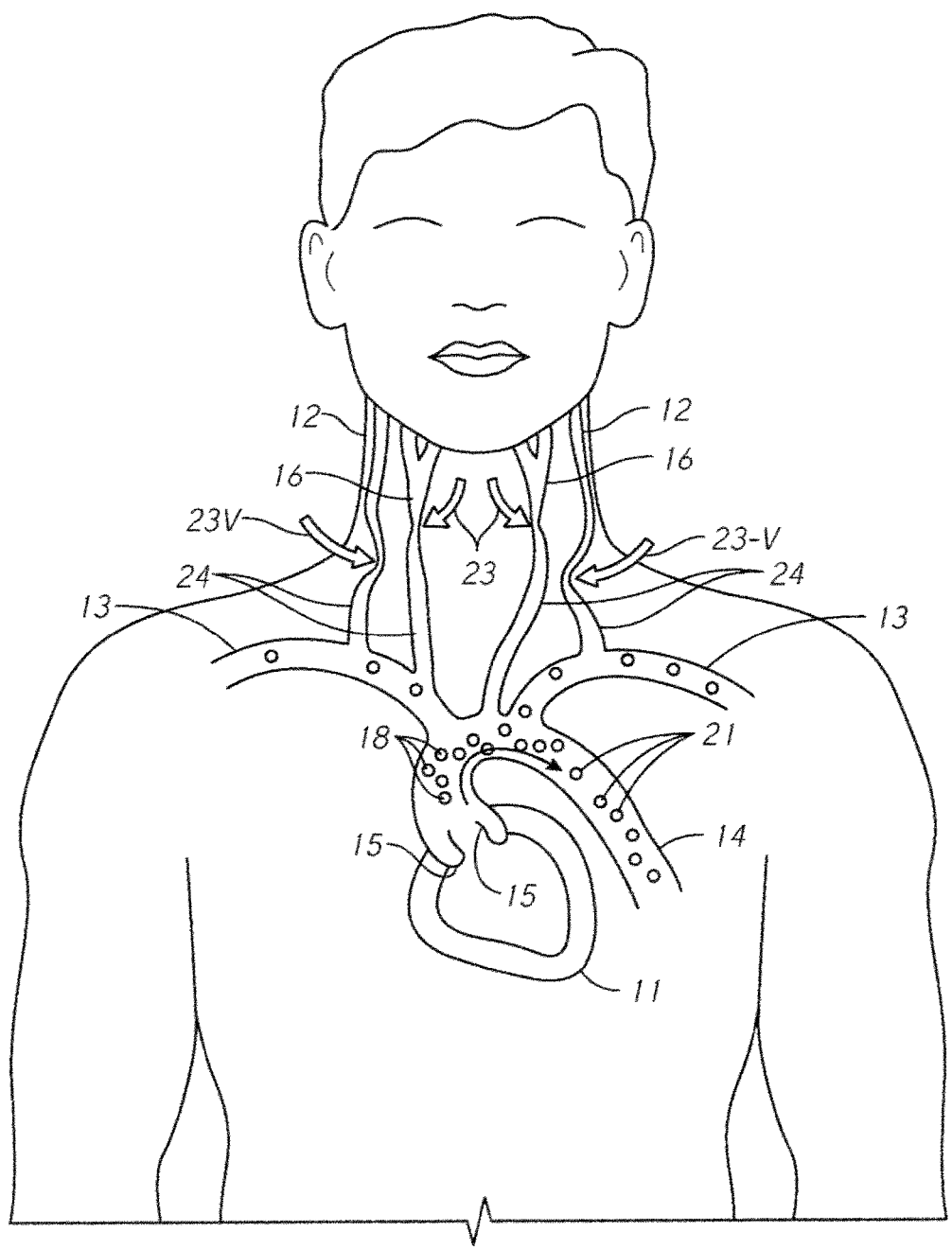
FIG. 11 is an example of a front view of a patient with external compression of both carotid and vertebral arteries that leads to temporary diminution or interruption of a cerebral arterial inflow, protecting a brain from potential emboli.
Figure 12:
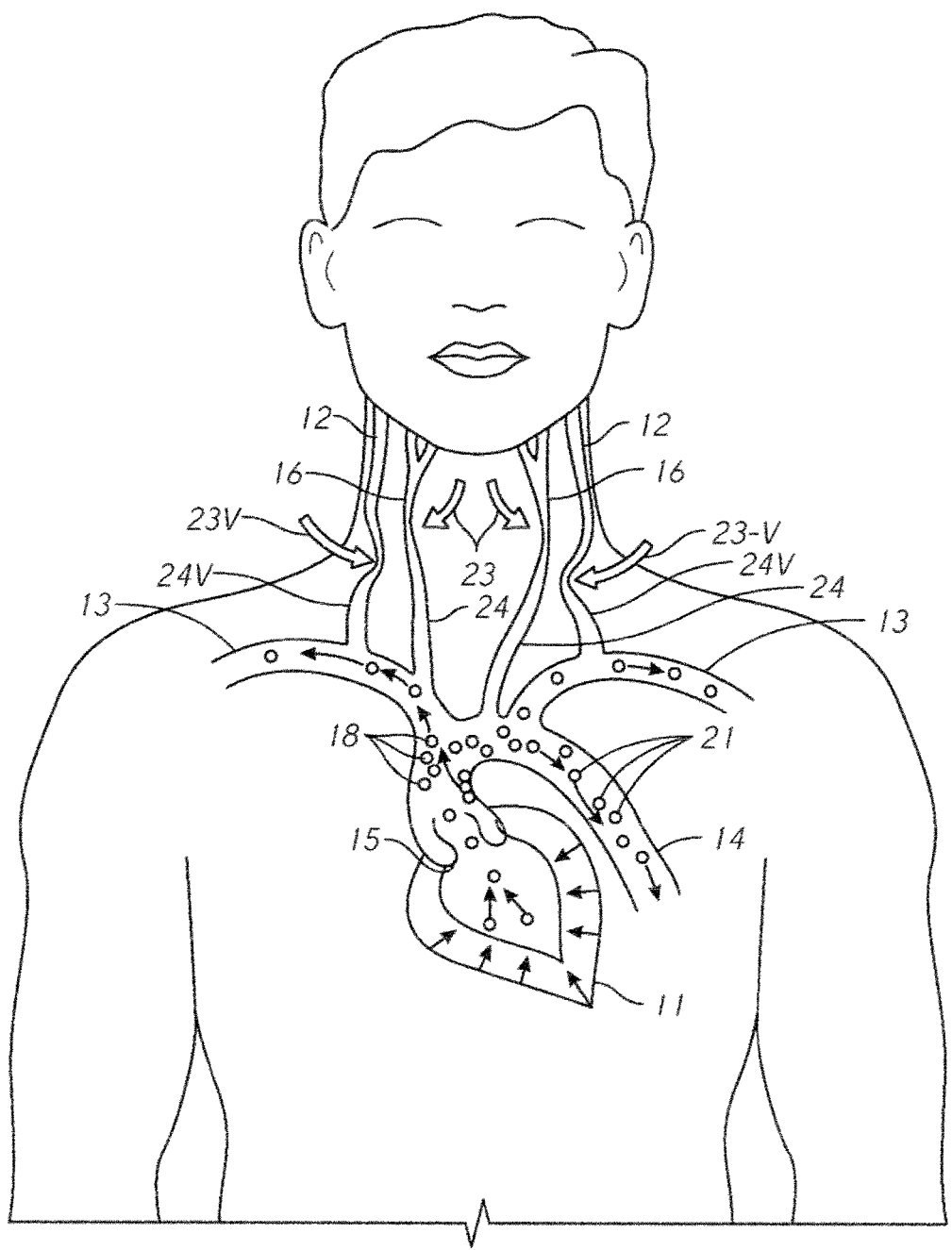
FIG. 12 is an example of a front view of a patient with external compression of both carotid and vertebral arteries during cardiac contraction.

As shown in FIG. 9 the emboligenic particles 18 and 20, formed in the heart 11, aortic valve 15 and aorta may enter the carotid arteries 16 and vertebral arteries 12, thus becoming cerebral emboli 17 leading to obstruction of cerebral circulation and stroke. As shown in FIG. 10, the degree of embolization may significantly increase at the time of cardiac contraction (systole) when intra-cardiac (20) and aortic (18) particles are forcefully ejected into the systemic circulation, leading to a massive entry of emboli 17 into the carotid 16 and vertebral 13 arteries. With respect to the method of anti-embolic protection disclosed above it is feasible to protect cerebral circulation by applying temporary pressure on the carotid and, if needed, vertebral arteries for a brief period of time when the risk of embolization is maximal (FIG. 11). Using detectors of potential emboligenic particles and emboli in the heart and aorta (by ECHO), aorta and its branches (as assessed by Doppler ultrasound) with timely signaling and immediate initiation of the protective compression of the target blood vessels such as carotid arteries 16 and/or vertebral arteries 12 will lead to temporary limitation of the blood inflow such as carotid and/or vertebral flow, thus protecting the organ, such as brain, from embolic load. Upon creation of the areas of vascular compression 23 (carotid) and 23-V (vertebral), a relative pressure gradient and a "no-flow" or "low-flow" condition is produced in the proximal segments of the compressed arteries such as carotid 16 and vertebral 12 arteries that prevents emboli 18 from entering the circulation to be protected such as cerebral circulation. The proximal carotid 16 and vertebral 12 arteries are areas of said arteries upstream from the areas of compression 23 and 23-V that have interrupted or diminished blood flow due to the compression. Potential cerebral vascular emboli such as emboli 18 are diverted into the more distal vessels such as descending aorta 14 and are illustrated as emboli 21. The thin arrow at the level of aortic arch on FIG. 11 shows preferential direction of the blood flow that carries potential emboli such as cerebral emboli 17 into the descending aorta 14 when the areas of compression 23 and 23-V are created. To protect the brain from an augmented embolic load at the time of cardiac systole (FIGS. 12 and 13) a method of carotid 16 and/or vertebral 12 compression synchronized with systolic phase of cardiac activity is disclosed. The compression system 49 (box C in FIG. 7) is actuated and deactuated by the device 58 (Box B in FIG. 7) depending on the phase of cardiac activity. Thus, the timing of the vascular compression 23 and 23-V in order to limit the inflow of emboli 17 can be triggered by electrophysiological, hemodynamic and/or pulse-oximetric indices of cardiac contraction, received and processed by the detector 58. On the other hand, the deactuation of the compression in order to restore arterial perfusion to the brain may be triggered by the same indices, but in the phase of cardiac relaxation.

FIGS. 13-16 disclose an exemplary embodiment that can selectively limit flow to either carotid 16 or vertebral arteries 12, or if necessary, limit flow to all or any combination of these vessels. Said device can be used to create the areas of compression 23 and 23-V as previously described to deflect emboli 18 and 20 from the target arteries such as carotid arteries 16 and vertebral arteries 13. The goal of this compression is to prevent the entry of emboli in the circulation to be protected such as cerebral circulation. The device can be positioned on the neck of the patient so that a pair of straps 33 and 43 extend around the neck of the patient and are secured to one another via hooks 44 and loops 45 that form a hook and loop type arrangement. However, it is to be understood that other mechanisms of securing the straps 33 and 43 to one another are possible and that the disclosed arrangement is only one exemplary embodiment. Securement of the hooks 44 and loops 45 causes the device 26 to be retained onto the body part such as the neck of the patient. This retention may be loose so that the device 26 has some room to give on the body part such as the neck, or the retention may be of a tightness that firmly secures the device into the body part such as the neck and prevents same from moving or twisting. The compression device may be a neck collar 26, combination of compression elements, bars, levers, pads, inserts and screws to provide compression of the target vessel in accordance with various exemplary embodiments. In other arrangements the compression device 26 may be a strap that lays on the front of the body part to be protected such as the neck of the patient, or may be made of multiple components that are not directly attached to one another but are positioned proximate to the neck of the patient. The device 26 may include two semi-oval halves that may be positioned around body part of the patient such as the neck or extremity of the patient in accordance with one exemplary embodiment. The device 26 need not be circular in cross-sectional shape. Even if the device 26 is not circular in cross-sectional shape it may still have a central axis 56 (FIG. 23A) as the central axis 56 can be located at the center of the vessel and the body part to be protected such as a carotid artery and the neck of the patient and thus may still be a central axis 56 of the device 26.

Figure 23A:
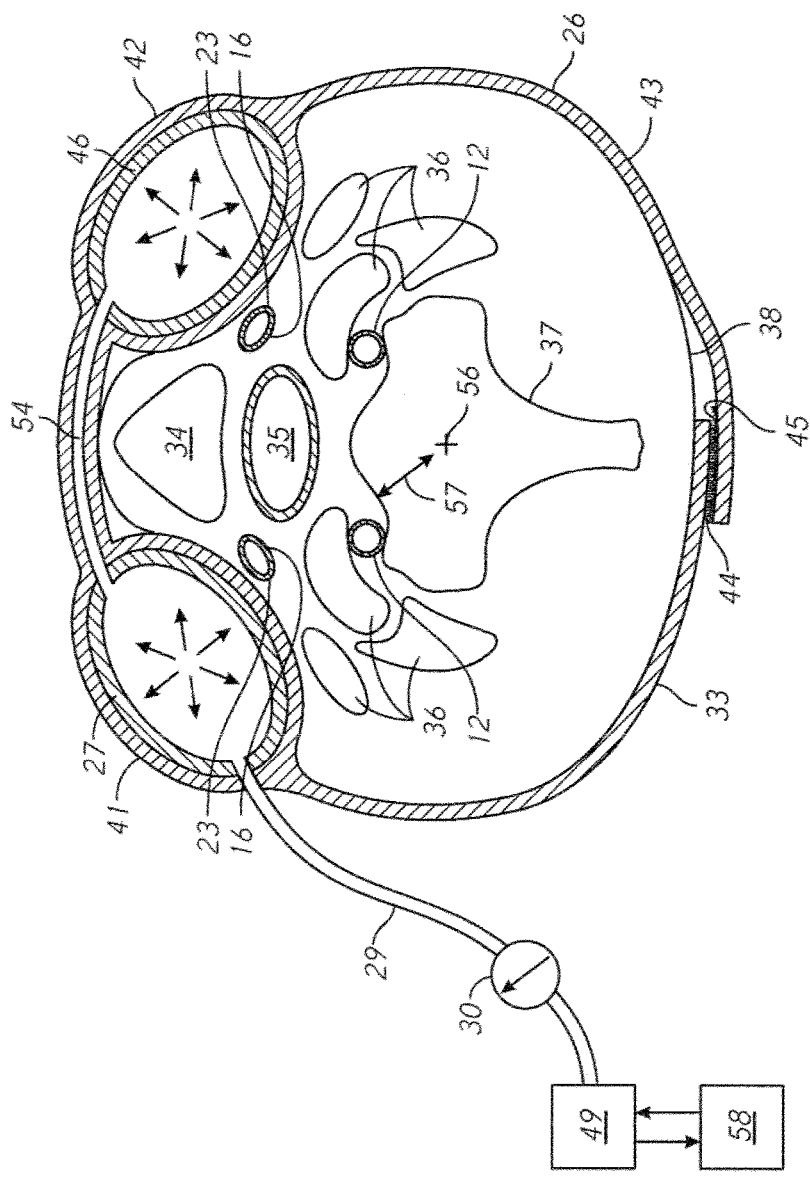
FIG. 23A is an example of a cross-sectional view of a neck of a patient and a device of FIG. 22 attached thereto in an actuated state with selective compression of carotid, but not vertebral arteries.
Figure 23B:
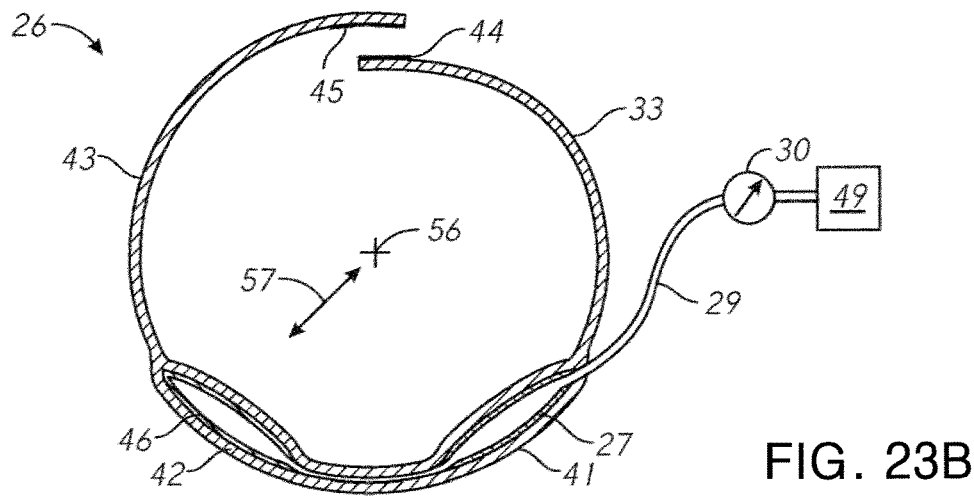
FIG. 23B is an example of a cross-sectional view of the device of FIG. 23A in a unactuated state.
Figure 23C:
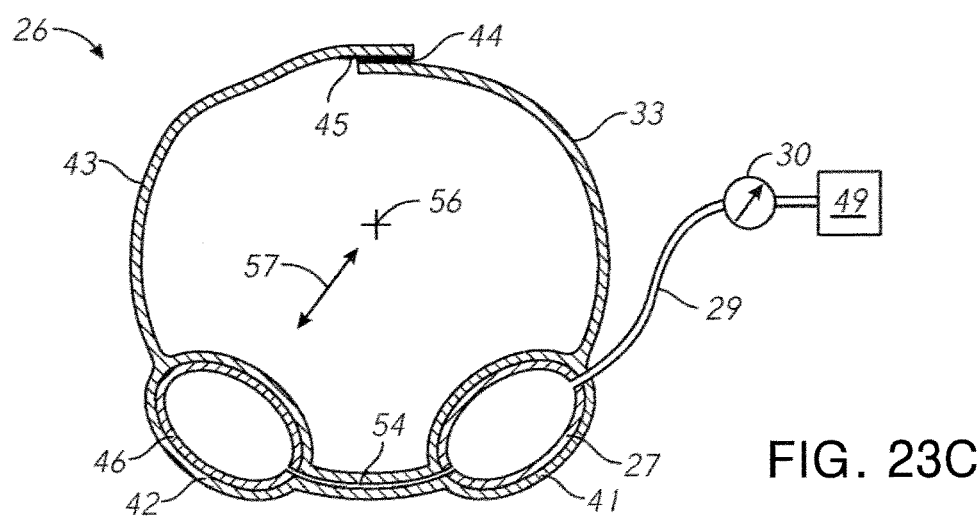
FIG. 23C is an example of a cross-sectional view of the device of FIG. 23A in an actuated state.
Figure 23D:
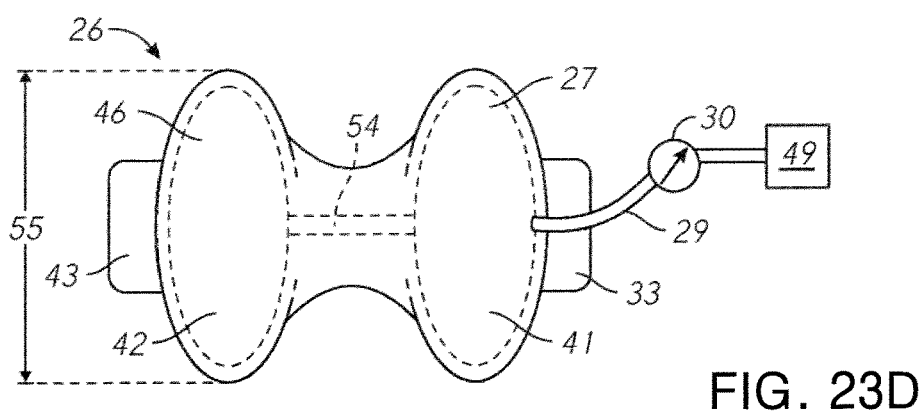
FIG. 23D is an example of a schematic view of the device of FIGS. 23A, 23B and 23C.

With reference in particular to FIGS. 23B, 23C and 23D, a pair of insertion pockets 41 and 42 are present on the device 26 and may be sealed at their tops and bottoms with respect to the vertical direction 55. As used herein, the vertical direction 55 may be the direction of the device 26 that is parallel to the direction of extension of the central axis 56. Strap 33 may extend from the first insertion pocket 41, and strap may extend from the second insertion pocket 42. The first insertion pocket 41 forms a cavity into which a first vascular compression member 27 is located. Member 27 is shown in a relaxed or unactuated state in FIG. 23B and may be made of a flexible material that can be stretched or otherwise deformed. A member 27 may be a compression member, such as any of the compression members described with reference to FIGS. 23-32, 35, and 37A. The material making up member 27 can be nonporous such that member 27 is capable of being filled with gas or liquid that enables the member 27 to expand and at the same time hold the gas or liquid therein. The member 27 may have a particular shape and/or size before and/or after being expanded. The pocket 41 may be made of a material that is different than the material making up member 27.

Figure 20:
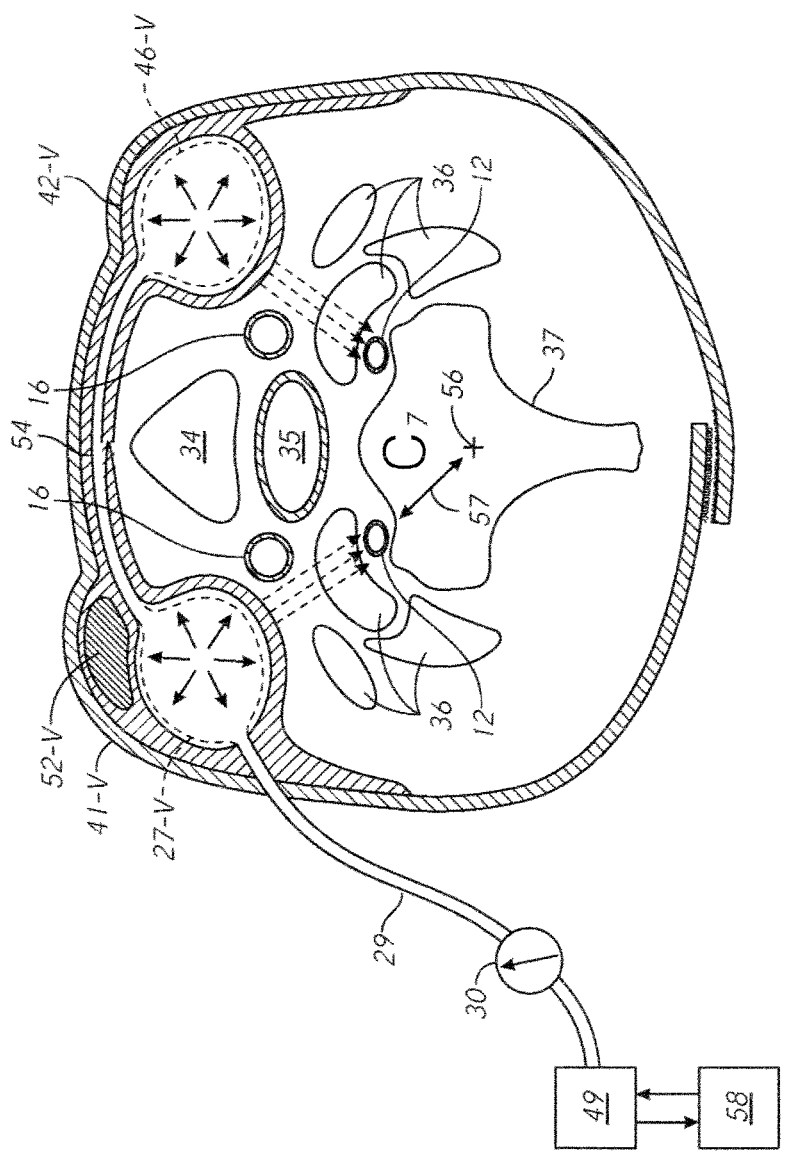
FIG. 20 is an example of a cross-sectional view of a neck of a patient and a device of FIGS. 18 and 19 for selective compression of vertebral arteries attached thereto in an actuated state with an option of a restrictive pad at an external surface of a compression member.
Figure 21A:
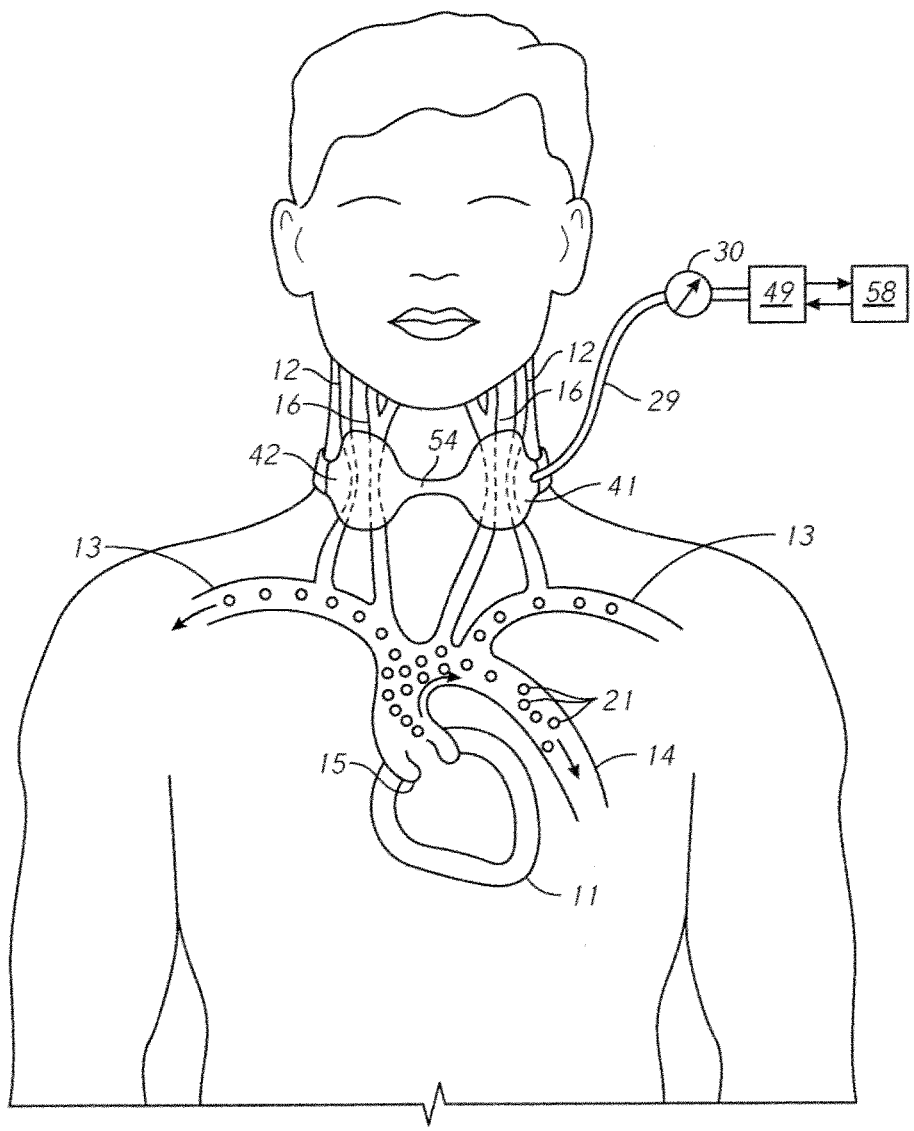
FIG. 21A is an example of a front view of a patient with a compression device in accordance with another exemplary embodiment.
Figure 21B:
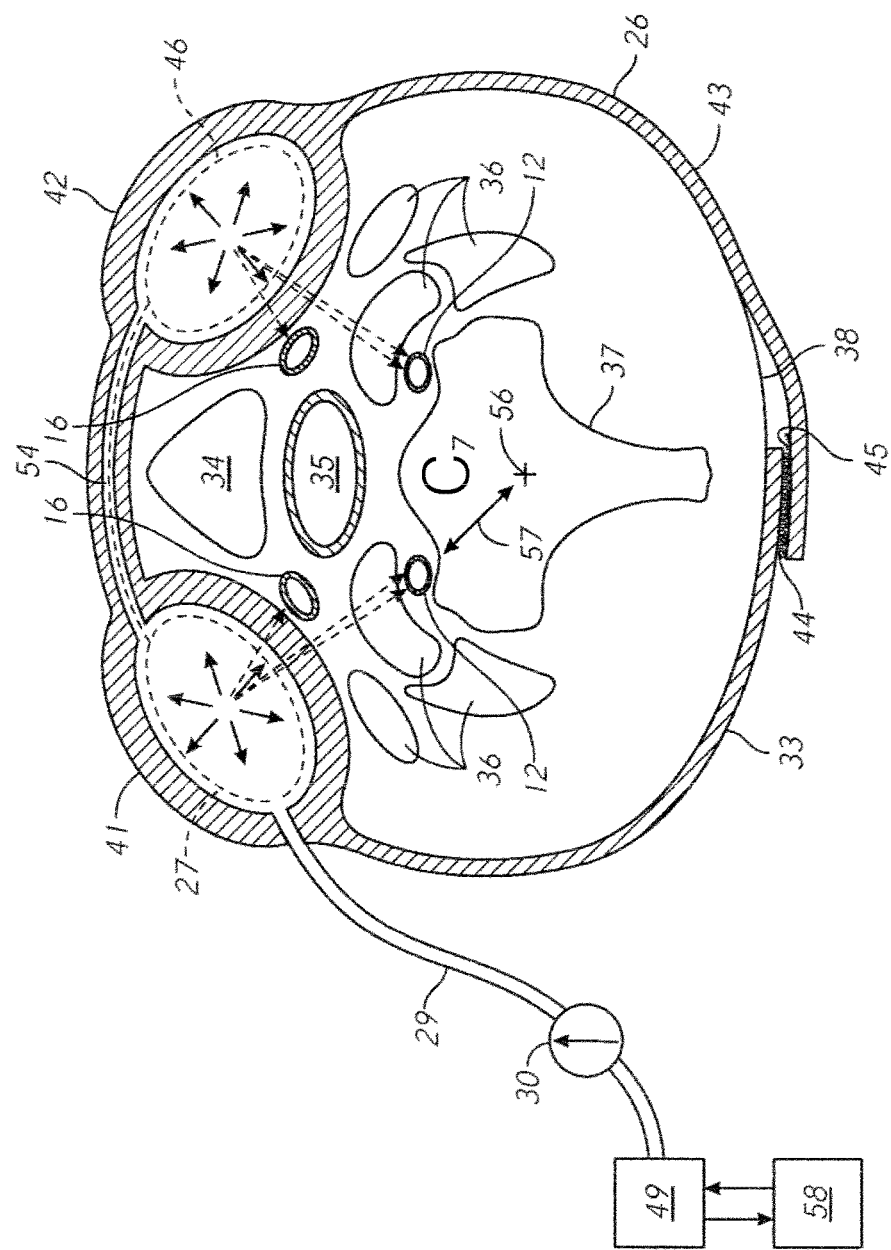
FIG. 21B is an example of a cross-sectional view of a neck of a patient and a device of FIG. 21A attached thereto in an actuated state when both carotid and vertebral arteries are compressed.
Figure 22:
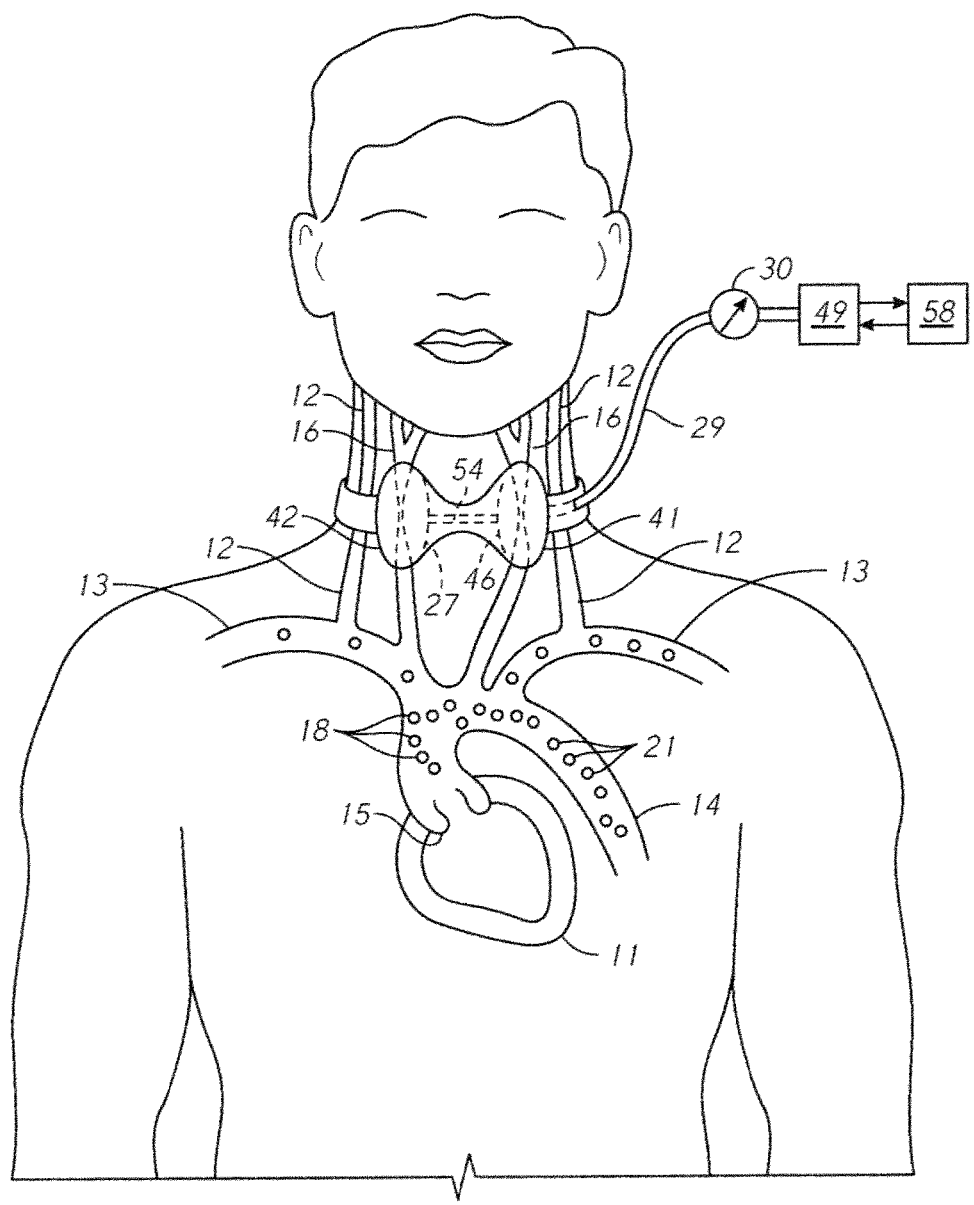
FIG. 22 is an example of a front view of a patient with another embodiment of the compression device, designed for selective compression of carotid arteries.

The second insertion pocket 42 forms a cavity into which the second vascular compression member 46 is retained. Member 46 may be configured in a manner similar to member 27 and a repeat of this information is not necessary. Member 46 may be completely sealed or connected to an opening that leads into connecting tube 54. Member 46 is in an unactuated state in FIG. 23B. Similarly, for compression of vertebral arteries 13 two insertion pockets 41-V and 42-V may be created. Said pockets may contain compression members 27-V and 46-V and other components to facilitate arterial compression as described in previous paragraphs. If necessary, only vertebral compression members can be actuated (FIG. 17). The specific anatomic location of the vertebral compression members is disclosed and should correspond to the level of the C4-C7 vertebra in order to assure adequate compression of the vertebral arteries 13 against the body of C-7 and in between the longus colli muscle medially and scalenus anterior and sternocleidomastoid muscle laterally (FIGS. 16 and 20). In other embodiments, however, only the carotid (FIGS. 22 and 23A) or, conversely, only vertebral (FIGS. 18-20) compression members could be present. Other arrangements and combinations of compression members are possible in order to achieve selective compression of any combination of the carotid and vertebral arteries. Some of these embodiments are shown on FIGS. 13-32, 35, and 37A.

A pressure or compression source 49 may be included and may be placed into communication with the first vascular compression member 27 by the way of tubing 29 that extends through a port of member 27. A manometer 30 may be included in the device 26 at some point between the member 27 and the pressure/compression source 49 in order to monitor and measure pressure in the system. A detector of emboli and/or EKG, pulse oximeter, arterial waveform monitor 58 can be bundled with the pressure source 49 to assure an option of initiation of the vascular compression once the potential emboli are ejected or anticipated. FIGS. 23C and 23D illustrate the device 26 once the pressure/compression source 49 is activated in order to cause the device 26 to be pressurized. The pressure source 49 may be a pump that injects air, gas or liquid, such as water, through the pressure tubing 29. Injection of air or otherwise increasing the pressure causes the first vascular compression member 27 to expand. Due to fluid communication through the connecting tube 54, the second vascular compression member 46 will likewise expand and the two members 27 and 46 may expand at the same rate to the same size. Expansion may be in the radial direction 57 such that the expandable members 27 and 46 expand towards the central axis 56 and away from the central axis 56. In some exemplary embodiments, the members 27 and 46 may expand in the radial direction 57 towards the central axis 56 but not in the radial direction 57 away from the central axis 56. This arrangement may be accomplished by making portions of the compression members 27 and 46, for example the portions facing away from the central axis 56 in the radial direction 57, such that they cannot expand while the portion facing towards the central axis 56 are in fact expandable. Said arrangements can be also applied to the vertebral compression elements 41-V, 42-V, 46-V and 27-V and their repetition of them is not necessary.

The compression members 27 and 46 as well as 27-V and 46-V may be inflated to a pressure level that is just above the level of the patient's arterial pressure to achieve temporary limitation or interruption of the arterial blood flow. The arteries to be protected such as both the left and right carotid arteries 16, left and right vertebral arteries 12, and if needed, femoral and brachial arteries can be compressed at the same time or separately and in any combination.

Additionally or alternatively, the insertion pockets 41, 42 and 41-V, 42-V could have portions that are made of different materials so that the parts facing the central axis 56 in the radial direction 57 are expandable while the parts facing away from the central axis 56 in the radial direction 57 are not expandable. The compression members 27, 27-V and 46, 46-V are elongated in the vertical direction 55, which is the same direction as the central axis 56. However, it may be the case that upon expansion of the expandable members 27, 27-V and 46, 46-V from the unactuated to the actuated states the expandable members 27, 27-V and 46, 46-V do not expand in the vertical direction 55. Moreover the compression members may not be expandable at all and may exert compression into the underlying vascular structure by virtue of tightening of their attachment apparatus or external straps.

The exemplary embodiment of the device 26 in FIGS. 23A-23D does not include a transverse vascular compression member 32 but instead includes only two compression members 46 that can be expandable. The device 26 may be placed onto the patient so that the first longitudinal compression member 27 overlays the artery to be protected such as a carotid artery 16, or both carotid and vertebral artery 12 (FIGS. 21A and 21B) such that the artery is located between the central axis 56 and the member 27 in the radial direction 57. However, other arteries such as subclavian, or femoral and brachial artery can be compressed in a similar manner. If needed second vascular compression member 46 and 46-V may be laid on top of the other artery such as carotid artery 16 and vertebral artery 12, such that the second artery is likewise between the member 46 and 46-V and the central axis 56 in the radial direction 57. Expansion forces of the expandable members 27 and 46 and 27-V, 46-V or the outer compression forces on non-expandable or partially expandable members 27, 27-V and 46, 46-V may be imparted onto the target arteries such as carotid arteries 16 and vertebral arteries 12 so that they are compressed thus forming the areas of compression 23 and 23-V as previously discussed. The pressure at the compression members 27, 27-V and 46, 46-V may be set so as to exceed the patient's systemic pressure to achieve adequate compression of the carotid arteries 16 and vertebral arteries 12 to have a transient "no-flow" or "low-flow" effect. In some arrangements the pressure of the members 27, 27-V, 32 and/or 46, 46-V may exceed the patient's systemic pressure by 10-20 mm Hg, or up to 30 mm Hg and even higher in accordance with certain exemplary embodiments. Once the emboligenic part of the procedure is completed, the pressure in members 27 and 46 may be released in order to establish adequate arterial flow, such as carotid, brachial or femoral arterial flow. The release of pressure can also be triggered by disappearance of embolic particles in the heart chambers (as detected by cardiac ECHO), aorta (as detected by arterial Doppler), carotid and cerebral arteries (as detected by carotid Doppler ultrasound and transcranial Doppler) and by the indices of cardiac relaxation (diastole) as reflected by EKG, pulse oximetry, arterial pressure waveform and other indices.

An automated self-regulating compression-relaxation mechanism or system is thus possible, allowing for real-time monitoring and anti-embolic protection during cardiovascular interventions. Such mechanism or system would include the elements A, B, C, D and E as depicted in FIGS. 1-6 with a feature of a fully automated vascular compression-relaxation depending on the embolic load and the phase of cardiac cycle.

Another exemplary embodiment of the device 26 is illustrated in FIGS. 24A-24D. The device 26 in this exemplary embodiment also functions to compress the carotid arteries 16 to create the areas of compression 23. The device 26 includes a first insertion pocket 41 and a second insertion pocket 42 but lacks first and second vascular compression members 27 and 46. Instead a first compression member 52 is located within the first insertion pocket 41, and a second compression member 53 is located within the second insertion pocket 42. The compression members 52 and 53 are not expandable but may be made of a material, such as foam, that can be compressed and then can subsequently expand back into its original shape. The compression members 52 and 53 may alternatively be made of a material that does not exhibit any give upon the application of forces thereto that would be encountered in a procedure of the type described herein. The compression members 52 and 53 may be elongated in the vertical direction 55 and may have a convex shape that faces the central axis 56. The shape of the compression members 52 and 53 at their surfaces that face away from the central axis 56 in the radial direction 57 may be different than those that face towards the central axis 56. In some embodiments, the compression members may have a cross-sectional shape and/or size that corresponds to any of the compression members illustrated in FIG. 24, 25-32, 35, or 37A.

The device 26 may include a transverse carotid compression section 31 that is located outward from the compression members 52 and 53 in the radial direction 57 from the central axis 56. A transverse carotid expandable member 32 may be held by the section 31 and can have an arc length about the central axis 56 that extends beyond both of the compression members 52 and 53. The transverse carotid expandable member 32 has a height in the vertical direction 55 that is the same as, larger or smaller than the height of the compression members 52 and 53 in the vertical direction 55.

The member 32 is made of a material that will hold air, gas or liquid such that it can be expanded upon the application of fluid thereto. The member 32 has a single port that is in fluid communication with the pressure tubing 29. Application of pressure to the member 32 will cause the member 32 to expand as shown for example in FIGS. 24C and 24D. In some embodiments the member 32 can be partially or completely deflated, removed and not present so that only the expandable members 27, 32 and/or members 52 and 53 are present to compress the carotid arteries 16 and/or vertebral arteries 12. In other embodiments, the compression members 52 and 53 can be removed and not present so that only the expandable member 32 is present to compress the carotid arteries 16.

The transverse carotid compression section 31 can be arranged so that all of it is expandable or so that only a portion of it expands as the member 32 expands. Boundary lines 50 and 51 may demarcate areas of the transverse carotid compression section 31 that can expand from those that cannot expand. For example, the portion of section 31 radially outward from the boundary lines 50 and 51 may not be capable of expansion while the portions of section 31 radially inward from boundary lines 50 and 51 are capable of stretching and thus expanding or contracting. This arrangement may cause expansion only, or primarily, in the radially inward direction upon expansion of the expandable member 32. In other embodiments, the section 31 is made of the same material and exhibits expansibility such that it generally expands in all directions equally. The expandable member 32 may be arranged so that it does not lengthen in the vertical direction 55 upon expansion, or in some arrangements only minimally expands in the vertical direction 55 when actuated.

Placement of the device 26 onto the patient may result in the first compression member 52 overlaying the target artery such as carotid artery 16 femoral or brachial artery so that the artery to be compressed is between compression member 52 and the central axis 56 in the radial direction 57. The second compression member 52 will be arranged so that it overlays the second carotid artery 16 causing it to be between the second compression member 52 and the central axis 56 in the radial direction 57. The expandable members 27, 32 and 46 may be located at the neck, upper chest, shoulder, lower abdomen or an extremity of the patient such that they are secured to the neck or extremity or otherwise proximate. The compression members 27, 32 and 46 need not be in direct contact with the body part of the patient such as the neck, chest, abdomen or extremity but only located near them. Application of pressure via the pressure source 49 causes the transverse compression member 32 that may be expandable to exert pressure in the radial direction 57. This inward radial pressure causes the compression members 52 and 53 to move inwards and be urged against the target vessels such as carotid arteries 16, femoral, brachial or other compressible arteries or veins. The positioning and configuration of the members 52 and 53 function to impart compressive forces onto the arteries to be compressed such as carotid arteries 16, femoral, brachial or other arteries when the device 26 is pressurized thus resulting in the creation of the areas of compression 23. The other components of the device 26 may be made as those previously described and a repeat of this information is not necessary.

Although described as lacking first and second longitudinal vascular compression members 27 and 46, an alternative arrangement may be made in which these members 27 and 46 are present. In such an arrangement, the expandable members 27 and 46 may expand in order to press the compression members 52 and 53 towards the arteries to be compressed such as carotid arteries 16, femoral, brachial or other compressible arteries.

Moreover, it can also be arranged for compression of the vertebral arteries 12, or both vertebral 12 and carotid 16 arteries by adding additional compression members in the same arrangement as described above.

Another exemplary embodiment of the device 26 is one in which a pair of longitudinal vascular compression members 27 and 46 are present along with a transverse vascular compression member 32. A pair of compression members 52 and 53 may be missing from this embodiment, or they may be present in certain arrangements. This exemplary embodiment may include additional pressure tube lines 47 and 48 that are separate from pressure tubing 29 that actuates the transverse vascular compression member such as carotid compression member 32. Pressure tube lines 47 and 48 provide pressure to the first and second longitudinal vascular compression members 27 and 46 so that these members 27 and 46 can be actuated at different rates, amounts, and/or times than compression member 32. This flexibility provides selective pressure adjustments between the transverse vascular compression member 32 and longitudinal vascular compression members such as carotid members 27 and 46. This feature will provide an option to decrease or completely eliminate the degree of circumferential compression of the body part such as the neck or extremity when selective inflation of the longitudinal vascular compression members is adequate. Conversely, if inflation of longitudinal compression members such as carotid members 27 and 46 does not lead to sufficient reduction of the arterial flow, an additional inflation of the transverse vascular compression member such as carotid member 32 would allow one to achieve the desired effect by combining the effect of pressure created in all of the members described.

The preferred method of an arterial compression in this case, for example—compression of the carotid and vertebral arteries, will be an initial inflation of longitudinal members 27 and 46, followed by inflation of member 32 when necessary. The degree of interruption of the arterial flow in this and other embodiments can be checked by the data of arterial Doppler, distal pulsation and oximetry as wells as other techniques of assessment of distal perfusion. The other components of the device 26 are the same as those previously disclosed with respect to other embodiments and a repeat of this information is not necessary.

An alternative exemplary embodiment of the device 26 that is being disclosed is similar to that previously disclosed with respect to FIGS. 23 and 24A-D and a repeat of the features and functionality that are similar between the two need not be repeated. The pressurization of the members 27, 32 and 46 are different in that the second pressure tube 47 feeds into the first longitudinal vascular compression member 27, and in that the third pressure tube 48 supplies the second longitudinal vascular compression member 46 to allow the members 27 and 46 to be pressurized independently from one another. In this regard, one can apply more or less pressure to member 27 than member 46 so that compression of the arteries, such as carotid arteries 16 or femoral and brachial arteries can be more precisely controlled. The transverse vascular compression member 32 is supplied by pressure tubing 29 and is independent from the expansion of members 27 and 46 such that it can be pressurized to a greater or lesser extent than members 27 and 46. The manometer 30 may be capable of measuring pressures in all of the lines 29, 47 and 48 so that their individual pressures can be monitored. In use, one may adjust the pressures in members 27 and 46 first, then subsequently if needed one may apply pressure into member 32 to cause its actuation so that adequate compression of the carotid arteries 16 is realized. In some instances, however, member 32 can be partially or completely deflated, removed and not present.

The ports for the pressure lines 47 and 48 may be located at the bottom of the expandable members 27 and 46 in the vertical direction 55. However, the ports for pressure lines 47 and 48 need not be in the disclosed locations in accordance with other exemplary embodiments and may be above the transverse carotid compression section 31 or at the same location as the section 31 in the vertical direction 55 in other exemplary embodiments. The insertion pockets 41 and 42 although described as being sealed may have an opening into which the expandable members 27 and 46 may be removed and into which first and/or second compression members 52 and 53 may be inserted so that the device 26 can function with the compression members 52 and 53 and transverse carotid expandable member 32 as previously discussed.

The arrangement of the device 26 in this case includes a pair of longitudinal vascular compression members 27 and 46 along with a transverse vascular compression member 32. The circumferential distance about the central axis 56 may be the circumferential distance about the neck or extremity of the patient when the device 26 is worn by a patient and thus these two terms can be interchangeable when discussing the arc length of the member 32. In other exemplary embodiments, the arc length of the member 32 may be from 50-65% (180 degrees-234 degrees) about the circumference of the body part of the patient, from 25%-50% (90 degrees-180 degrees) about the circumference of the body part patient, or from 15%-25% (54 degrees-90 degrees) about the circumference of the body part of the patient. In yet other exemplary embodiments, the member 32 may extend 360 degrees completely about the body part of the patient.

The longitudinal vascular compression member such as carotid compression members 27 and 46 are closer to the central axis 56 in the radial direction 57 than the transverse compression member 32 is to the central axis 56. Comparison of FIG. 6C and, using a device for compression of the carotid arteries as an example, demonstrates that the lengths of the members 27, 32 and 46 do not increase in the vertical direction 55, or in the arc length direction, upon moving from the unactuated orientation to the actuated orientation or only slightly expand in these directions upon actuation. The majority of the expansion may be in the radial direction 57 either towards the central axis 56 or away from the central axis 56 or a combination of the two. In other arrangements, however, expansion of the members 27, 32 and 46 may result in equal expansion in all directions. As previously stated, various components of the device 26 may be arranged and function in a manner similar to those as previously discussed and a repeat of this information is not necessary.

Figure 24A:
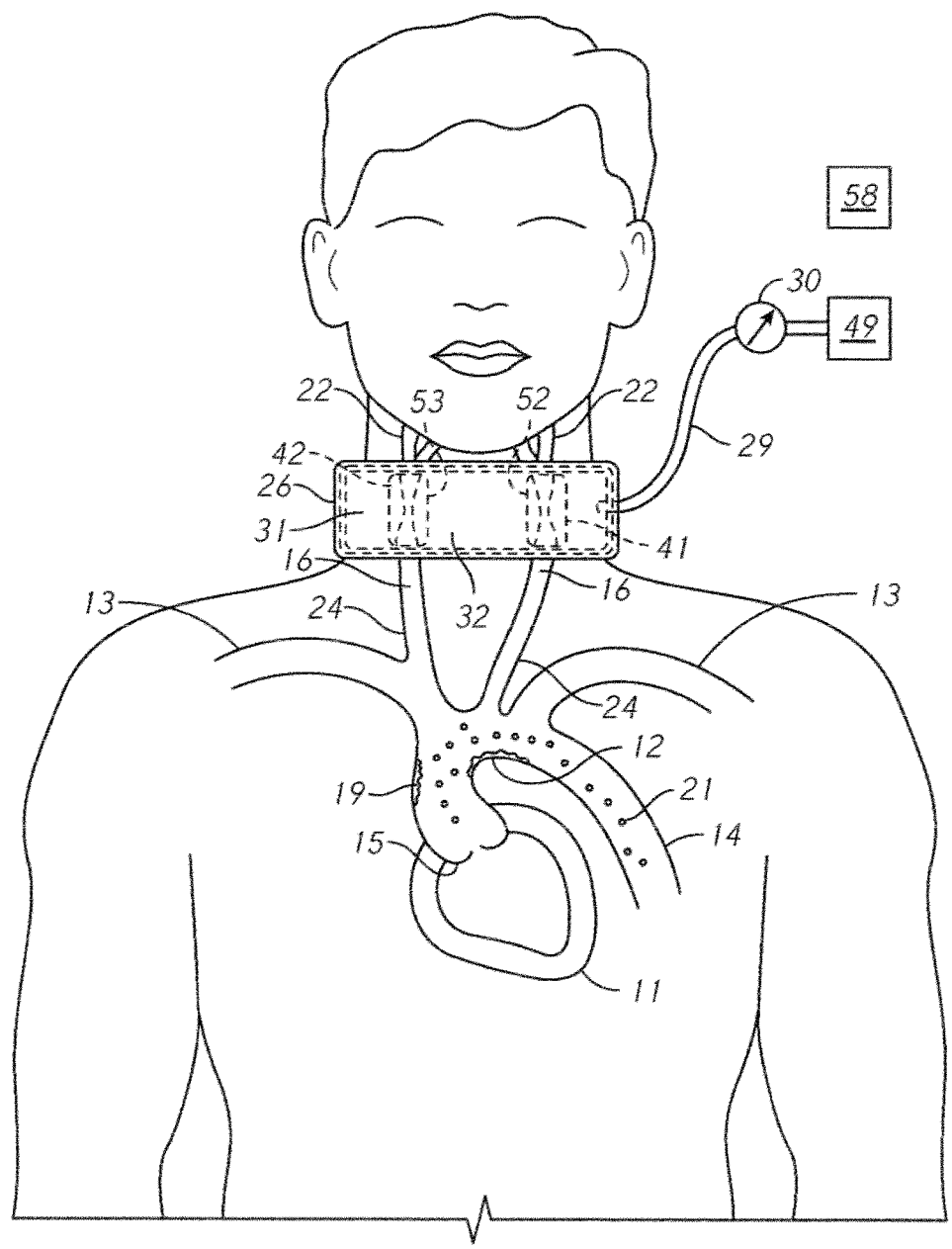
FIG. 24A is an example of a front view of a patient with yet another embodiment of the antiembolic compression device.
Figure 24B:
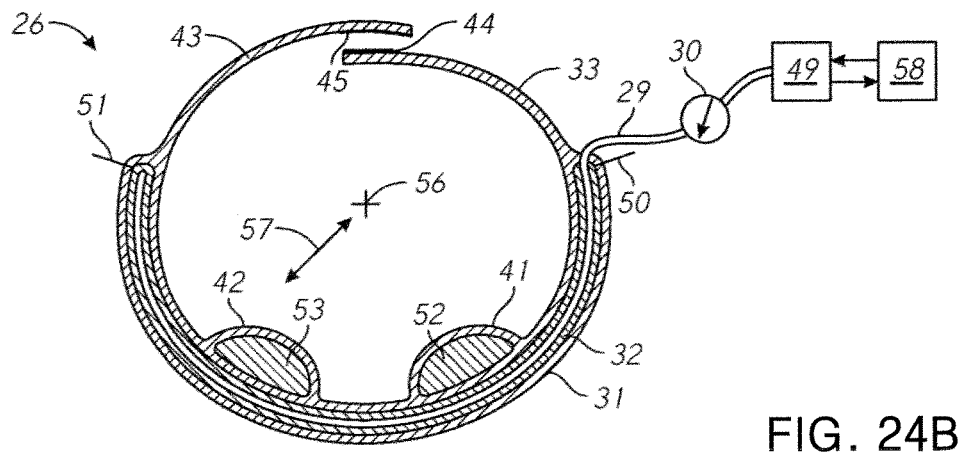
FIG. 24B is an example of a cross-sectional view of the device of FIG. 24A in a partially unactuated state.
Figure 24C:
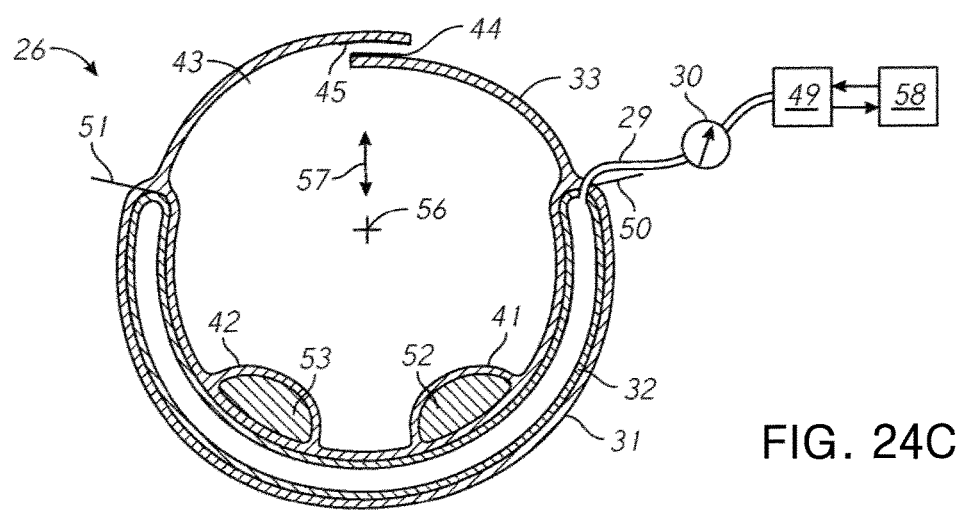
FIG. 24C is an example of a cross-sectional view of the device of FIG. 24A in a fully actuated state.
Figure 24D:
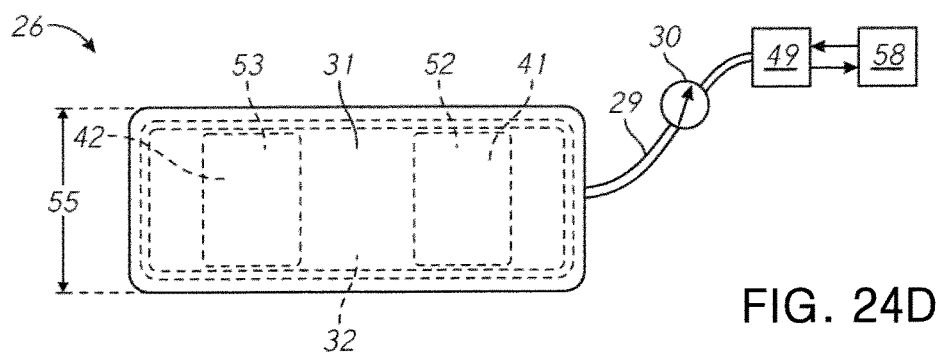
FIG. 24D is an example of a schematic view of the device of FIG. 24A.
Figure 24E:
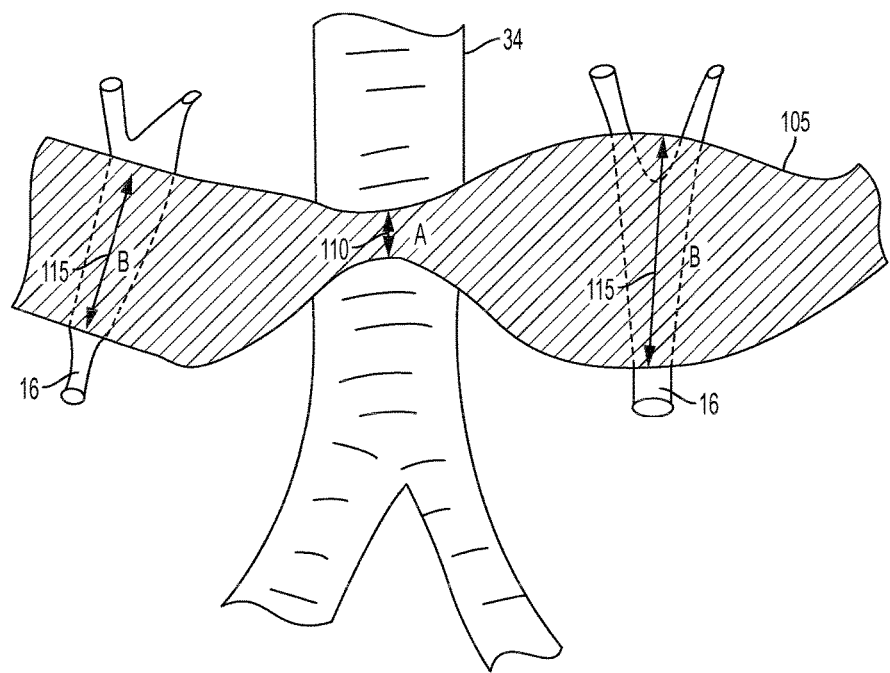
FIG. 24E is an example of a compression device.

FIG. 24E discloses an example embodiment of a compression device 105 in accordance with the disclosure herein. As illustrated in FIG. 24E, a compression device (e.g., compression neck collar) may be narrower (e.g., a distance A 110) in front of a trachea 34 (e.g., in front of the neck) of the patient and wider (e.g., a distance B 115) over an area overlapping the carotid arteries 16 (e.g., over lateral aspects of the neck) of the patient. In some embodiments, a compression device arranged in this manner may be a better fit for a patient having a short neck while leaving a wider area of the upper anterior chest and sternum exposed in order to facilitate sterile access to the patient's sternum in heart surgery in such a way that the vertical (longitudinal) dimension A of the front portion will be 50-70% narrower than the analogous dimension B of lateral portions of the compression device.

FIGS. 13-22, 25-32, 35, and 37A disclose modifications of the geometry of the vascular compression members 27 and 46 with respect to the geometry and anatomy of the patient in order to achieve compression of carotid and/or vertebral arteries in any combination.

FIGS. 15, 16, 20, 21B, and 23A demonstrate the method of use and the effect of inflation of the vascular compression device such as device 26 and it's different embodiments resulting in external compression of carotid arteries 16 and/or vertebral arteries 12 leading to transient interruption of carotid and/or vertebral flow. These figures demonstrate the anatomic relationship of the device 26 to carotid arteries 16, vertebral arteries 12 and surrounding structures 34, 35, 36, 37 and 40. The carotid arteries 16 are bordered by neck muscles 36 (comprising sternocleidomastoid muscles (SCM), scalenus muscles, sternothyroid and omohyoid muscles, longus colli muscles), esophagus 35, trachea 34 and fat tissues 40. These structures provide a protective cushion, minimizing the risk of the carotid and vertebral artery injury during external compression. In fact, an external compression of arteries 16 and 12 in this setting would lead to significantly lower risk of injury to carotid intima than intravascular carotid occlusion with the balloon or umbrella devices used for cerebral protection in patients undergoing carotid stenting. The longitudinal carotid (42, 46) and/or vertebral (42-V, 46-V) expandable members are positioned along the course of both carotid arteries 16 and/or vertebral arteries 12 on the neck. Similar considerations are applicable to protective compression of all other compressible arteries such as femoral and brachial arteries and the repeat description of identical processes is not necessary.

The exemplary embodiment of the device 26 may be any one of those previously disclosed that lacks a transverse carotid expandable member 32. However, it is to be understood that this is just one example and that other devices 26 that include member 32 can function in a similar manner to the device 26 disclosed in FIGS. 8A and 8B. As shown in FIGS. 15, 16, 20, 21B, and 23 longitudinal vascular compression members are placed along the course of target arteries such as carotid and/or vertebral artery, or brachial and femoral artery, or any other combination of compressible vessels. The lumen of the target arteries such as carotid or vertebral arteries is compressed between the vascular compression members anteriorly (outward in the radial direction 57) and the cervical spine 37 (or brachial and femoral bones in the case of the arteries of the extremities) posteriorly (inward in the radial direction 57). In some embodiments, the best level of compression of the arteries may occur by positioning the compression device and compression members at a level between the 4th and 7th cervical vertebrae (i.e. between C4 and C7 vertebrae of the cervical spine). This level of compression will correspond to the portions of the trachea 34 between the thyroid cartilage and the 6th tracheal ring. Actuation of the members 27 and 46 and/or 27-V, 46-V cause the members to move radially inward and compress fat tissue 40 that is immediately adjacent the device 26. In the case of the carotid artery compression the vascular compression members 27 and 46 are shown moving in the radial direction 57 inward of portions of the trachea 34 and neck muscles 36 so that portions of the vascular compression members 27 and 46 are closer to the central axis 56 in the radial direction 57 than portions of the trachea 34 and neck muscles 36. Full expansion of the vascular compression members 27 and 46 may result in inward radial movement so that they are not radially closer to the axis 56 than any portion of the esophagus 35. However, other embodiments are possible in which at least some portion of the vascular compression members 27 and 46 are closer to the central axis 56 than a portion of the esophagus 35. Actuation of the compression members 27-V and 46-V achieve similar compression of the vertebral arteries against the cervical spine, that would be most efficient at the level of C4-C7 vertebrae.

The soft tissues such as the fat tissues 40, neck muscles 36, esophagus 35 and trachea 34 around carotid arteries 16 provide a smooth cushion assuring adequate protection against carotid trauma. Same considerations will hold true in the case of compression of the arteries of upper and lower extremities and the repetition of them is not necessary. In the case of protection of both carotid arteries, the actuation of the members 27,46 and/or 27-V, 46-V causes the areas of compression to restrict blood flow through the carotid arteries 16 and/or vertebral arteries 12 which leads to transient limitation or interruption of cerebral flow. The trachea 34 and esophagus 35 are not closed or restricted upon actuation of the expandable members 27 and 46 due to the placement and specific configuration of said expandable members. The fact that in most cases this maneuver is performed while the patient is intubated and sedated makes the risk of compression of trachea minimal. Performing the same procedure on the ambulatory basis, however, or while the patient is not intubated, may prove to be hazardous. However, in some arrangements some degree of restriction of the trachea 34 and/or esophagus 35 may occur and is considered acceptable in the setting of general anesthesia with endotracheal intubation and mechanical ventilation. It is advisable, however, to obtain Duplex scan in all patients planned for this procedure to rule out significant atherosclerotic disease of these vessels, especially if carotid arteries 16 are compressed. The mere presence of carotid artery disease in these patients should be considered a contraindication to carotid compression due to increased risk of carotid atherosclerotic plaque injury leading per se to distal cerebral embolization and stroke i.e. defeating the purpose of such a procedure.

The divergence of potential distal emboli such as cerebral emboli 17, 18 and prevention of ischemic organ injury such as stroke can be achieved by a noninvasive safe method that involves external compression of the vessel, such as carotid, vertebral or some other arteries and veins, carrying said emboli. The method and device 26 disclosed do not require puncture of the skin or vessels and do not necessitate the use of endovascular devices. The device 26 and disclosed method allow for the divergence of emboli such as carotid and vertebral emboli 17 and 18 of all sizes, including those microscopic particles that are too small to be trapped with the known intravascular filters.

Various types of mechanisms capable of compressing the carotid arteries 16, vertebral arteries 12 and other vessels can be included in the device 26 in addition to or alternatively to those previously discussed. For example, the device 26 can be supplied with different vascular compression mechanisms, including different forms and shapes of longitudinal or transverse bladders, cuffs, compression pads or inserts with the same effect of vascular compression to the point of transient limitation or interruption of blood flow. The fluid provided to pressurize the expandable components of the device 26 from the pressure source 49 may be a liquid substance in some embodiments. Fluid that is a liquid may be used in the device 26 to effect pressurization and more uniform constriction of the carotid arteries 16 than gas or air fluid because liquid is more non-compressible at the operating range of pressures. Liquid fluid in members 27, 32 and 46 may more directly transmit pressure to the carotid area than gas or air fluid.

Figure 14:
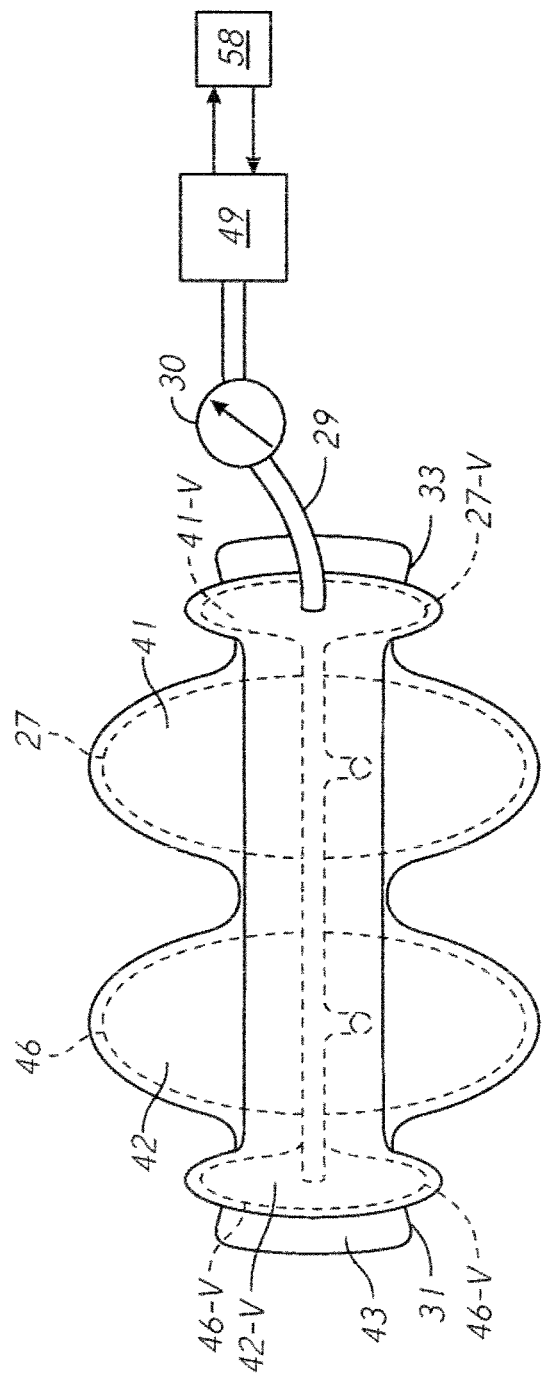
FIG. 14 is an example of a schematic view of a device for carotid and/or vertebral compression, depicted on FIG. 13.

As previously described and as illustrated in FIG. 14, a device resembling a neck collar may be applied to a patient's neck before proceeding with a surgical intervention. The device (e.g., the device of any of FIGS. 13-24D, 37B) may have several pockets and chambers to accommodate different compression members, such as the compression members described with respect to FIGS. 13-32, 35, 37A. The compression members may be shaped and/or sized to provide for safe, efficient, and/or anatomically sound compression of arteries in the neck. The compression members may be replaced, combined, and/or exchanged depending on the specifics of an anatomy of a particular patient's neck.

Figure 15:
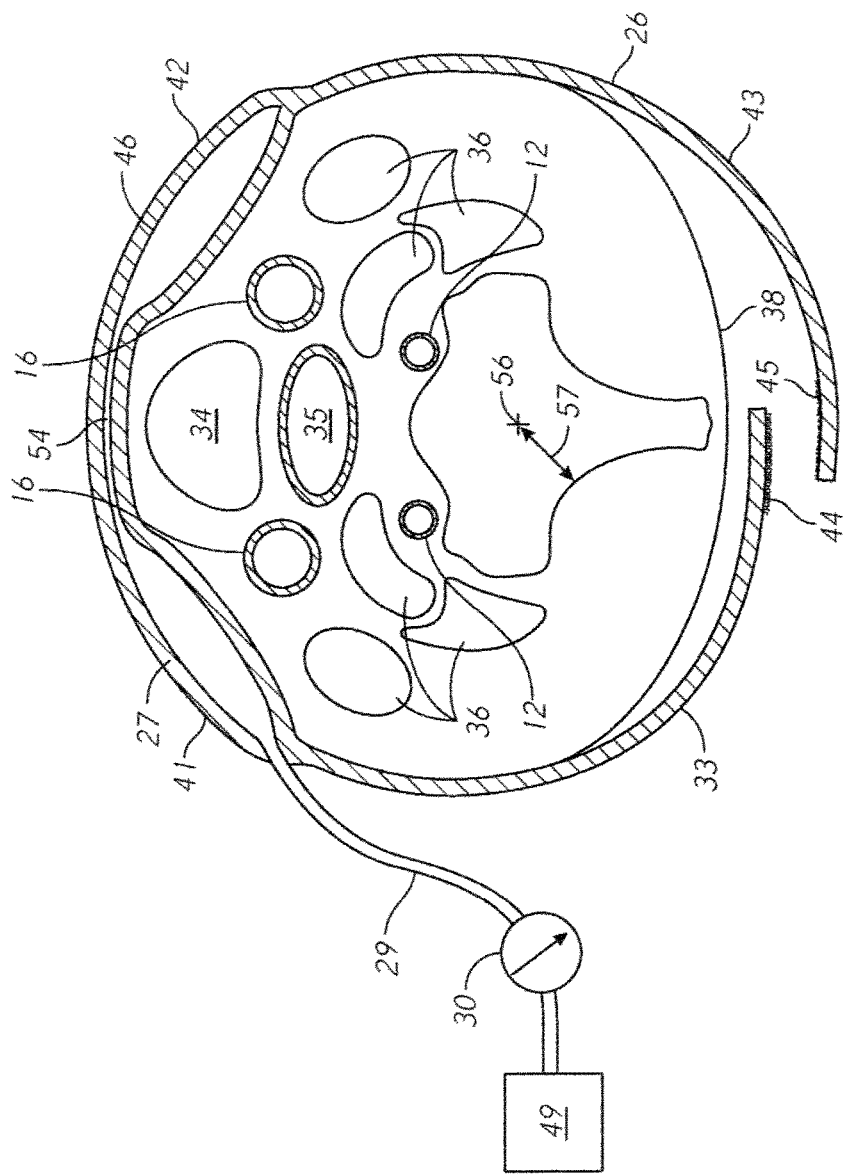
FIG. 15 is an example of a cross-sectional view of a neck of a patient and a device attached thereto in an unactuated state.
Figure 16:
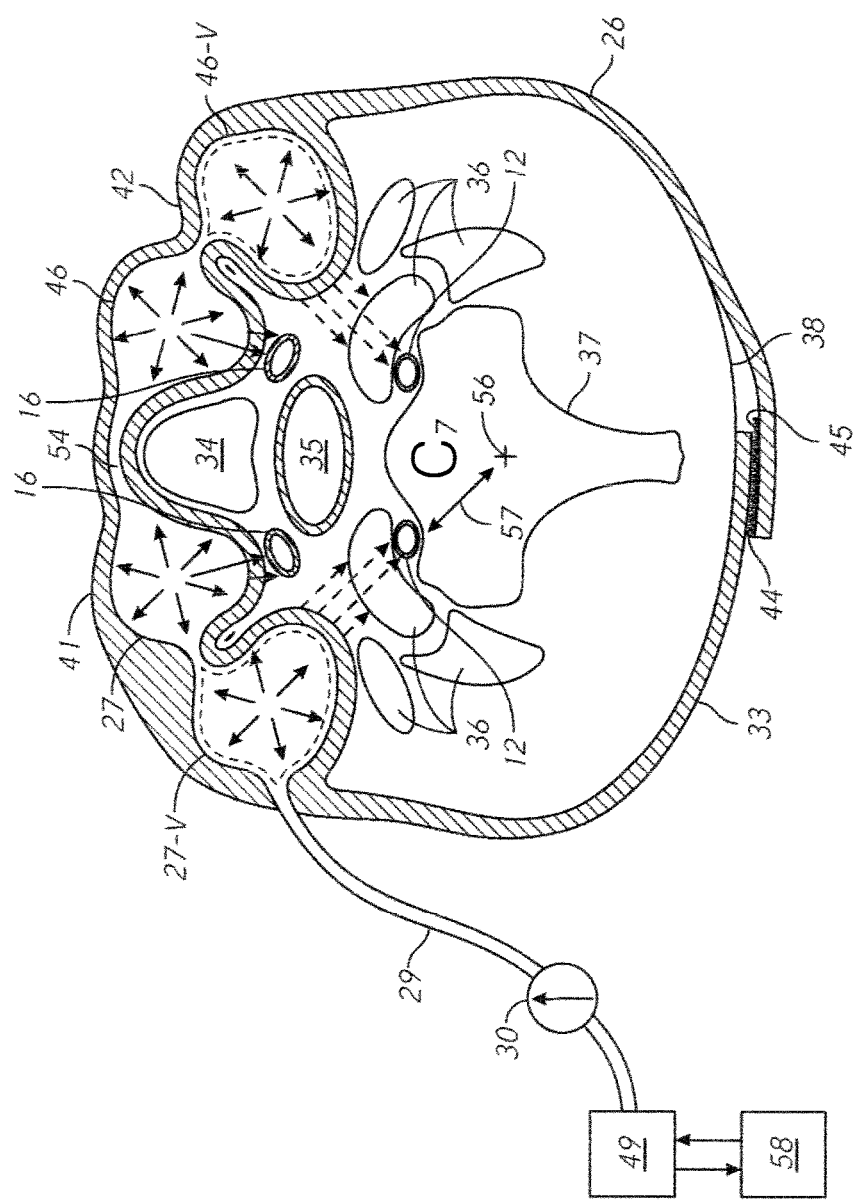
FIG. 16 is an example of a cross-sectional view of a neck of a patient and a device attached thereto in an actuated state.
Figure 17:
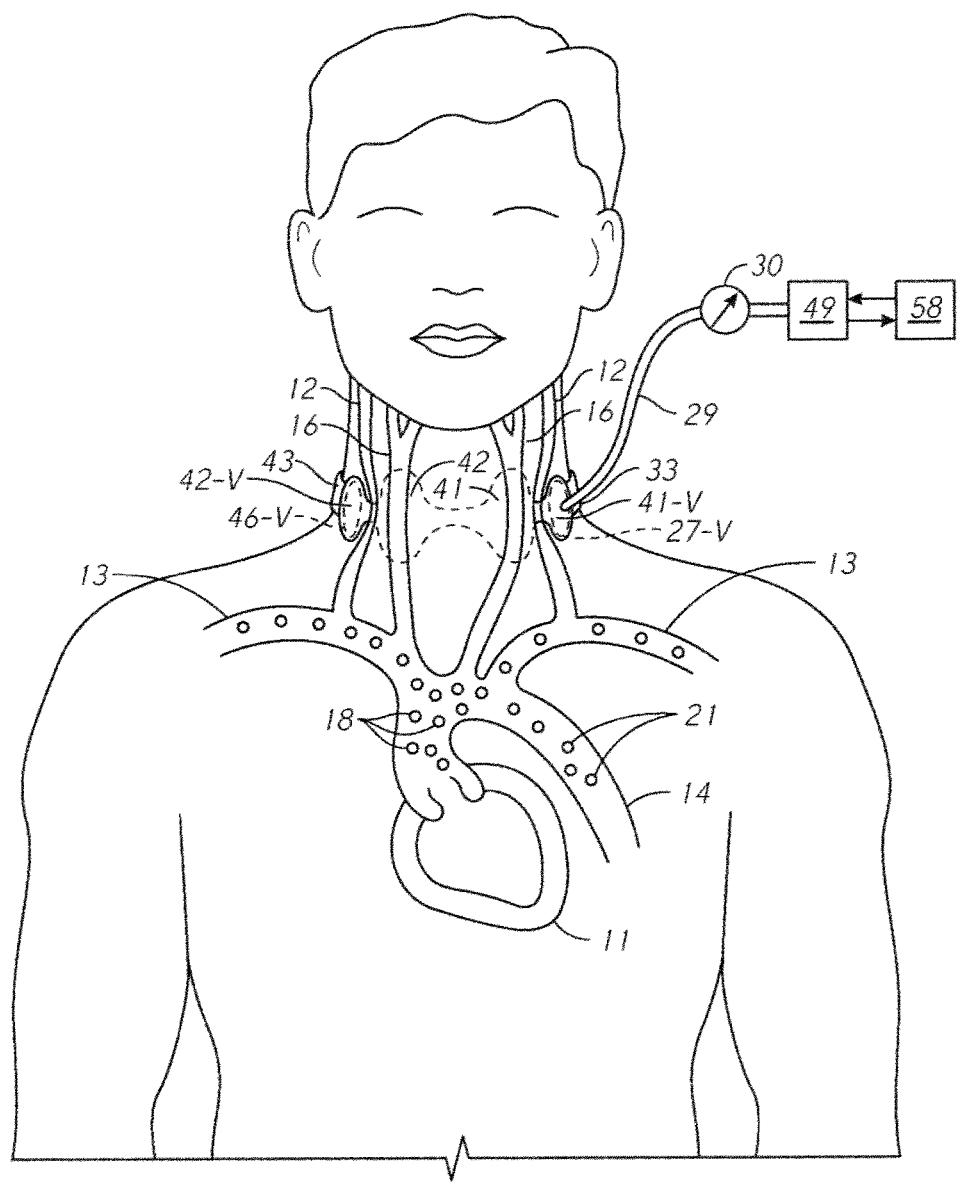
FIG. 17 is an example of a front view of a patient with a compression device in accordance with another exemplary embodiment, leading to selective compression of vertebral arteries.
Figure 18:
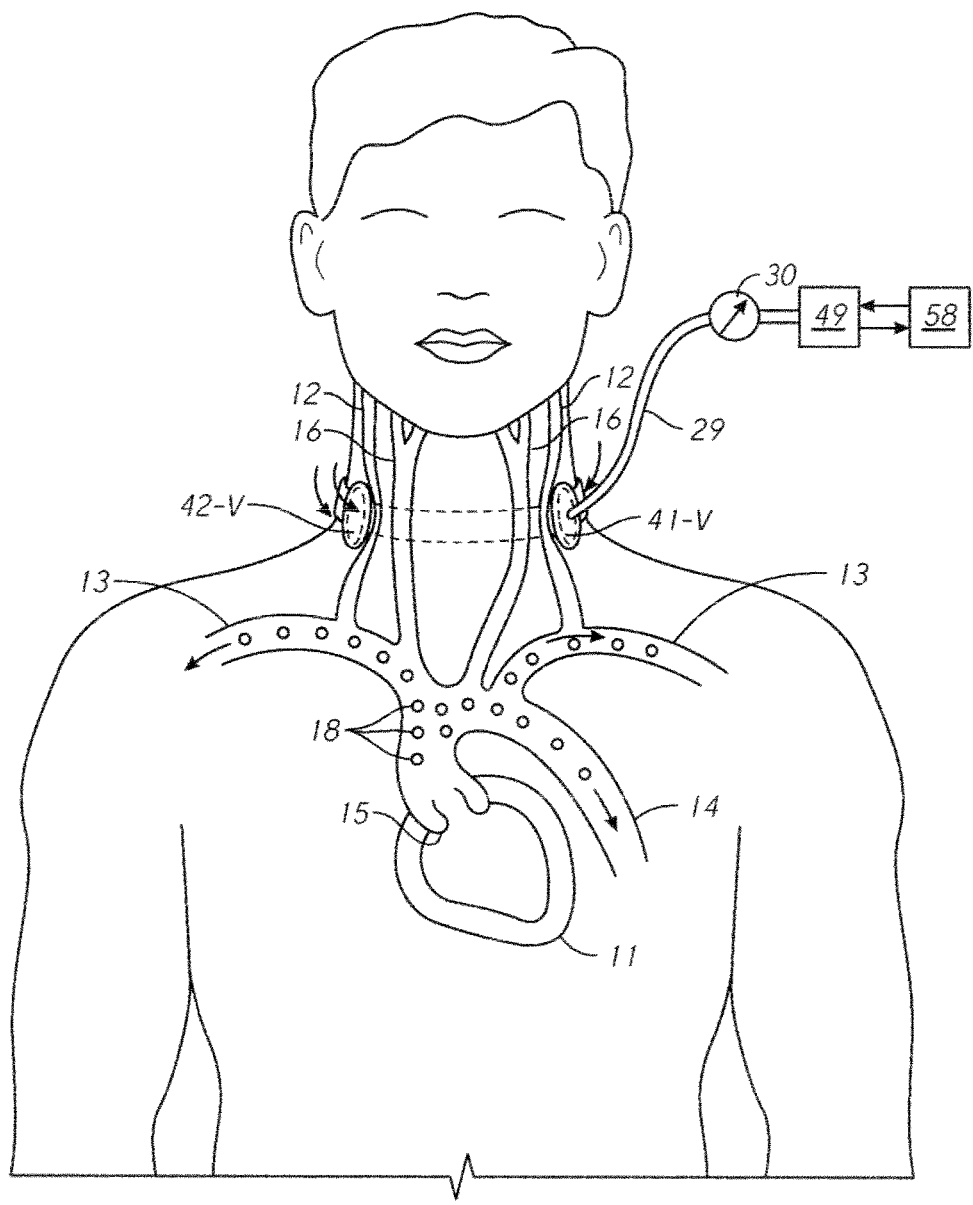
FIG. 18 is an example of a front view of a patient with a compression device for vertebral arteries in accordance with yet another exemplary embodiment.
Figure 19:
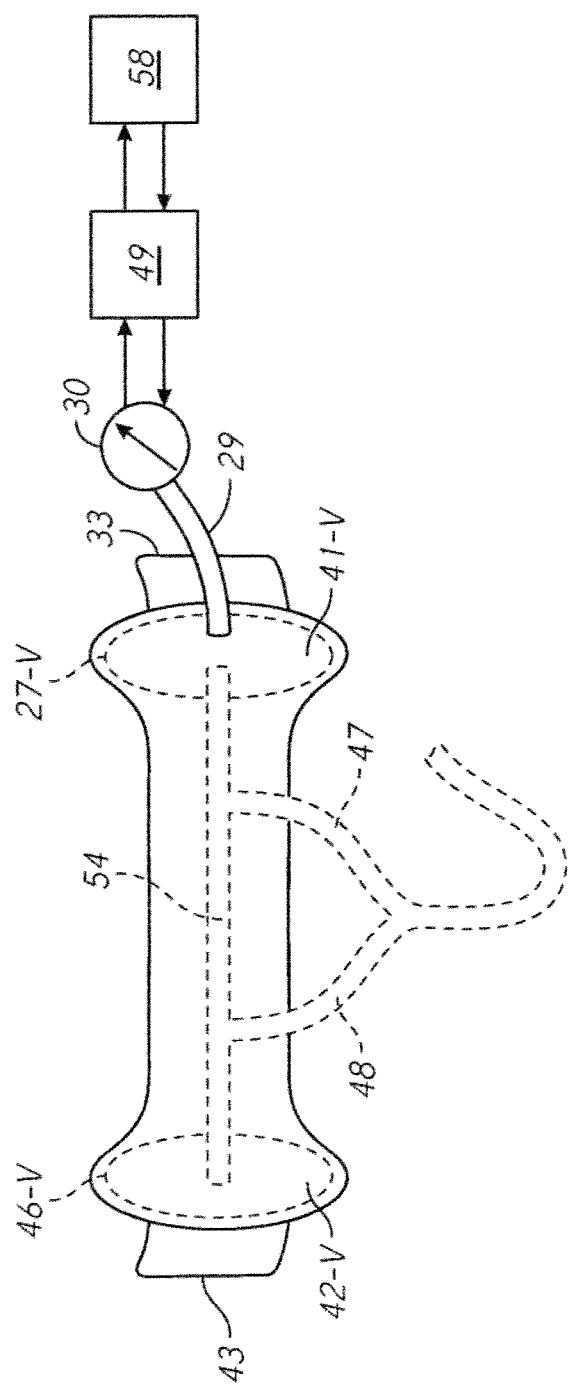
FIG. 19 is an example of a schematic view of a device for vertebral compression, similar to the device depicted on FIG. 18, but carrying features of an additional exemplary embodiment.

As previously described, FIGS. 15 and 16 illustrate a cross-sectional view of a neck, explaining the specifics of the anatomical position of the carotid and vertebral arteries, and the surrounding vital structures, as the trachea 34, esophagus 35, jugular vein, spine, brachial plexus, and the sternocleidomastoid or scalenus muscle 36. In some embodiments, each compression member may have a certain shape, size, and/or configuration aimed at selectively reaching the artery in an anatomical groove of a neck having certain anatomical proportions to provide compression limited to the artery. For example, the provided compression could be similar to a doctor's finger reaching into the anatomical groove in the neck of a patient to compress a target blood vessel. FIGS. 15 and 16 illustrate that the anatomic features of the carotid area of the neck favor compression using compression members having particular cross-sectional shapes, such as a cone shape, pear shape, wedge shape, 2-lobar shape, 3-lobar shape, 1-finger shape, 2-finger shape, 3-finger shape, and/or 4-finger shape. A compression member having such a cross-sectional shape would be able to enter an anatomical groove between the trachea 34 medially and the neck muscles (e.g., sternocleidomastoid muscle 36) laterally, and reach the blood vessel to be compressed without encountering resistance from the surrounding structures of the neck, such as the trachea 34, sternocleidomastoid muscle 34, and the spine, and therefore without applying the same degree of pressure to these structures.

FIGS. 25-31 illustrate example variations of cross-sectional shapes and configurations of compression members designed for selective, anatomic compression of carotid and/or vertebral arteries to prevent embolic stroke. The members may be designed for use alone, or in combination with other members, to selectively compress a target neck artery (16—carotid artery and/or 12—vertebral artery) in its anatomical groove without the need for overcoming resistance and anatomic barriers created by surrounding anatomic structures, such as trachea 34, muscle(s) 405 (e.g., sternocleidomastoid muscle (SCM) and/or other muscles, such as scalenus muscles, sternothyroid and omohyoid muscles, longus colli muscles), and spine 37. Moreover, one or more of the disclosed shapes are capable of orienting themselves in an optimal position against an artery to be compressed by entering an arterial groove and extending into a depth of the arterial groove while being expanded or pressurized externally. The arterial groove may be a groove between a trachea 34 medially and a muscle (e.g., sternocleidomastoid muscle 405) laterally, and may contain a blood vessel (e.g., carotid artery 420). In other embodiments, the arterial groove may be a groove between spine 37 medially and a muscle (e.g., sternocleidomastoid muscle, longus colli and scalenus muscle 405) laterally, and may contain a vertebral artery. The choice of type and geometry of each particular compression member can be based on a neck exam and data of a neck CT scan, performed before a procedure.

As a result, a portion of a compression member, such as a tip of a compression member having a cross-sectional shape that is cone-shaped, wedge-shaped, bilobar shaped, or trilobar shaped, may lodge in between trachea 34 and a muscle 405 (e.g., sternocleidomastoid and/or other neck muscles such as scalenus muscles, longus neck muscles, omohyoid and omothyroid muscles), while reaching directly to vessel 420 (e.g., carotid artery 16 or vertebral artery 12) in the depth of an arterial groove. In addition, a wider outer (external) surface of a compression member (e.g., a compression member having a cross-sectional shape that is wedge-shaped, pear-shaped, or cone-shaped) would provide adequate area for a correct anatomical orientation and stabilization of the compression member over a target artery 420, such as a carotid artery 16 or vertebral artery 12. It will also assure that the pressure forces are transmitted primarily to the underlying target artery (e.g., carotid artery 16 or vertebral artery 12) and much less to the side structures, such as trachea 34, esophagus 35, and neck muscle 420 (e.g., sternocleidomastoid and/or other neck muscles, such as the longus colli and scalenus muscles). As a result, application of an outer circular or local compression force may urge the compression member to apply pressure directly to the artery, and only indirectly (under a certain angle) to side structures (such as trachea 34 medially and muscle 420 and a jugular vein laterally).

Figure 25:
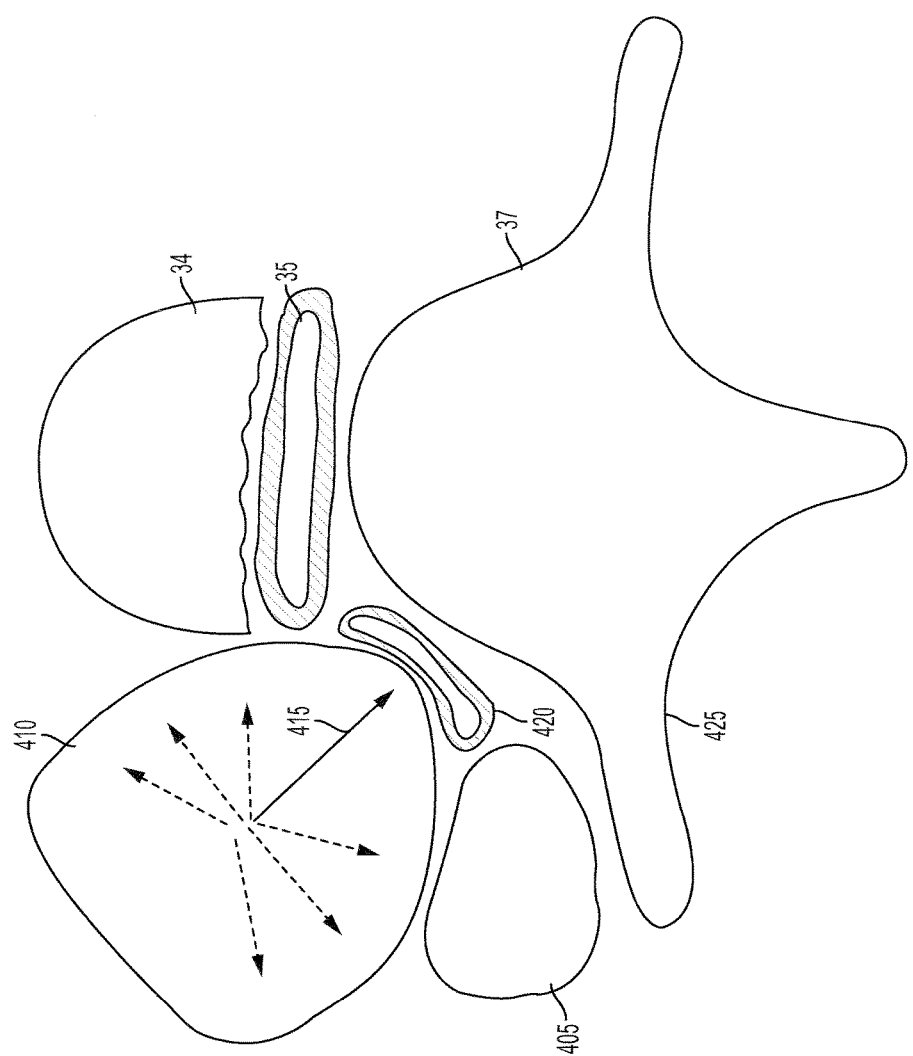
FIG. 25 illustrates an example of a compression member having a conic cross-sectional shape.

For example, FIG. 25 illustrates an example of a compression member 410 having a conic cross-sectional shape. As shown in FIG. 25, compression member 410 may be narrower at one end of the compression member and wider at the other end. This allows one end of compression member 410 to be directed into the space between the trachea 34, esophagus 35, spine 37 (with transverse process of spine vertebra 425), and a muscle (e.g., sternocleidomastoid or other neck muscle), to compress artery 420 (e.g., carotid artery 16, vertebral artery 12), while the other, wider end of compression member 410 provides for correct orientation and stabilization of compression member 410 over artery 420. When compressed, the main force of the compression may direct compression member 410 in the direction of arrow 415, while compression member 410 may be directed with small forces (illustrated by the dotted arrows of FIG. 25) onto the surrounding structures (e.g., trachea 34, esophagus 35, muscle(s) 405). These small forces may help to orient and/or stabilize compression member 410 over target artery 420.

Figure 26:
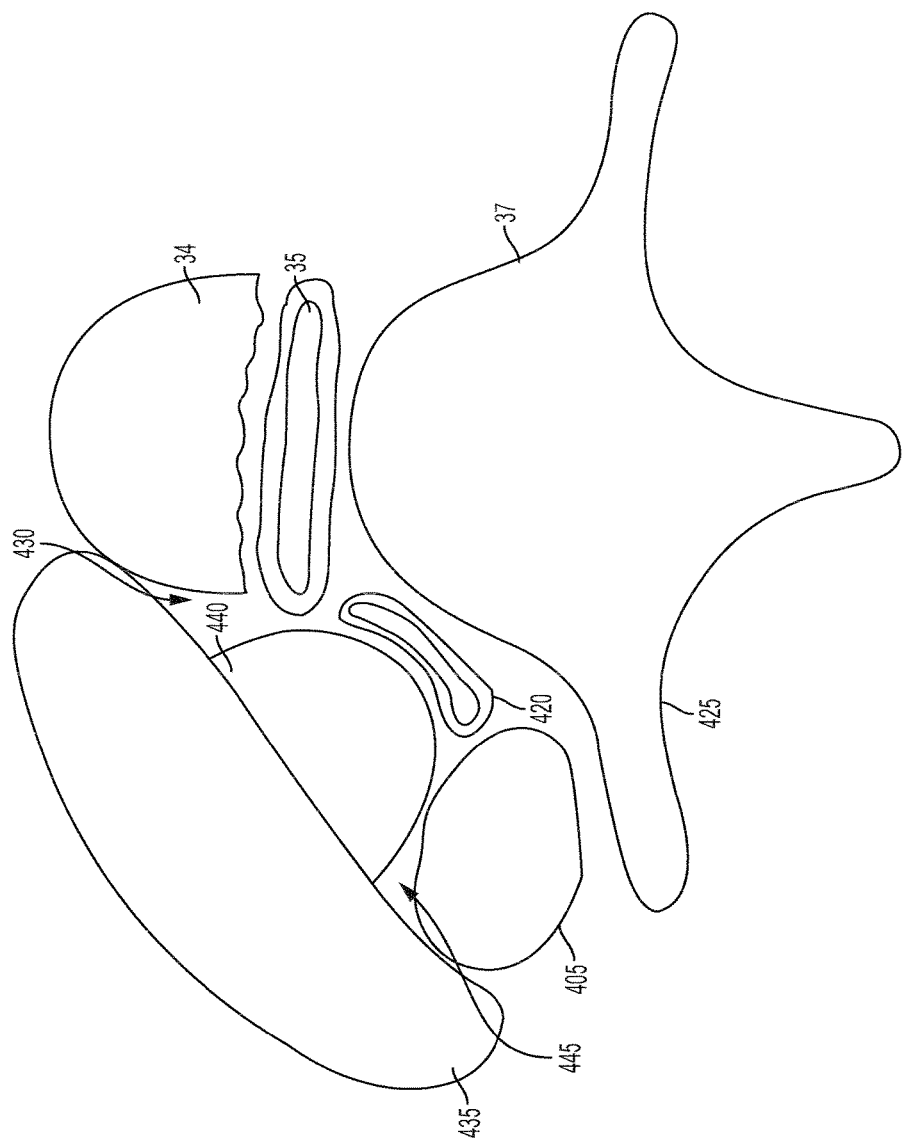
FIG. 26 illustrates an example of a compression member having an arcuate cross-sectional shape in combination with another compression member, such as a compression member with a cross-sectional shape that is a conic shape, oval shape, or pear shape.

FIG. 26 illustrates an example of a compression member 435, 440 having an outer compression member 435 with an arcuate cross-sectional shape in combination with another compression member 440 (e.g., a compression member with a cross-sectional shape that is conic-shaped, oval-shaped, or pear-shaped). Compression members 435 and 440 may be formed together of the same material (e.g., an inflatable balloon, foam), or be two separate members that are fixed together (e.g., with fabric, adhesive). As shown in FIG. 26, compression member 440 may be narrow at one end, while compression member 435 may be wider than compression member 435. This allows compression member 440 to be directed into the arterial groove 430, 445 between the trachea 34, esophagus 35, spine 37 (with transverse process of spine vertebra 425), and a muscle 405 (e.g., sternocleidomastoid or other neck muscle), to compress artery 420 (e.g., carotid artery 16, vertebral artery 12), while the wider compression member 435 provides for correct orientation and stabilization of compression member 440 over artery 420 (e.g., carotid artery 16, vertebral artery 12). When compressed, the main force of the compression may direct compression member 440 toward artery 420, while compression member 435 may be directed with small forces onto the surrounding structures (e.g., trachea 34, muscle(s) 405). These small forces may help to orient and/or stabilize compression member 440 over target artery 420.

Figure 27:
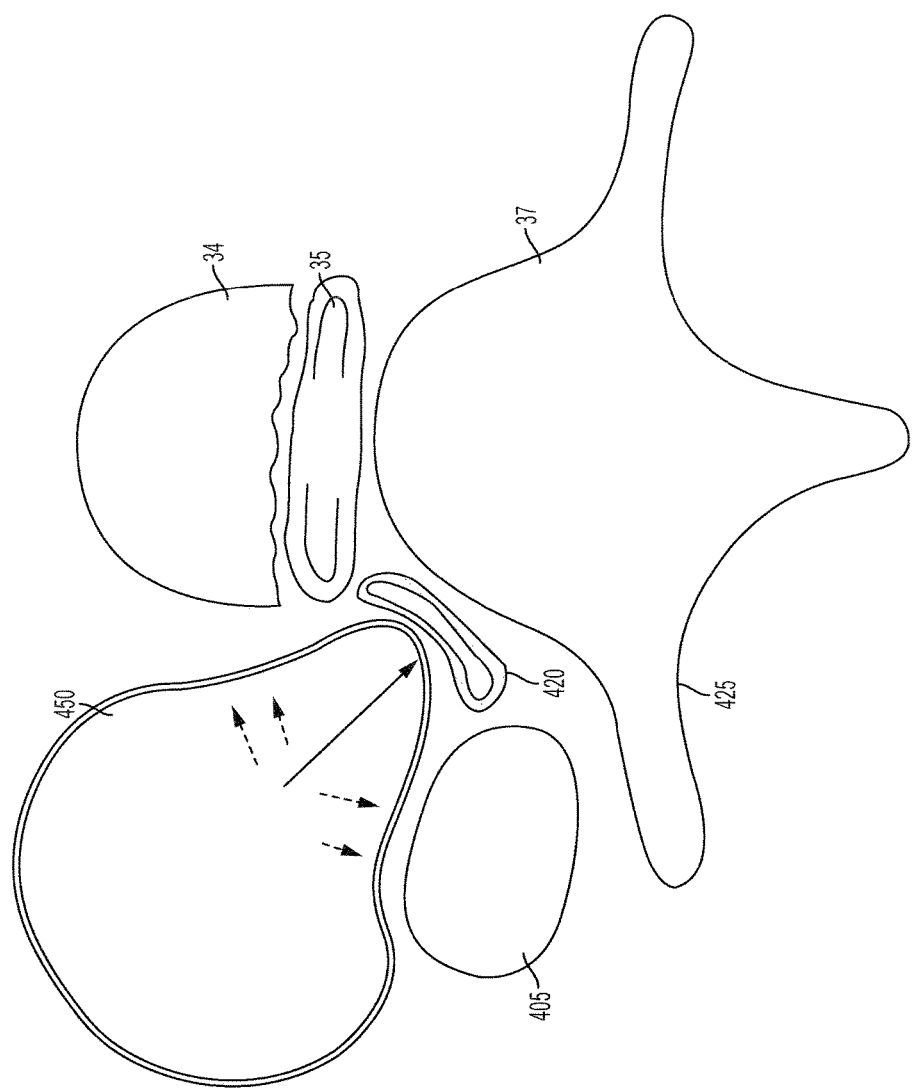
FIG. 27 illustrates an example of a compression member having a pear cross-sectional shape.

FIG. 27 illustrates an example of a compression member 450 with a cross-sectional shape that is pear-shaped. As shown in FIG. 27, compression member 450 may be narrower at one end of the compression member and wider at the other. This allows one end of compression member 450 to be directed into the space between the trachea 34, esophagus 35, spine 37 (with transverse process of spine vertebra 425), and a muscle (e.g., sternocleidomastoid or other neck muscle), to compress artery 420 (e.g., carotid artery 16, vertebral artery 12), while the other, wider end of compression member 450 provides for correct orientation and stabilization of compression member 450 over artery 420. When compressed, the main force of the compression may direct compression member 450 in the direction of the solid arrow illustrated in FIG. 27, while compression member 450 may be directed with small forces (illustrated by the dotted arrows of FIG. 27) onto the surrounding structures (e.g., trachea 34, esophagus 35, muscle(s) 405). These small forces may help to orient and/or stabilize compression member 450 over target artery 420.

Figure 28:
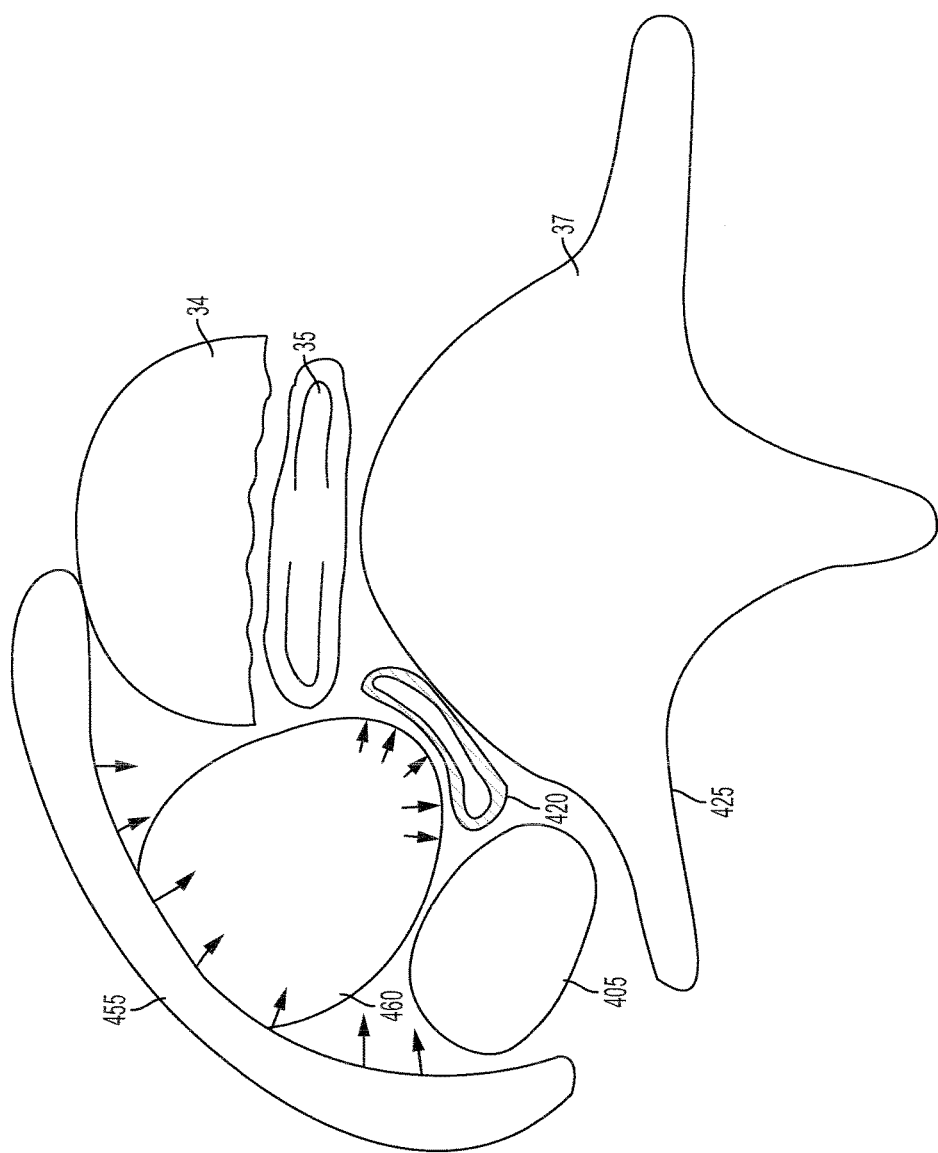
FIG. 28 illustrates an example of a compression member having a crescent cross-sectional shape in combination with another compression member, such as a compression member with a cross-sectional shape that is a conic shape, oval shape, or pear shape.

FIG. 28 illustrates an example of a compression member 455, 460 having an outer compression member 455 with a crescent cross-sectional shape in combination with another compression member 460 (e.g., a compression member with a cross-sectional shape that is conic-shaped, oval-shaped, or pear-shaped). Compression members 455 and 460 may be formed together of the same material (e.g., an inflatable balloon, foam), or be two separate members that are fixed together (e.g., with fabric, adhesive). As shown in FIG. 28, compression member 460 may be narrow at one end, while compression member 455 may be wider than compression member 460. This allows compression member 460 to be directed into the arterial groove between the trachea 34, esophagus 35, spine 37 (with transverse process of spine vertebra 425), and a muscle (e.g., sternocleidomastoid or other neck muscle), to compress artery 420 (e.g., carotid artery 16, vertebral artery 12), while the wider compression member 455 provides for correct orientation and stabilization of compression member 460 over artery 420 (e.g., carotid artery 16, vertebral artery 12). When compressed, the main force of the compression may direct compression member 460 toward artery 420 (as illustrated by the arrows of compression member 460 adjacent artery 420), while compression member 455 may be directed with small forces onto the surrounding structures (e.g., trachea 34, muscle(s) 405) (as illustrated by the arrows adjacent compression member 455). These small forces may help to orient and/or stabilize compression member 460 over target artery 420.

Figure 29:
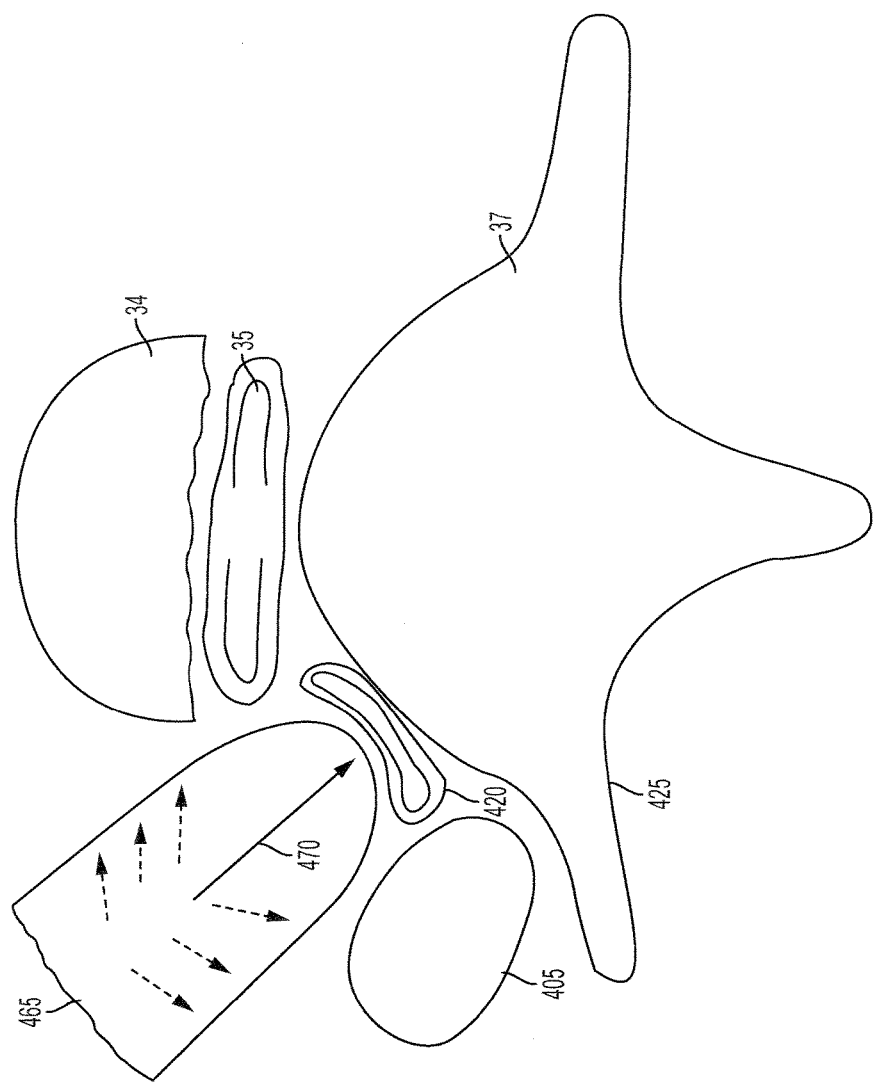
FIG. 29 illustrates an example of a compression member having a single finger cross-sectional shape with a tip aimed at a target artery.

FIG. 29 illustrates an example of a compression member 465 with a cross-sectional shape that is finger-shaped. As shown in FIG. 29, compression member 465 may be narrower at one end of the compression member and wider at the other. This allows the narrower end of compression member 465 to be directed into the arterial groove between the trachea 34, esophagus 35, spine 37 (with transverse process of spine vertebra 425), and a muscle (e.g., sternocleidomastoid or other neck muscle), to compress artery 420 (e.g., carotid artery 16, vertebral artery 12), while the other, wider end of compression member 465 provides for correct orientation and stabilization of compression member 465 over artery 420. When compressed, the main force of the compression may direct compression member 465 in the direction of arrow 470, while compression member 465 may be directed with small forces (illustrated by the dotted arrows of FIG. 29) onto the surrounding structures (e.g., trachea 34, esophagus 35, muscle(s) 405). These small forces may help to orient and/or stabilize compression member 465 over target artery 420. For example, compression of compression member 465 with a cross-sectional shape that is finger-shaped may mimic a doctor pressing a finger against an artery (e.g., carotid artery 16, vertebral artery 12) of a patient.

Figure 30:
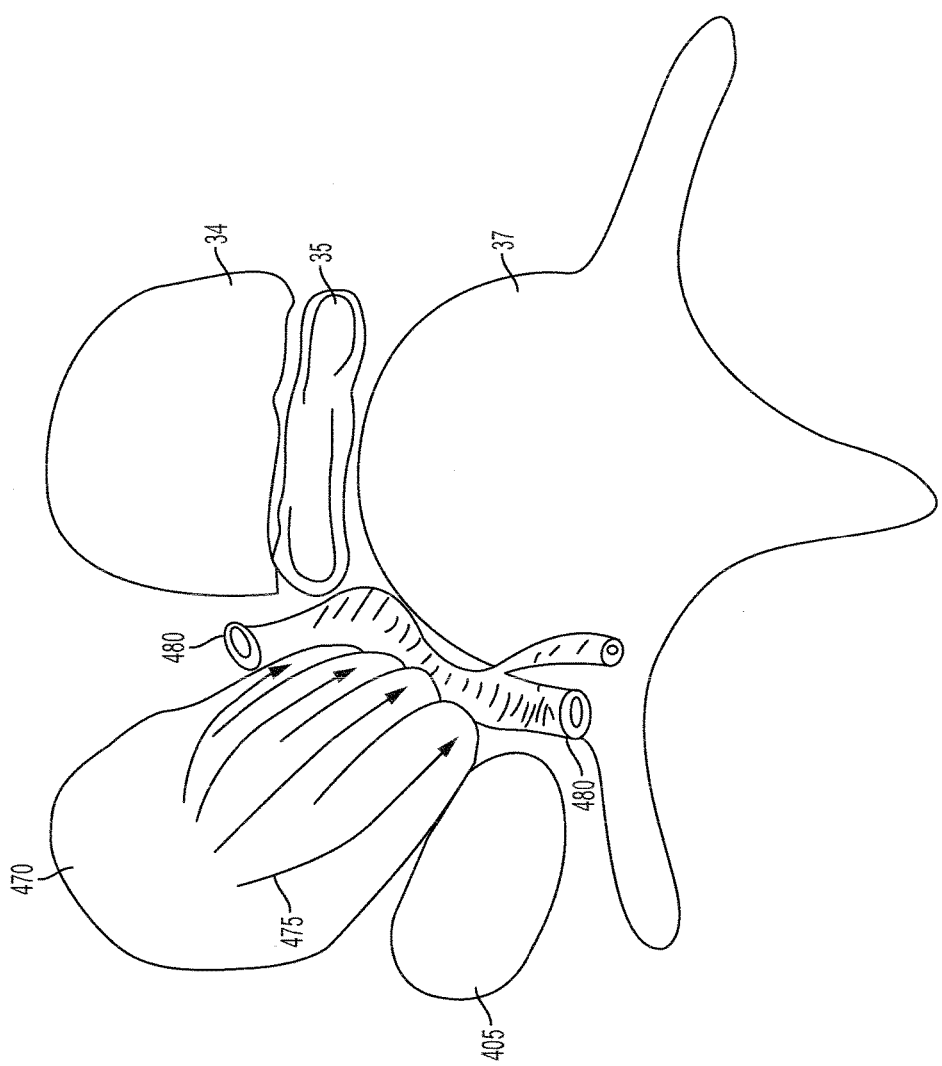
FIG. 30 illustrates an example of a compression member having a multiple finger cross-sectional shape with tips aimed at a target artery.

FIG. 30 illustrates an example of a multiple finger-shaped compression member 470. For example, compression member 470 is illustrated in FIG. 30 as being a compression member having a cross-sectional shape that is four finger shaped. However, a shape representing any number of fingers could be used (e.g., a compression member having a cross-sectional shape that is two finger shaped or three finger-shaped). As shown in FIG. 30, compression member 470 may be directed into the arterial groove between the trachea 34, esophagus 35, spine 37, and a muscle (e.g., sternocleidomastoid or other neck muscle), to compress artery 480 (e.g., carotid artery 16, vertebral artery 12). When compressed, the main force of the compression may direct the fingers of compression member 470 in the direction of arrows 475. Use of multiple finger elements in a compression member, such as in compression member 470, may allow a course of artery 480 to be compressed. For example, compression of a compression member 480 with a cross-sectional shape that is multiple finger shaped may mimic a doctor pressing multiple fingers against an artery 480 (e.g., carotid artery 16, vertebral artery 12) of a patient. In some embodiments, compression along a longer course of artery 480 may help to minimize flow of blood (and embolic particles) through artery 480 to a vulnerable organ.

Figure 31:
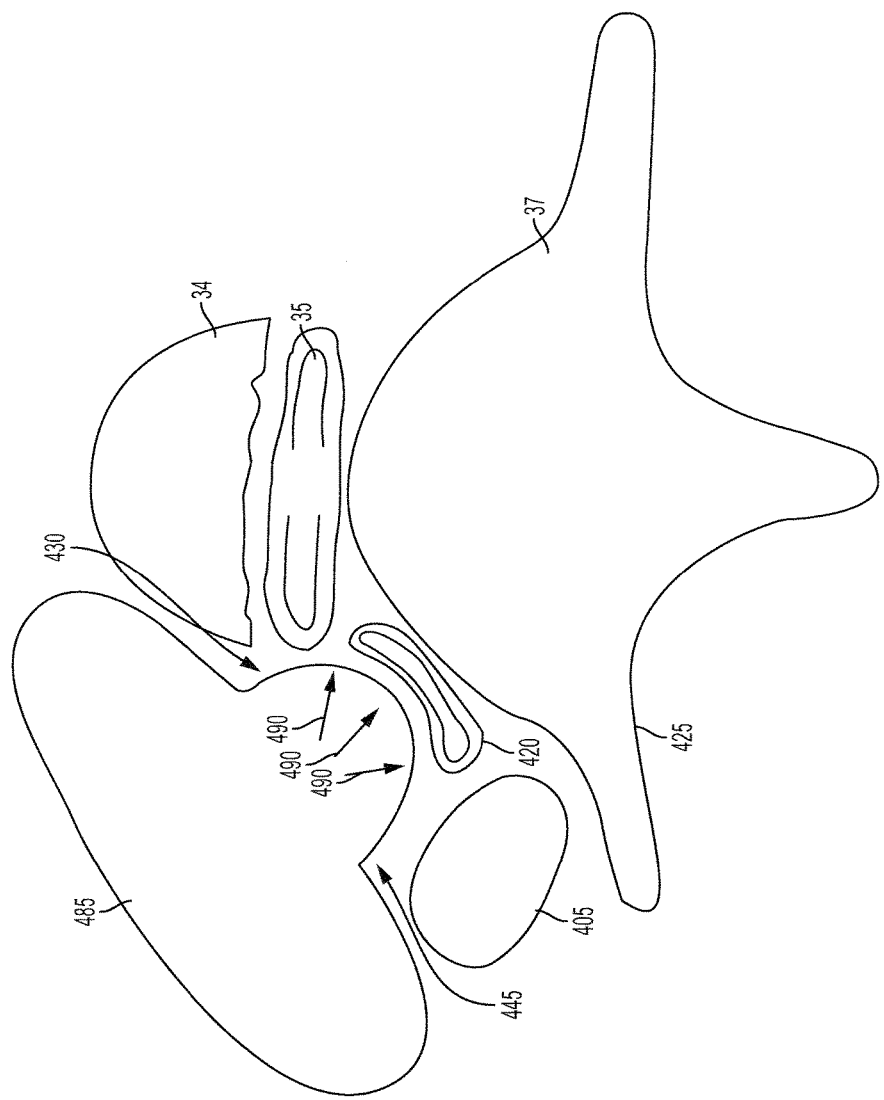
FIG. 31 illustrates an example of a compression member with a bilobar cross-sectional shape.

FIG. 31 illustrates an example of a compression member 485 having a bilobar cross-sectional shape. As shown in FIG. 31, compression member 485 may be narrow at one end and wider at the other end. This allows the narrow end of compression member 485 to be directed into the arterial groove 430, 445 between the trachea 34, esophagus 35, spine 37 (with transverse process of spine vertebra 425), and a muscle (e.g., sternocleidomastoid or other neck muscle), to compress artery 420 (e.g., carotid artery 16, vertebral artery 12), while the wider end of compression member 485 provides for correct orientation and stabilization of compression member 485 over artery 420 (e.g., carotid artery 16, vertebral artery 12). When compressed, the main force of the compression may direct compression member 485 toward artery 420 in the direction 490, while compression member 485 may be directed with small forces onto the surrounding structures (e.g., trachea 34, muscle(s) 405). These small forces may help to orient and/or stabilize compression member 485 over target artery 420, while an outer portion of compression member 485 may rest on surrounding structures, such as a trachea 34 medially and a sternocleidomastoid or anterior scalenus muscle 405 laterally.

Figure 32:
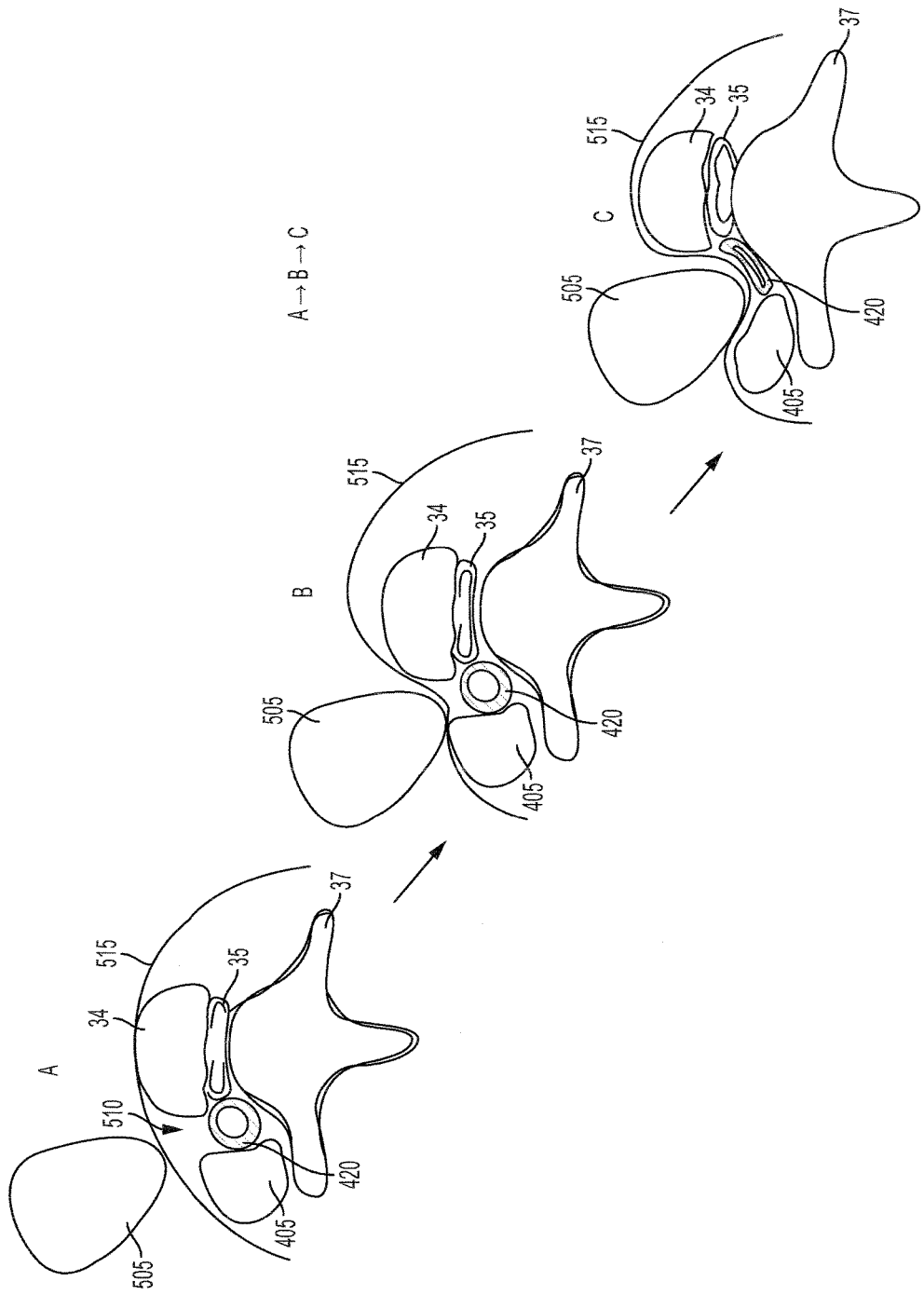
FIG. 32 illustrates an example of a self-centering and structure-spreading effect of a compression member with a conic cross-sectional shape leading to selective compression of an artery while self-positioning between surrounding structures and conforming to the anatomy of a neck triangle.

FIG. 32 illustrates an example of a self-centering and structure-spreading effect of a compression member 505 with a conic cross-section shape leading to compression of an artery 420 (e.g., carotid artery 16, vertebral artery 12), while the conic cross-sectional shape of compression member 505 causes the compression member to automatically position itself between surrounding structures (e.g., trachea 34, esophagus 35, muscle(s) 405) when compressed. As illustrated in A of FIG. 32, prior to an emboligenic event, compression may not be applied to compression member 505, and compression member 505 may be aligned next to the skin 515 of a patient's neck outside an arterial groove 510. As illustrated in B of FIG. 32, when a small amount of compression is applied, compression member 505 may be pressed against the skin 515 of a patient and directed into arterial groove 510, but may not compress artery 420. As illustrated in C of FIG. 32, when a moderate or high amount of compression is applied, compression member 505 may be further directed into arterial groove 510 than in B, which may cause a narrow end of compression member 505 to be wedged into the space between the trachea 34, esophagus 35, spine 37, and a muscle (e.g., sternocleidomastoid or other neck muscle), to compress artery 420 (e.g., carotid artery 16, vertebral artery 12), while the other, wider end of compression member 410 may provide for correct orientation and stabilization of compression member 505 over artery 420. When compressed, the main force of the compression may direct compression member 505 in the direction toward artery 420, while compression member 505 may be directed with small forces onto the surrounding structures (e.g., trachea 34, esophagus 35, muscle(s) 405). These small forces may help to orient and/or stabilize compression member 505 over target artery 420.

Figure 33:
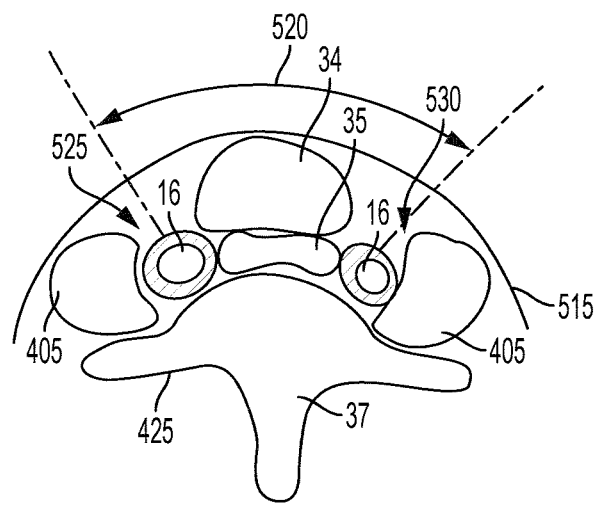
FIG. 33 illustrates an example of an inter-carotid distance.
Figure 34:
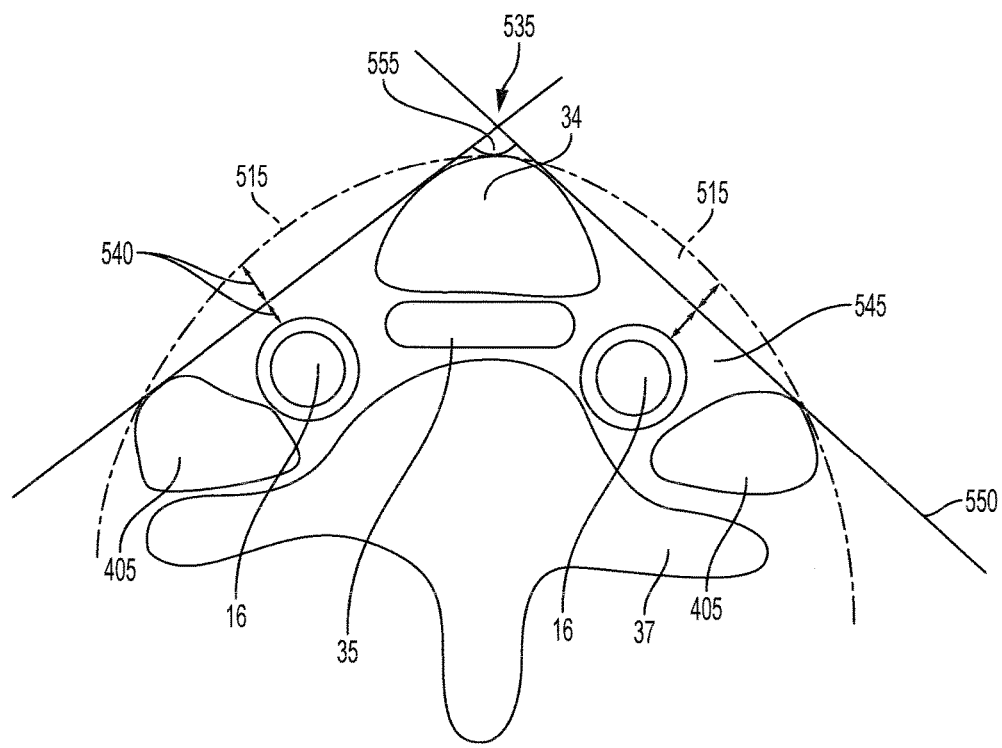
FIG. 34 illustrates an example of carotid bridging.
Figure 35:
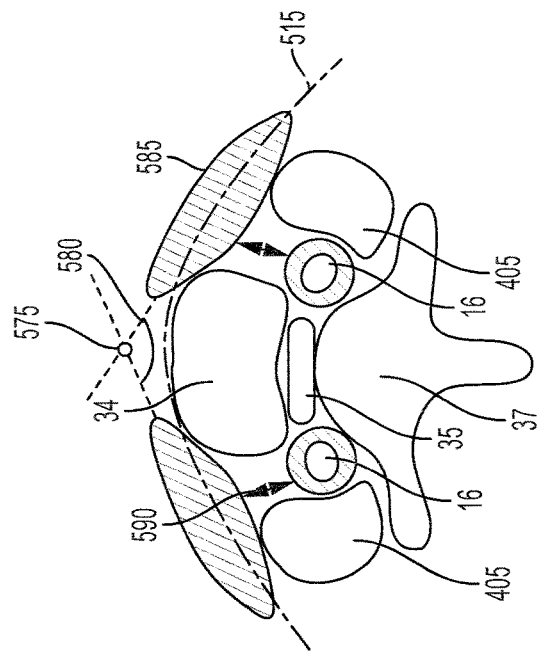
FIG. 35 illustrates an example of a tracheal hinge.
Figure 35:
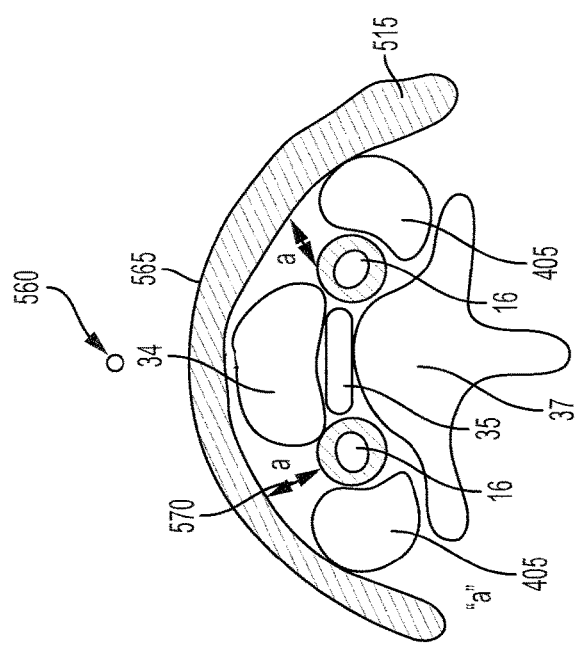

FIGS. 33-35 explain the mechanism of action of carotid and/or vertebral compression members, and of carotid compression in general. For the sake of simplicity, the scalenus muscles located laterally from the vertebral arteries and the longus colli muscle, located medially to the vertebral arteries, are not depicted.

FIG. 33 illustrates the concept of "inter-carotid distance." Inter-carotid distance 520 is the distance between the right and left carotid arteries as measured by the anterior circumference of the neck. In some embodiments, this distance must correspond to the distance between inner parts of compression members of a compression device for compressing carotid arteries. This measurement may be essential to establish adequate distance between the right and left compression members in order to assure adequate, precise, and/or selective compression of carotid arteries 16, and to position the compression members over the course of the arterial groove of the carotid artery 16, i.e., between the trachea 34 medially and muscle(s) 420 laterally. Similar principles may be applied for positioning compression members for the compression of vertebral arteries 12, where the arteries are compressed by compression members positioned in the groove between the neck muscles 36, such as a scalenus muscle laterally and the spine 37 and the transverse process of the spine 425 medially and posteriorly, and the longus colli muscle medially. For easier measurement, a set of templates (sizers) can be used. A template (sizer) can be applied to the anterior surface of the neck for better estimation of the distance between the carotid arteries and the corresponding carotid compression members, and/or for better estimation of the distance between the vertebral arteries and the corresponding vertebral compression members. Such templates may be part of a kit for carotid and/or vertebral compression. Before an emboligenic procedure, a patient can be measured with one or more of the templates to determine the inter-carotid distance (or inter-vertebral distance), and an appropriately-sized neck collar having appropriate distance between the compression members can then be chosen for use on the patient.

FIG. 34 illustrates the concept of "carotid bridging." Carotid bridging refers to a situation where a compression member is substantially longer than a gap that is formed between a lateral wall of the trachea 34 and an adjacent muscle 405 (e.g., sternocleidomastoid muscle) on one or both sides of the neck. For example, line 550 of FIG. 34 illustrates a straight plane between trachea 34 and a muscle 405 (e.g., sternocleidomastoid muscle). The gap can correspond to the width of an arterial groove, where a compression member of a specific cross-sectional shape is supposed to enter to achieve compression of a target artery. Hinge point 535 illustrated in FIG. 34 represents a point at the front of the trachea from which intersects a straight plane between a medial structure (e.g., trachea 34) and a lateral structure (e.g., sternocleidomastoid, scalenus, longus colli, and/or other neck muscles) on either side of the neck. Angle 555 represents an angle between the two planes that intersect hinge point 535. The cross-sectional shapes, sizes, combinations, and/or configurations of compression members disclosed herein are designed to fill the gap between one or more medial structures, such as trachea 34, and one or more lateral structures, such as muscle 405 (e.g., sternocleidomastoid, scalenus, longus colli muscles, and/or other neck muscles). However, if the width of the compression member is substantially longer than the width of the groove, the member may not be able to reach a target artery at the bottom of the groove. Accordingly, the compression member may act as a bridge over the artery, such as a carotid artery 12, resting on trachea 34 medially and one or more muscles 405 (e.g., SCM and/or other neck muscles such as scalenus and longus colli muscles) laterally with the artery located deeper, where it cannot be reached to achieve adequate compression. For example, a distance 540, 545 between the skin 515 of the patient's neck and the artery 16 may be such that a compression member wider than the gap between a medial structure (e.g., trachea 34) and a lateral structure (e.g., sternocleidomastoid, scalenus, longus colli, and/or other neck muscles) cannot compress artery 16 without much higher pressures, which could cause the degree of trauma to surrounding organs and structure to be much more significant. Similar principles may apply to the compression of the vertebral artery 12 and the repetition of these details is not necessary.

FIG. 35 illustrates an example of a "tracheal hinge," and an example of an "angle of hinging." As shown in FIG. 35, a hinge ("tracheal hinge") may be provided at a location in the compression device so that, when placed at the neck of a patient, the hinge is located at, or within a short distance (e.g., within 1 centimeter) of, the hinge point (e.g., hinge point 535 of FIG. 34) to address possible issues of carotid bridging as discussed with respect to FIG. 35. For example, A of FIG. 35 illustrates a circular compression member 565 placed at the skin 515 of the neck of a patient. As can be seen from A of FIG. 35, carotid bridging of the compression device occurs between a medial structure (e.g., trachea 34) and a lateral structure (e.g., sternocleidomastoid, scalenus, longus colli, and/or other neck muscles 405), causing the compression member 565 to be a distance a 570 from target artery 16. Hinge point 560 of FIG. 35 corresponds to the point at which planes extending from the medial structure to the lateral structure on either side of the neck would intersect.

As illustrated in B of FIG. 35, the possible issues of carotid bridging of FIG. 34 and A of FIG. 35 can be resolved by providing a hinge 575 in the compression device. Hinge 575 may be placed at a location of the compression device so, when the compression device is aligned with a patient's neck, hinge 575 is at the hinge point 560, or within a short distance (e.g., 1 centimeter) of hinge point 560. Hinge 575 of the compression device may allow an angle 580 of hinging to be controlled by an operator of the compression device (e.g., a doctor, nurse) to achieve optimal compression of an artery 16 (e.g., carotid and/or vertebral artery), while preventing undue compression of trachea 34 and esophagus 35 medially and jugular vein laterally. A forward prominence of trachea 34 may ordinarily prevent a circular compression mechanism, such as a neck collar, from adequate compression of a carotid artery that is running much deeper in a vascular groove. Therefore, it may be useful to utilize a hinging mechanism, such as hinge 575, in order to create a particular angle between left and right extensions of a carotid compression device carrying compression members. This angle may, for example, be between 70 and 130 degrees at the trachea, providing for better contact between the carotid and/or vertebral compression members and the underlying arteries. In some embodiments, if the angle is greater than 130 degrees, or less than 70 degrees, a target artery may not be adequately compressed. However, in some embodiments, the angle at the hinge may be between 35 degrees and 140 degrees when the compression members are actuated.

To achieve a certain angle with a hinging mechanism, such as hinge 575, a special compliant and flexible part in an anterior segment of the compression collar may be used. The anterior segment of the compression collar may be free of compression members and/or rigid components. The anterior segment of the compression collar may also be capable of avoiding a convex arch aimed anteriorly over an anterior surface of a patient's neck. Without such a hinge or a compliant portion of the compression device, the compression device may form an arch externally, thereby preventing inward compression of a target artery in a vascular groove. Conversely, a hinge, or an angle of the compression device, that is between 70 degrees and 130 degrees, may allow for a deeper position of a carotid and/or vertebral compression member in a vascular groove and therefore closer contact and more selective and efficient compression of an artery (e.g., carotid artery 16, vertebral artery 12). Such a curvature would assure a more direct contact between the compression members and carotid artery and/or vertebral artery groove and may prevent a bridging effect of a neck compression device (as previously described) that would prevent optimal compression of a target artery. For example, B of FIG. 35 illustrates that, as a result of the hinging mechanism (e.g., hinge 575), the distance 590 between a compression member 585 of a compression device and a target artery 16 is less than the distance 570 between compression member 565 of a compression device and target artery 16.

Figure 36:
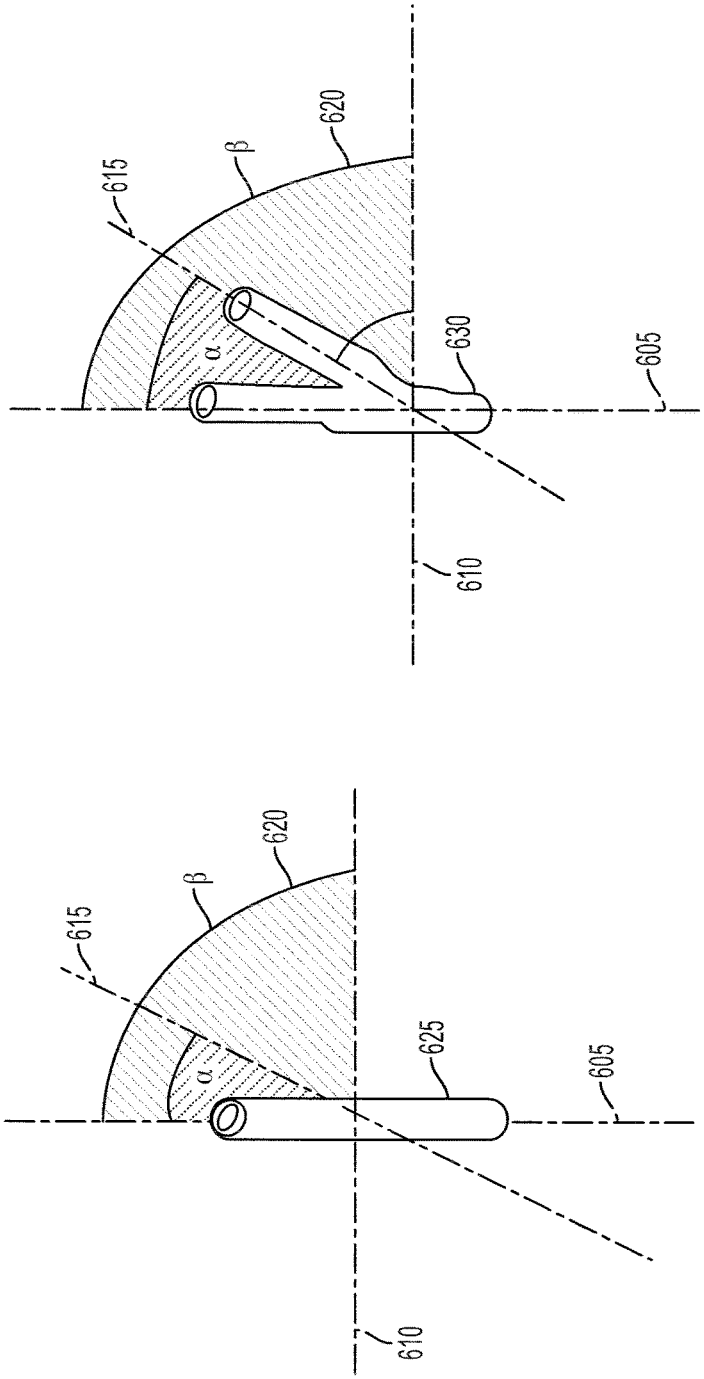
FIG. 36 illustrates an example of a range of angles of crossing of the course of a target blood vessel by a compression member in relation to a longitudinal axis of a target vessel.

FIG. 36 illustrates an example mechanism of optimizing bilateral carotid compression using a particular range of angles α 615-β 620 between a longitudinal axis of a target carotid artery and/or vertebral artery and a longitudinal axis of a compression member. For example, in some embodiments, a compression member of a compression device may be angled such that, when positioned and compressed against a neck of a patient, a particular angle is formed between a longitudinal axis of the compression member and a longitudinal axis 605 of a target artery 625. In some embodiments, the angle may be between 0 degrees and 65, as contact between a compression member and an underlying carotid 16 or vertebral 12 artery may require the least amount of pressurization or compression at these angles, and may therefore be most efficient and/or safe at these angles. In some embodiments, the angle between a longitudinal axis of a compression member and a longitudinal axis of a target artery may be between 30 degrees and 65 degrees to assure a desired compression of a carotid and/or vertebral artery even if an anatomical position of the carotid and/or vertebral artery cannot be ascertained (such as in a patient with a short and/or thick neck).

In some embodiments, a vascular probe (e.g., a pulse oximeter and/or Doppler probe) can be added to the inner surface of a compression member, or to an inner surface of the neck collar. The vascular prove could facilitate a search for a target artery and document a correct position of a compression member and/or an adequacy of arterial compression. Moreover, in some embodiments, a vascular Doppler probe may detect embolic particles inside the artery, by registering the high intensity transient signals (HITS) from the carotid arteries 16 and/or vertebral arteries 12 (analogous to the detection of embolic signals by transcranial Doppler) thus prompting the compression device to get actuated and to compress said arteries for prevention of cerebral emboli. Such actuation may be achieved automatically according to the feedback mechanism described above (FIGS. 3-7), or on the command by a health provider once the emboli passing through the arteries are detected.

Figure 37A:
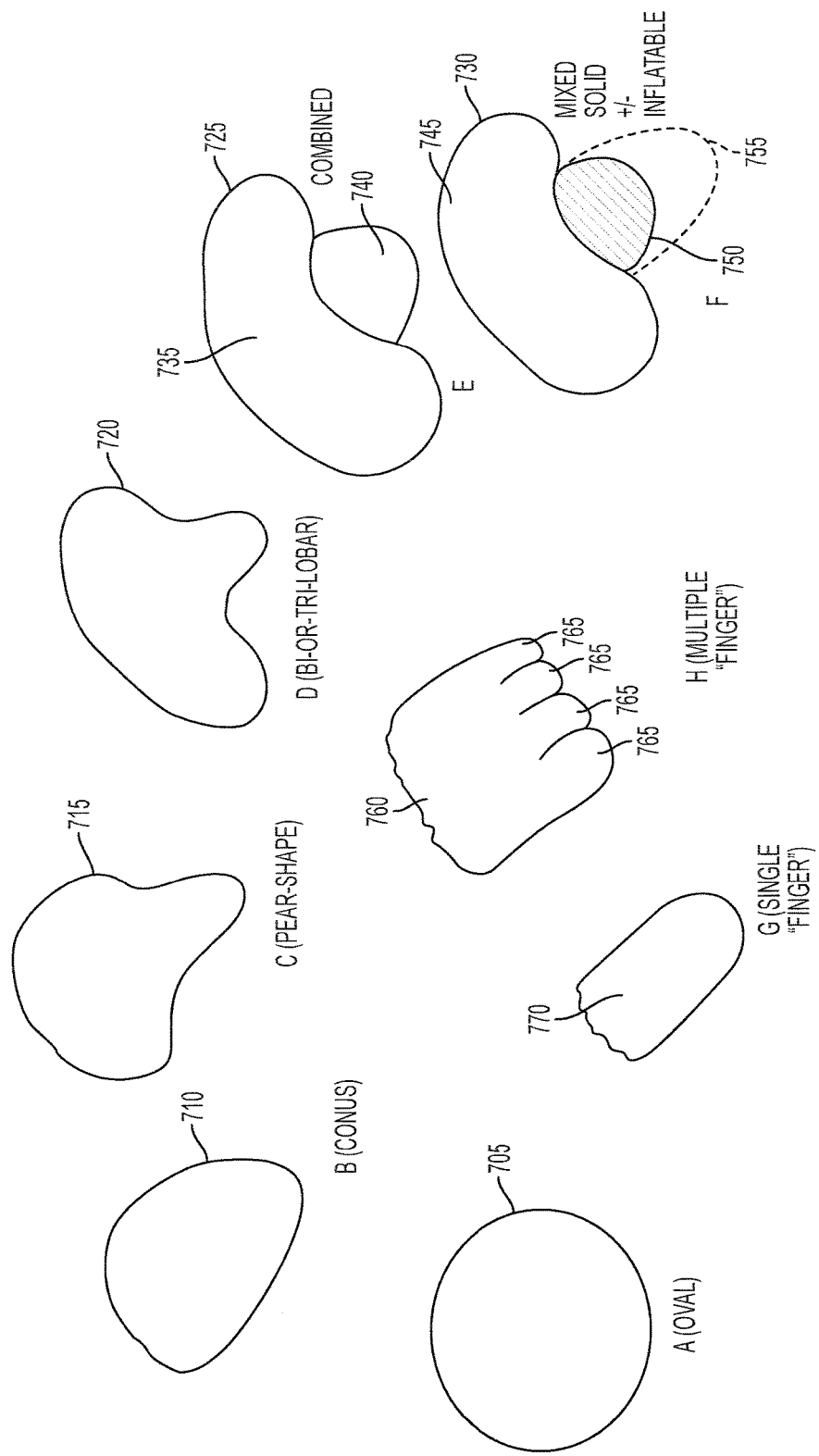
FIG. 37A illustrates an example of compression members of different cross-sectional shapes and size as a part of an example compression kit.
Figure 37B:
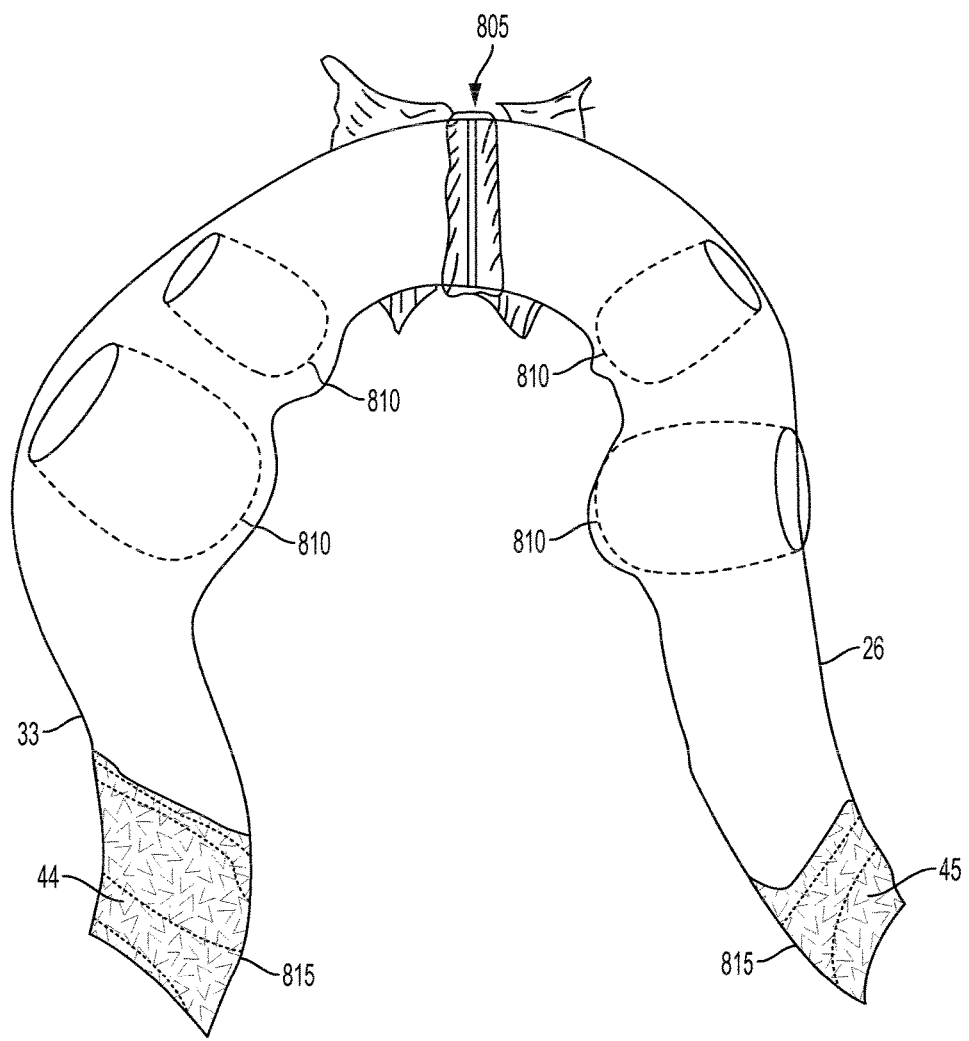
FIG. 37B illustrates an example of an adjustable neck collar for compression of extracranial cerebral arteries as a part of an example compression kit.
Figure 37C:
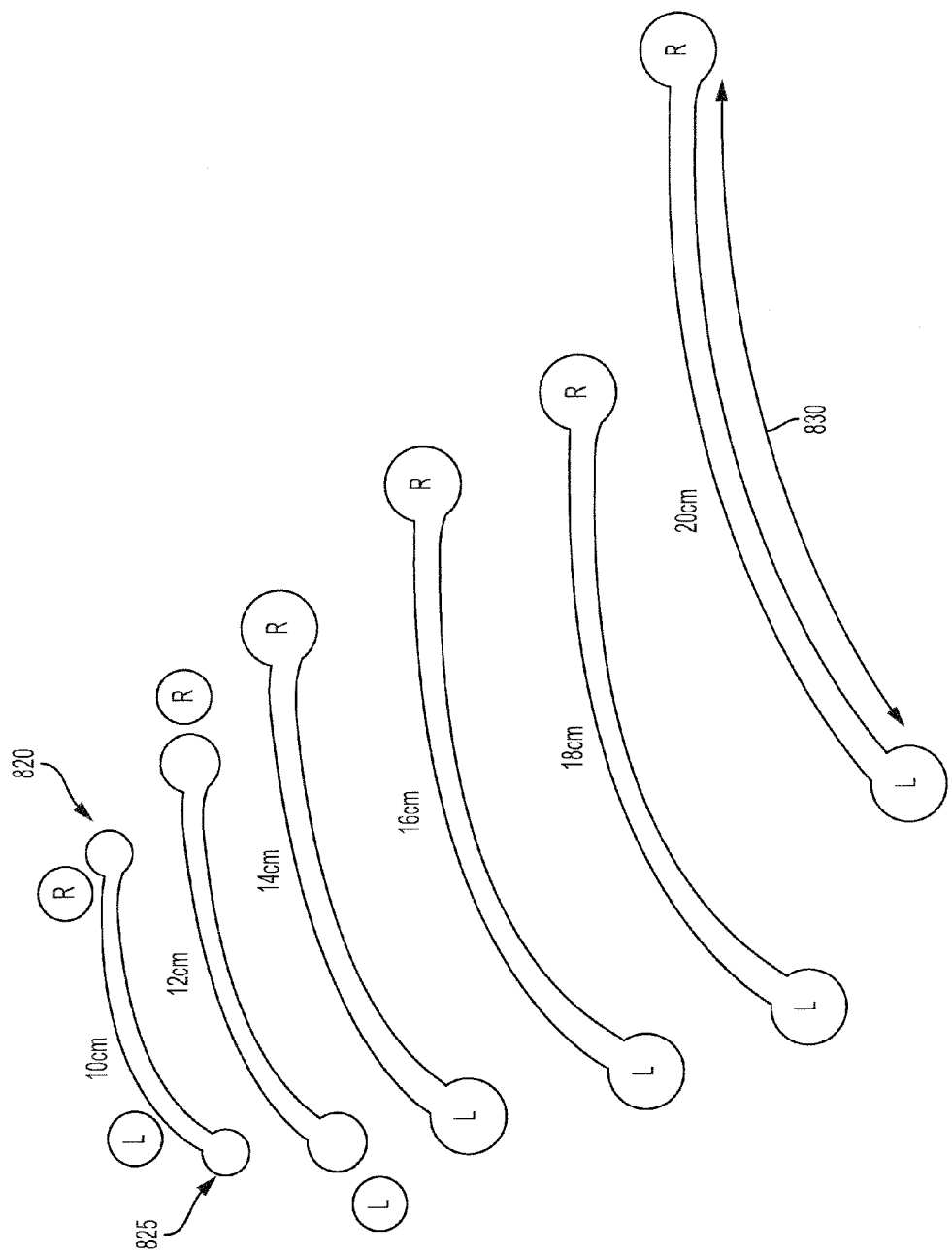
FIG. 37C illustrates an example of neck sizing templates for measuring the distance between arteries of a patient as a part of an example compression kit.
Figure 38:
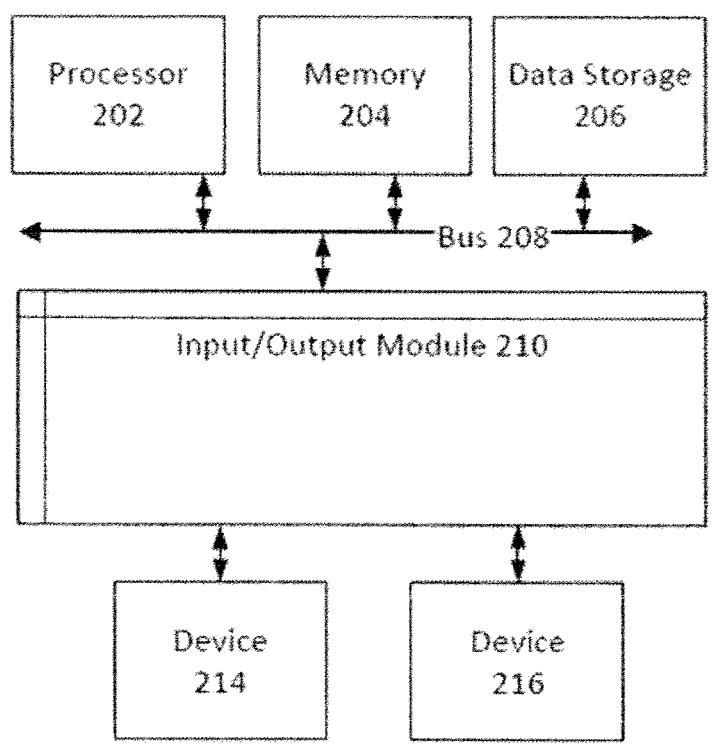
FIG. 38 is an example block diagram illustrating a system of the subject technology.
Figure 39:
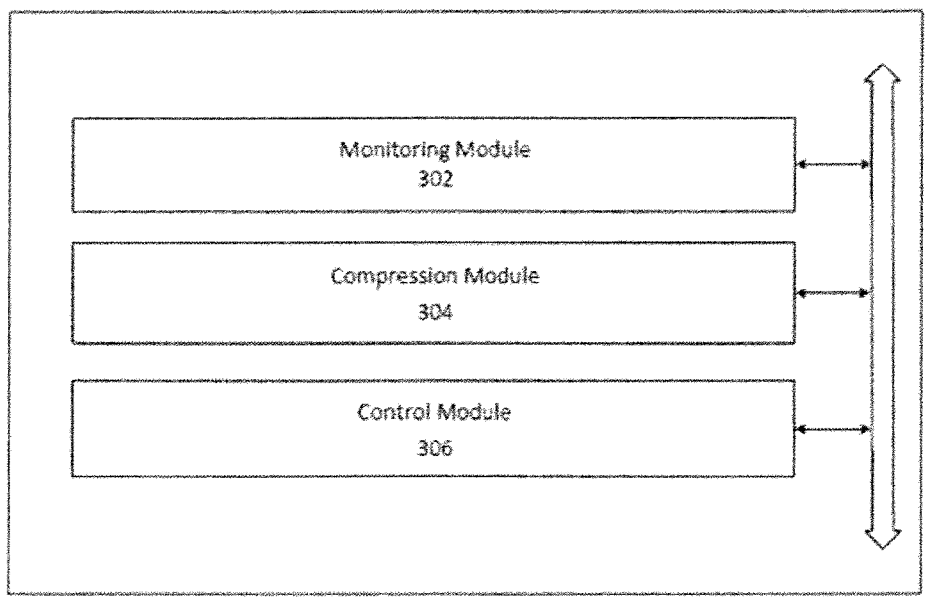
FIG. 39 is an example diagram illustrating modules implementing methods of the subject technology.

FIGS. 37A-C illustrate example parts of a carotid and/or vertebral compression kit. For example, as illustrated in FIG. 37A, kit may include a range of one or more compression members. The compression members may have different cross-sectional shapes and/or sizes. One or more compression members having different cross-sectional shapes may be included in a kit and may include, for example, a compression member having a cross-sectional shape that is oval shape 705, conic (or conus) shape 710, pear shape 715, bilobar or trilobar shape 720, combined shape 735 combining two shapes 725 and 750, mixed solid and inflatable shape 730 having a solid compression member 745 and an inflatable compression member that expands from an unexpanded configuration 750 to an expanded configuration 755, a multiple finger shape 760 having multiple finger shapes 765, a single finger shape 770, or any other shape that would allow a majority of a force of compression to be delivered to an artery, with lesser forces being applied to structures proximate to the artery. Additionally, different sized compression members may be provided for use on patient's having differing neck anatomies. For example, smaller sized compression members may be provided for use on individuals with smaller necks (e.g., children), while larger sized compression members may be provided for use on individual with larger necks (e.g., adults with large necks). In some embodiments, the compression members, such as those illustrated in FIG. 37A, may comprise foam. In some embodiments, the compression members, such as those illustrated in FIG. 37A, may be expandable members that inflate when pressurized. In some embodiments, some of the compression members illustrated in FIG. 37A may comprise foam, while others may be expandable. The cross-sectional shapes for one or more of the compression members illustrated in FIG. 37A may be the compression members cross-sectional shape when at rest and/or when actuated. Providing a kit with different cross-sectional shapes and/or sizes may allow an individual (e.g., doctor, nurse) fitting a patient with the compression device to select a cross-sectional shape and/or size of one or more compression members that achieves the most anatomically congruent fit into an arterial groove of a carotid 16 and/or vertebral 12 artery. Such a selection for a particular case can be based on a neck exam, or a neck CT scan, which allows the delineation of the precise neck anatomy of a particular patient.

As illustrated in FIG. 37B, the kit may include one or more adjustable compression devices, such as adjustable neck compression collars. One or more of the compression devices may include one or more pockets (e.g., insertion pockets) and/or attachments 810 that allow for placement and removal of compression members. The compression devices may be differently sized, such that the pockets and/or attachments are spaced differently from one compression device to another, allowing differential spacing of compression members depending on the compression device selected for use. A compression device may include straps 26, 33 for encircling the compression device around a patient's neck. A compression device may also include attachment patches 44, 45 (e.g., hook and loop fastener), which allow the compression device to be secured around a patient's neck. In some embodiments, a compression device can be tightened or loosened (e.g., with a loop) so that a single compression device can be used for patients having necks of slightly different size. A compression device may also include a hinge, which may allow an angle of the two sides of the compression device to be adjusted, such as that discussed with reference to FIGS. 34 and 35. A compression device may also include a buckle 805, which may provide an option to increase a length of the device to extend the inter-carotid distance between the compression members, or to tighten the collar to decrease the inter-carotid distance between the compression members.

As illustrated in FIG. 37C, the kit may include one or more neck sizing templates. The neck sizing templates may have different sizes and curvatures, and may allow an individual to measure a distance between a right and left carotid artery over an anterior neck surface of a patient. The templates may be made out of any type of material, such as plastic, metal, wood, or paper. To measure the distance between carotid arteries or vertebral arteries of a patient, a right side (R) 820 may be aligned with a right artery (e.g., carotid artery 16, vertebral artery 12), and a left side (L) 825 may be aligned with a left artery (e.g., carotid artery 16, vertebral artery 12). Each of the templates may have a defined size, so that when left and right ends of a particular template align with the left and right carotid or vertebral arteries of a patient, the inter-carotid or inter-vertebral distance will be known. Alternatively, an adjustable template may be provided with measurements along the template, where the template can expand or contract to align with the patient's carotid and/or vertebral arteries in order to provide a measurement of the distance between the arteries.

A kit, such as the example kit described above with respect to FIGS. 37A-C, may be designed to fulfill a doctor's demand at any particular situation when there is a need for selecting an optimal cross-sectional shape and/or curvature of a compression device, and an optimal cross-sectional shape and/or size of one or more carotid and/or vertebral compression elements for a particular patient, depending on the size, curvature, thickness, and/or anatomy of the patient's neck. For example, for a patient with a larger neck and/or a wider inter-carotid (or inter-vertebral) distance as measured with a template, a larger compression device, such as a compression collar with a larger distance between compression members may be chosen. Conversely, for a patient with a thinner neck and/or a smaller inter-carotid distance as measured with a template, a narrower compression device with a lesser distance between compression members may be chosen.

A neck compression device, such as a neck compression collar, may have an option for adjusting its length and a distance between compression members using an anterior and/or posterior strap, connecting two halves of the circumferential neck collar anteriorly or posteriorly.

One or more of the compression members used in the neck compression collar may be actuated by virtue of insufflation of air, gas, and/or fluid, and may be in a fluid continuity with a pressure source that is activated and released on-demand. In other embodiments, compression members may be solid or partially compliant components, or a combination of solid, partially compliant (e.g., foam), and/or other components, for better compression of underlying arteries.

Further, although shown as employing a single pressure source 49, it is to be understood that multiple pressure sources of different types may be used. For instance, the transverse carotid expandable member 32 may be pressurized by a first pressure source 49 such as a pump, tightening or direct compressing mechanism while a second source of pressure of similar types is included in the device 26 to provide pressure to the two longitudinal vascular compression members 27 and 46.

A monitoring system 58 may be included with the device 26 to assure a safe, adequate, easily manageable and controllable compression of carotid, vertebral and other vessels. The monitoring system 58 may comprise Doppler ultrasound, Doppler probe, oscillotonometry, electroencephalography, transcranial Doppler, echocardiography, cerebral oximetry and/or other techniques. The device 26 may be actuated to such a degree that the one, two or more areas of vascular compression formed completely stop the flow of blood into the distal artery such as carotid artery 22, or to an extent that partial flow of blood passes through the areas of compression 23 and into the distal artery such as carotid artery 22.

The device 26 provided is a noninvasive and precise apparatus with an option of assessing a degree and an effectiveness of an interruption of the arterial flow by the optional inclusion of a monitoring system 58. The device 26 assures a uniform and reproducible interruption or limitation of the arterial flow bilaterally minimizing the risk of trauma to the artery compressed such as carotid and vertebral artery and subsequent distal emboli, such as cerebral emboli 17. An alarm system 59 can be included in the device 26 that is triggered by excessive or lengthy compression of the target artery, such as carotid arteries 16, brachial or femoral arteries. In addition the alarm may be triggered by the appearance of the potential vascular emboli in the vessels of interest. Such an appearance may be detected by the vascular Doppler, analogous to the transcranial Doppler, or by thoracic or transesophageal echocardiography (ECHO) that would show echogenic signals inside the vessels, representing potential emboli. The alarm system 59 may be a part of the monitoring system 58 or may be a different component that is not part of the monitoring system 58. The alarm system 59 may thus measure the time of compression, and the magnitude of compression. Constant monitoring of arterial, such as carotid 16, brachial or femoral and systemic arterial and device 26 pressures with pressure in the device 26 exceeding only slightly the pressure in the arterial system may be conducted to ensure safe operation and use of the disclosed device 26. The device 26 provides a noninvasive compression apparatus that does not require the insertion of intravascular devices.

A method for reducing or totally preventing cerebral emboli will now be discussed. A brief compression of arteries to be protected from emboli, such as carotid arteries 16 and vertebral arteries 12 by way of a device 26 may be performed first to assure adequate position of the device leading to reduction or interruption of flow or pulse through said artery as assessed by carotid Doppler, a pressure gauge, percutaneous cerebral oximetry or transcranial Doppler.

Once an adequate position of the device 26 is confirmed, the pressure in the vascular compression components (27, 32, 46 and/or 27-V, 32-V, 46-V) is released and the apparatus 26 is ready for use. The device 26 is inflated to the pressure exceeding patient's systemic pressure just before proceeding with the emboligenic part of the procedure. Adequate compression of the target arteries such as carotid arteries 16 will lead to divergence of blood and emboli away from the vessels to be protected and toward more distal less important arteries, thus decreasing the risk of deadly complications, such as stroke.

The pressure in the device 26, and thus to the vascular compression components 27, 32, 46 and/or 27-V, 32-V, 46-V is released after the emboligenic procedure is completed after a full washout of potential emboli 20, 18 from the heart 11, thoracic aorta and all other potential sources. The pressurization of the device 26 and its different compartments can be repeated any time and on multiple occasions when the emboligenic intervention is contemplated.

Should the physician or physician's assistant forget to release arterial compression timely, an alarm would go off and the pressure would be released spontaneously to avoid undue interruption of the arterial flow. The alarm and deflation could be overridden by the physician when clinically indicated. The alarm may be sounded by the alarm system 59, and the deflation may be activated by the pressure source 49 and/or the alarm system 59 and/or the monitoring system 58.

The central axis 56 may be present even when the device 26 is not configured with straps 33, 43 to form a generally circular member when viewed from the top as for example in FIG. 6A. In some embodiments of the device 26, a circular member is not formed when viewed from the top by the straps 33, 43. For instance, the straps 33, 43 may be missing such that the section 31 is attached to sides of a bed or otherwise secured so that the device 26 is located at the neck of the patient. In such instances, the central axis 56 is still present. The central axis 56 may be located at a location within the neck of the patient, for examples shown with reference to FIGS. 8A and 8B. This location may be at the spinal column 37 of the patient, or may be at the center of the neck of the patient. It is to be understood that various embodiments of the device 26 exist in which the device 26 does not wrap completely around the neck of the patient but instead only wraps around a portion of the neck of the patient less than 360 degrees fully about the neck of the patient.

The apparatus and methods discussed herein are not limited to the detection and compression of any particular vessels or combination of vessels, but can include any number of different types of vessels. For example, in some aspects, vessels can include arteries or veins. In some aspects, the vessels can be suprathoracic vessels (e.g., vessels in the neck or above), vessels in the thorax, vessels in the abdominal area or below, vessels to the sides of the thorax such as vessels in the shoulder area and beyond), blood vessels of the upper and lower extremities, or other types of vessels and/or branches thereof.

In some aspects, the detection and compression systems disclosed herein can be applied to suprathoracic vessels. The suprathoracic vessels can comprise at least one of intracranial vessels, cerebral arteries, and/or any branches thereof. For example, the suprathoracic vessels can comprise at least one of a common carotid artery, an internal carotid artery, an external carotid artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, an anterior, middle, and/or posterior cerebral artery, a superior cerebellar artery, a basilar artery, a left internal acoustic (labyrinthine) artery, an anterior inferior cerebellar artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels can also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels can also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels can also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels can also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The vessels can comprise the aorta, pulmonary artery, or branches thereof. For example, the vessels can comprise at least one of an ascending aorta, a descending aorta, an arch of the aorta, and/or branches thereof. The descending aorta can comprise at least one of a thoracic aorta, and/or any branches thereof. The vessels can also comprise at least one of a subclavian artery, pulmonary artery, a brachiocephalic trunk, and/or a pulmonary artery.

In some aspects, the vessels can also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the vessels can comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, iliac arteries or veins, femoral arteries or veins, popliteal arteries or veins, tibial arteries and veins, and saphenous veins, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, and/or branches thereof. The vessels can also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, (obturator anastomotic) branches of inferior epigastric artery, a left colic artery, rectal arteries, and/or branches thereof.

In some aspects, the vessels can comprise at least one of humeral arteries, a transverse cervical artery, a suprascapular artery, a dorsal scapular artery, and/or branches thereof. The vessels can also comprise at least one of an anterior circumflex humeral artery, a posterior circumflex humeral artery, a subscapular artery, a circumflex scapular artery, a brachial artery, a thoracodorsal artery, a thoracic artery, an inferior thyroid artery, a thyrocervical trunk, a subclavian artery, a superior thoracic artery, a thoracoacromial artery, and/or branches thereof.

In some aspects, vessels can include other portions of the vasculature, such as the heart or chambers of the heart. In some aspects, the detection and compression systems disclosed herein can be applied to the heart or chambers of the heart, such as the right atrium, the left atrium, the right ventricle, and/or the left ventricle. For example, detection of emboli can be performed within or near one or more chambers of the heart.

In some aspects, a vessel in which detection is performed is different from a vessel in which compression is performed. For example, detection is performed in a first vessel and compression is performed in a second vessel. The second vessel can be downstream of the first vessel.

In some aspects, a vessel in which detection is performed is the same as a vessel in which compression is performed. For example, detection is performed in a vessel at a first location and compression is performed in the vessel at a second location. The second location can be downstream of the first location.

FIG. 25 is a block diagram illustrating an exemplary computer system 200 with which a system (e.g., monitoring module/system and/or detection module/system) of the subject technology can be implemented. In certain embodiments, the computer system 200 may be implemented using hardware or a combination of software and hardware, either in a dedicated server, or integrated into another entity, or distributed across multiple entities.

The computer system 200 includes a bus 208 or other communication mechanism for communicating information, and a processor 202 coupled with the bus 208 for processing information. By way of example, the computer system 200 may be implemented with one or more processors 202. The processor 202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, and/or any other suitable entity that can perform calculations or other manipulations of information.

The computer system 200 can include, in addition to hardware, code that creates an execution environment for the computer program in question, e.g., code that constitutes processor firmware, a protocol stack, a database management system, an operating system, or a combination of one or more of them stored in an included memory 204, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, and/or any other suitable storage device, coupled to the bus 208 for storing information and instructions to be executed by the processor 202. The processor 202 and the memory 204 can be supplemented by, or incorporated in, special purpose logic circuitry.

The instructions may be stored in the memory 204 and implemented in one or more computer program products, i.e., one or more modules of computer program instructions encoded on a computer readable medium for execution by, or to control the operation of, the computer system 200, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and/or application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and/or xml-based languages. The memory 204 may also be used for storing temporary variable or other intermediate information during execution of instructions to be executed by the processor 202.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

The computer system 200 further includes a data storage device 206 such as a magnetic disk or optical disk, coupled to the bus 208 for storing information and instructions. The computer system 200 may be coupled via an input/output module 210 to various devices (e.g., devices 214 and 216). The input/output module 210 can be any input/output module. Exemplary input/output modules 210 include data ports (e.g., USB ports), audio ports, and/or video ports. In some embodiments, the input/output module 210 includes a communications module. Exemplary communications modules include networking interface cards, such as Ethernet cards, modems, and routers. In certain aspects, the input/output module 210 is configured to connect to a plurality of devices, such as an input device 214 and/or an output device 216. Exemplary input devices 214 include a keyboard and/or a pointing device (e.g., a mouse or a trackball) by which a user can provide input to the computer system 200. Other kinds of input devices 214 can be used to provide for interaction with a user as well, such as a tactile input device, visual input device, audio input device, and/or brain-computer interface device. For example, feedback provided to the user can be any form of sensory feedback (e.g., visual feedback, auditory feedback, and/or tactile feedback), and input from the user can be received in any form, including acoustic, speech, tactile, and/or brain wave input. Exemplary output devices 216 include display devices, such as a cathode ray tube (CRT) or liquid crystal display (LCD) monitor, for displaying information to the user.

According to certain embodiments, the computer system 200 can operate in response to the processor 202 executing one or more sequences of one or more instructions contained in the memory 204. Such instructions may be read into the memory 204 from another machine-readable medium, such as the data storage device 206. Execution of the sequences of instructions contained in the memory 204 causes the processor 202 to perform the process steps described herein. One or more processors in a multi-processing arrangement may also be employed to execute the sequences of instructions contained in the memory 204. In some embodiments, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component (e.g., a data server), or that includes a middleware component (e.g., an application server), or that includes a front end component (e.g., a client computer having a graphical user interface and/or a Web browser through which a user can interact with an implementation of the subject matter described in this specification), or any combination of one or more such back end, middleware, or front end components. The components of the system 200 can be interconnected by any form or medium of digital data communication (e.g., a communication network). Examples of communication networks include a local area network and a wide area network.

The term "machine-readable storage medium" or "computer readable medium" as used herein refers to any medium or media that participates in providing instructions to the processor 202 for execution. Such a medium may take many forms, including, but not limited to, non-volatile media, volatile media, and transmission media. Non-volatile media include, for example, optical or magnetic disks, such as the data storage device 206. Volatile media include dynamic memory, such as the memory 204. Transmission media include coaxial cables, copper wire, and fiber optics, including the wires that comprise the bus 208. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, a "processor" can include one or more processors, and a "module" can include one or more modules.

In an aspect of the subject technology, a machine-readable medium is a computer-readable medium encoded or stored with instructions and is a computing element, which defines structural and functional relationships between the instructions and the rest of the system, which permit the instructions' functionality to be realized. Instructions may be executable, for example, by a system or by a processor of the system. Instructions can be, for example, a computer program including code. A machine-readable medium may comprise one or more media.

FIG. 26 illustrates an example of a system 300 for diverting emboli within a patient, in accordance with various embodiments of the subject technology. The system 300 is an example of an implementation of a system for diverting emboli within a patient. The system 300 comprises monitoring module 302, compression module 304, and control module 306. Although the system 300 is shown as having these modules, the system 300 may have other suitable configurations. The modules of the system 300 may be in communication with one another. In some embodiments, the modules may be implemented in software (e.g., subroutines and code). For example, the modules may be stored in the memory 204 and/or data storage 206, and executed by the processor 202. In some aspects, some or all of the modules may be implemented in hardware (e.g., an Application Specific Integrated Circuit (ASIC), a Field Programmable Gate Array (FPGA), a Programmable Logic Device (PLD), a controller, a state machine, gated logic, discrete hardware components, or any other suitable devices) and/or a combination of both. Additional features and functions of these modules according to various aspects of the subject technology are further described in the present disclosure.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multichip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles define herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

Reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A device for diverting emboli from a cerebral circulation of a patient, comprising: a first compression member configured to be applied to a first artery of the patient when the device is placed around a neck of the patient, the first compression member having unactuated state and an actuated state, wherein the first compression member has an anatomically congruent cross-sectional shape configured such that, when in the actuated state, the first compression member applies a greater amount of force on the first artery than on a trachea or a sternocleidomastoid muscle of the patient, and wherein in the actuated state the first compression member is narrower at one end and wider at another end, and wherein the first compression member is configured to self-position in an anatomical groove of the neck of the patient where the first artery is located and to spread surrounding structures of the first artery and orient and stabilize the first compression member over the first artery, and wherein the first compression member in the actuated state is configured to direct a main force into the first artery to compress the first artery and smaller force into the surrounding structures;

a second compression member configured to be applied to a second artery of the patient when the device is placed around the neck of the patient, the second compression member having air unactuated state and an actuated state, wherein the second compression member has an anatomically congruent cross-sectional shape configured such that, when in the actuated state, the second compression member applies a greater amount of force on the second artery than on the trachea or a sternocleidomastoid muscle of the patient.

2. The device of claim 1, wherein a cross sectional shape of the first compression member is one of an oval shape, a conic shape, a pear shape, a bilobar shape, a trilobar shape, a finger shape or a multiple finger shape.

3. The device of claim 2, wherein the first compression member assumes the cross-sectional shape when in its actuated state.

4. The device of claim 1, wherein the second compression member comprises two compression members, a first of the two compression members having an arcuate or crescent cross-sectional shape, and a second of the two compression members having a conic, oval, or pear cross-sectional shape, wherein the second of the two compression members extends from an arcuate or crescent shaped surface of the first of the two compression members towards the artery such that both the arcuate or crescent shaped surface and the second of the two compression members are configured for engaging the neck.

5. The device of claim 1, wherein at least one of the first compression member or the second compression member comprises foam.

6. The device of claim 1, wherein at least one of the first compression member or the second compression member is inflatable.

7. The device of claim 1, wherein the device has a hinge positioned between the first compression member and the second compression member, wherein the hinge is configured to be actuated to adjust one of a distance between the first compression member and the first artery and a distance between the second compression member and the second artery.

8. The device of claim 7, wherein the hinge can be actuated to adjust an angle formed by the hinge between a side of the device comprising the first compression member and a side of the device comprising the second compression member, wherein the angle is between 35 degrees and 140 degrees when the first compression member and the second compression member are in their actuated states.

9. The device of claim 1, wherein the first compression member is disposed in an insertion pocket of the device, the insertion pocket being adapted for removal of the first compression member and insertion of a third compression member that is different in shape than the first compression member.

10. The device of claim 1, wherein the first artery is a carotid artery.

11. The device of claim 1, wherein the first compression member includes a Doppler probe configured to detect embolic particles in the first artery.

12. The device of claim 1, wherein the first compression member includes one of a Doppler probe or a pulse oximeter configured to detect a correct amount of compression on the first artery.

13. The device of clan 1, wherein the first compression member has a cross-sectional multiple finger shape and is configured to compress along a length of the first artery.

14. The device of claim 1, wherein the first compression member, when actuated, is configured to exert pressure onto the trachea and the sternocleidomastoid muscle so as to stabilize the first compression member on the first artery.

15. The device of claim 1, wherein the device is configured to be positioned adjacent to the trachea, and the portion of the device adjacent to the trachea is narrower in a longitudinal direction parallel to the longitudinal axis of the neck than a portion of the device including the first compression member.

16. The device of claim 1, wherein an angle between a longitudinal axis of the first artery and a longitudinal axis of the first compression member is between 0 and 65 degrees when the first compression member is in its actuated state.

17. A device for diverting emboli from cerebral circulation of a patient, comprising: a first compression member configured to be applied to a first artery of the patient when the device is placed around a neck of the patient, the first compression member having an unactuated state and an actuated state, wherein the first compression member has an anatomically congruent cross-sectional shape configured such that, when in the actuated state, the first compression member applies a greater amount of force on the first artery than on a trachea or a sternocleidomastoid muscle of the patient;
  a second compression member configured to be applied to a second artery of the patient when the device is placed around the neck of the patient, the second compression member having an unactuated state and an actuated state, wherein the second compression member has an anatomically congruent cross-sectional shape configured such that, when in the actuated state, the second compression member applies a greater amount of force on the second artery than on the trachea or a sternocleidomastoid muscle of the patient;
  a third compression member configured to be applied to a third artery of the patient when the device is placed around the neck of the patient, the third compression member having an unactuated state and an actuated state, wherein the third compression member has an anatomically congruent cross-sectional shape configured such that, when In the actuated state, the third compression member applies a greater amount of force on the third artery than on a longus colli muscle, a scalenus anterior muscle, and a sternocleidomastoid muscle of the patient; and
  a fourth compression member configured to be applied to a fourth artery of the patient when the device is placed around the neck of the patient, the fourth compression member having an unactuated state and an actuated state, wherein the fourth compression member has an anatomically congruent cross-sectional shape configured such that, when in the actuated state, the fourth compression member applies a greater amount of force on the fourth artery than on a longus colli muscle, a scanelus anterior muscle, and a sternocleidomastoid muscle of the patient.

18. The device of claim 17, wherein the third artery is a vertebral artery.

19. A method of diverting emboli from cerebral circulation of a patient, comprising:
  determining an anatomical characteristic of a neck of the patient;
  selecting a compression member having a particular cross-sectional shape from a plurality of compression members based on the characteristic;
  coupling the compression member to a compression device;
  positioning the compression member at an artery of the patient by positioning the compression device around the neck of the patient; and
  actuating the compression member to compress the artery, wherein when actuated the compression member is narrower at one end and wider at another end, and wherein when actuated the compression member self-positions in an anatomical groove of the neck of the patient where the artery is located and spreads surrounding structures of the artery and orients and stabilizes the compression member over the artery.

20. A method of diverting emboli from a cerebral circulation of a patient, comprising:
  placing a compression device around a neck of the patient, such that a compression member attached to the compression device is positioned for application of pressure to an artery; and
  actuating the compression member to apply force to the artery, wherein an amount of the force applied by the compression member to the artery is greater than an amount of force applied by the compression member to a trachea or a sternocleidomastoid muscle of the patient, wherein when actuated the compression member is narrower at one end and wider at another end, and wherein when actuated the compression member self-positions in an anatomical groove of the neck of the patient where the artery is located and spreads surrounding structures of the artery and orients and stabilizes the compression member over the artery, and wherein when actuated the first compression member directs a main force into the first artery to compress the first artery and smaller force into the surrounding structure.

* * * * *

UNITED STATES PATENT AND TRADEMARK OFFICE
CERTIFICATE OF CORRECTION

| | |
|---|---|
| PATENT NO. | : 10,258,348 B2 |
| APPLICATION NO. | : 15/008276 |
| DATED | : April 16, 2019 |
| INVENTOR(S) | : Michael Zhadkevich |

It is certified that error appears in the above-identified patent and that said Letters Patent is hereby corrected as shown below:

In the Claims

Claim 1, Column 39, Line 67, replace "having unactuated" with --having an unactuated--.
Claim 1, Column 40, Line 20, replace "air" with --an--.

Signed and Sealed this
Eighth Day of February, 2022

Drew Hirshfeld
*Performing the Functions and Duties of the
Under Secretary of Commerce for Intellectual Property and
Director of the United States Patent and Trademark Office*